United States Patent [19]

Blough

[11] Patent Number: 5,491,135

[45] Date of Patent: Feb. 13, 1996

[54] COMPOSITIONS OF N-(PHOSPHONOACETYL)-L-ASPARTIC ACID AND METHODS OF THEIR USE AS BROAD SPECTRUM ANTIVIRALS

[75] Inventor: Herbert A. Blough, Berwyn, Pa.

[73] Assignee: U.S. Bioscience, Inc., West Conshohocken, Pa.

[21] Appl. No.: 32,234

[22] Filed: Mar. 17, 1993

Related U.S. Application Data

[63] Continuation-in-part of Ser. No. 853,454, Mar. 18, 1992, abandoned.

[51] Int. Cl.⁶ .................................................. A61K 31/505
[52] U.S. Cl. ........................... 514/115; 514/119; 514/561
[58] Field of Search ................................. 514/115, 119, 514/561

[56] References Cited

U.S. PATENT DOCUMENTS

| | | |
|---|---|---|
| 4,154,759 | 5/1979 | Parsons et al. . |
| 4,178,306 | 12/1979 | Parsons . |
| 4,179,464 | 12/1979 | Schultz et al. . |
| 4,211,771 | 7/1980 | Witkowski et al. . |
| 4,215,070 | 7/1980 | Schultz et al. . |
| 4,267,126 | 5/1981 | Schultz et al. . |
| 4,272,528 | 6/1981 | Von Esch et al. . |
| 4,315,001 | 2/1982 | Blough . |
| 4,348,522 | 9/1982 | Schultz et al. . |
| 4,544,634 | 10/1985 | Krenitsky . |
| 4,562,203 | 12/1985 | Bruzzese et al. . |
| 4,714,703 | 12/1987 | Burckhalter . |

FOREIGN PATENT DOCUMENTS

| | | |
|---|---|---|
| PCT/US90/ 05942 | 10/1990 | WIPO . |
| 91/06863 | 10/1990 | WIPO . |

OTHER PUBLICATIONS

Collins et al., "Aspartate Transcarbamylase: Interaction with the Transition State Analogue N-(Phosphonacetyl)-L-Aspartate" *J. Biol. Chem.* 246(21):6599–6605 (1971).

Swyryd et al., "N-(Phosphonacetyl)-L-Aspartate, a Potent Transition State Analog Inhibitor of Aspartate Transcarbamylase, Blocks Proliferation of Mammalian Cells in Culture", *J. Biol. Chem.* 249(21):6945–6950 (1974).

Yoshida et al., "Inhibition by N-(Phosphonacetyl)-L-Aspartate of Aspartate Transcarbamylase Activity and Drug–induced Cell Proliferation in Mice", *J. Biol. Chem.* 249(21):6951–6955 (1974).

Johnson et al., "Effects of N-(Phosphonacetyl)-L-Aspartate on Murine Tumors and Normal Tissues in Vivo and in Vitro and the Relationship of Sensitivity to Rate of Proliferation and Level of Aspartate Transcarbamylase", *Cancer Research* 38:371–378 (1978).

Mao et al., "Structure–Activity Studies on Phosphonoacetate", *Antimicrobial Agents and Chemotherapy* 27(2):197–202 (1985).

Cole et al., "Carrot Cells Detoxify N–Phosphonoacetyl-L-Aspartate by Esterification", *Biochem. J.* 255:813–816 (1988).

*Primary Examiner*—José G. Dees
*Assistant Examiner*—Dwayne C. Jones
*Attorney, Agent, or Firm*—Pennie & Edmonds

[57] ABSTRACT

Compositions and methods are disclosed which utilize the broad spectrum antiviral activity of PALA. This compound and its pharmaceutically acceptable analogs possess potent activity while displaying minimal toxicity and, therefore, are characterized by a relatively high therapeutic index. Compositions optionally containing other therapeutic agents, such as other antiviral agents, are also disclosed and are found to possess synergistic and/or additive antiviral activity.

13 Claims, 9 Drawing Sheets

COMPOSITIONS OF N-(PHOSPHONOACETYL)-L-ASPARTIC ACID AND METHODS OF THEIR USE AS BROAD SPECTRUM ANTIVIRALS

This application is a continuation-in-part of U.S. application Ser. No. 07/853,454, filed Mar. 18, 1992, now abandoned, which is incorporated herein in its entirety.

TABLE OF CONTENTS

1. Field of the Invention
2. Background of the Invention
2.1 PALA
2.2 Antiviral Drug Development in General
3. Summary of the Invention
4. Brief Description of the Invention
5. Detailed Description of the Invention
5.1 Treatment of Viral Infections with PALA
5.2 Prophylactic and Other Uses of PALA
5.3 Dosage
5.4 Pharmaceutical Compositions
   5.4.1 Preparation of PALA
   5.4.2 PALA Analogs
   5.4.3 Pharmaceutical Preparations
5.5 Animal Model Systems for Evaluation of Combination Therapy
   5.5.1 Murine Model System for Bunya- and Flavivirus
   5.5.2 Rabbit Model System for HCMV
   5.5.3 Primate Model for RSV
6. Examples
6.1 Example 1
   6.1.1 Materials and Methods
   6.1.2 In Vitro Antiviral and Cytotoxicity Assays
   6.1.3. Results
7. Example 2
8. Example 3
8.1 Materials and Methods
8.2 Results
9. Example 4
9.1 Methods
9.2 Results
   9.2.1 AD169 Infected Hs68 Cell Monolayers
   9.2.2 Clinical HCMV Isolate
   9.2.3 DHPG Resistant HCMV
10. Example 5
10.1 Methods
10.2 Results
10.3 Conclusion
11. Example 6
11.1 Methods
11.2 Results
11.3 Conclusion
12. Example 7
12.1 Methods
12.2 Results
12.3 Conclusion
13. Example 8
13.1 Materials and Methods
3.2 Results
14. Example 9
14.1 Materials and Methods
14.2 Summary of Results of an Experiment Testing PALA for Antiviral Activity Against RSV in Cotton Rats
   14.2.1 Procedure
   14.2.2 Results
14.3 Conclusion

1. FIELD OF THE INVENTION

The present invention relates to methods of treating a broad range of viral infections in humans and animals, including birds, using pharmaceutical preparations in which the active ingredient comprises N-(phosphonoacetyl)-L-aspartic acid (PALA) or pharmaceutically acceptable analogs thereof. These compositions possess potent broad spectrum antiviral activity and may be used either alone or in conjunction with other therapeutic agent(s) to treat viral infections.

2. BACKGROUND OF THE INVENTION

2.1 PALA

PALA is a compound which was initially developed as a transition state analogue inhibitor of aspartate transcarbamylase. Stark et al. (1974) *J. Biol. Chem.* 246:6599. Subsequently, PALA (NSC No. 224131) was thoroughly studied as an anti-cancer agent. See, for example, Johnson et al. (1976) *Cancer Res.* 36:2720–2725; Erlichman et al. (1982) *J. Nat. Cancer Inst.* 68:227–231.

PALA, its salts and analogues, and the preparation thereof are described in U.S. Pat. Nos. 4,179,464, 4,215,070, 4,267,126, 4,348,522 and British Patent Nos. GB 2008118 and GB 2051070 to Schultz et al. as well as in U.S. Pat. Nos. 4,154,759 and 4,178,306 to Parsons et al.

N-(phosphonoacetyl)-L-aspartic acid (PALA) inhibits de novo pyrimidine biosynthesis by blocking the enzyme, L-aspartic acid transcarbamylase (ATCase)—this enzyme catalyzes the condensation of L-aspartate and carbamyl phosphate the condensation of which is essential in the synthesis of orotic acid and the end product, uridine. The ultimate result of the inhibition is depletion of nucleotide pools viz UTP, CTP as well as nucleotide intermediates, viz., UDP-GlcN, CMP-NeuNAc which are essential for elongation of the oligosaccharide chain(s). Johnson, R. K., Aeon, T., Golden, A. and Stark, G. R. (1985) *J. Med. Chem.* 28:2720–262. Clinical Brochure, NSC No. 224131, Div. of Cancer Treatment, National Cancer Institute, Bethesda, Md. 1977. Thus, while PALA acts primarily by inhibiting nucleotide biosynthesis, the effect on its intermediates is also reflected in its end products: carbohydrates, proteins, as well as nucleic acids (RNA and DNA).

PALA exerts its action as a competitive inhibitor of carbamyl phosphate and as a non-competitive inhibitor of aspartate. Hooengraad, N.J. (1974) *Arch. Biochem. Biophys.* 161:76–82. Its Ka is 1000× more avid than that of the natural substrate, carbamyl phosphate. Moore, E. C., Friedman, J., Valdivieso, M., Plunkett, W. Marti, J. R. et al. (1982) *Biochem Pharmacol.* 31:3317–3321. Because of its relative lack of toxicity and the sensitivity of several solid murine tumors lines, PALA has been used in experimental oncology studies. Recent studies have shown that PALA possesses unique modulatory activity when used in combination with halogenated pyrimidines, e.g., 5-fluorouracil, both in vitro and in vivo. Liang, C., Donchower, R. C. Chabner, B. A. (1982) *Mol. Pharmacol.* 21:224–230; Ardalan, B., Galzer, R. I. Kenslet, T. W. et al. (1981) *Biochem. Pharmacol.* 30:2045–2049; Anakarahanonta, T., Holstege, A. and Keppler, D. O. R. (1980) *Eur. J. Cancer* 16:1171–1180. Most recently, PALA has been disclosed as a pyrimidine biosynthesis inhibitor which is useful for the treatment of autoimmune diseases, chronic inflammatory diseases, and of organ transplantation rejections. International Application PCT/ US90/05942, published May 16, 1991 as WO91/06863.

A review of the literature has shown that PALA, when used alone for the treatment of cancer (neoplasia), is relatively nonefficacious in the clinical setting. Valdivies, M., Moore, E. C., Burgess, A. M., Marti, J. R., Russ, J., Plunkett, W. (1980) *Cancer Treat. Rep.* 46:1301–1305; Ehrichman, C., Strong J. M., Wiernik, P. H., McAvoy, L. M., Cohen, M. H. Levine, A. S., Hubbard, S. M., and Chabner, B. (1979) *Cancer Res.* 39:3992–3995; Grem, J. L. King, S. A., O'Dwyer, P. J. and Leyland-Jones, B. (1988) *Cancer Res.* 46:4411–4454.

A report on structure-activity relations involving phosphonoacetic acid ("PAA") and its analogs has appeared (Mao, J. C. H. et al. 1985 *Antimicrob. Agents Chemother.* 27(2):197–202). These workers found that PAA was a selective antiherpesvirus agent and that derivatization of PAA resulted in lower activity without exception. Specifically, PALA was found to be markedly less effective than the parent PAA by a factor of over 200.

2.2 Antiviral Drug Development in General

Since the discovery that halogenated nucleosides could be used as antivirals in the treatment of herpes keratitis, there was a long lag period before the development of sophisticated technology to permit the synthesis of chain terminators, e.g., acycloguanosine for HSV, 2',3'-dideoxythymidine analogues, e.g., AZT, ddI, and ddC for HIV; ribavirin (virazole®) for Lassa fever, Hantaan and respiratory syncytial viruses; carbocyclic nucleosides, cyclobut-A, which had broad spectrum antiviral activity against HIV and the herpesviruses (CMV, HSV, varicella) and the acyclic nucleoside, phosphonyl-methoxyethyladenine (PMEA) which has a wide range against RNA and DNA viruses. Ofttimes many of these compounds have proven too toxic for clinical usage and/or rapidly lead to the development of drug-resistant strains; of these latter viruses, many seem to show cross-resistance to comparable compounds, e.g., AZT with ddC; the development of drug resistance or toxicity has led to the use of combinational therapy, initially for HIV, for both additive and/or synergistic effects. Larder, B. A., Purifoy, D. J. M., Powell, K. L. and Darby, G. (1987) *Nature* (Lond.) 327:716–717. DeClercq, Erik E. (1987) *Cancer Res.* 7:1023–1038.

Another antiviral is 2-deoxy-glucose (2-dGlc) which is disclosed in U.S. Pat. No. 4,315,001. This compound has had little success against the "exotic" RNA viruses (e.g., those viruses which are not indigenous to the United States), presumably, since N-linked glycosylation does not appear to play a major role in the infectious process (as well as the fact that there may be only a few oligosaccharide chains on the latter group). However, Blough, H. A., Kefauver, D., Clausen, H. and Hansen, J. S. (1991) *Proc. Amer. Soc. Trop. Med. and Hyg.* 45:168 Boston, Mass. (abstract) have recently reported the presence of primitive carbohydrate neo-antigens, which may be O-linked on sandfly fever (SFS) and yellow fever (YF) virions; pretreatment of these RNA viruses with specific monoclonal antibodies, directed against these carbohydrates, did neutralize these bunya- and flaviviruses.

Newer drugs which do bind to the RT of HIV and glycosylation inhibitors (e.g., 2-dGlc) which prevent fusion and therefore, entry of the virus, are known. Cytokines (e.g., interferons), inhibitors of regulatory genes, adamantidine which blocks uncoating of influenza virus and the newer compounds targeted at the receptor level, are also known. However, what is clear is that at the time of the present invention, broad spectrum antivirals were not considered possible, primarily because of putative toxicity, and lack of "targeting". Much of the newer approaches have been genetic and/or molecular: antisense or nonsense oligomers, genetically engineered and/or synthetic peptides as vaccines, and/or targeted protease inhibitors-which are all "aimed" against a single virus (viz, those with a unique or conserved nucleotide and/or amino acid sequences).

In view of the present state of the art it is desirable to have a broad spectrum antiviral which could be used either alone or in combination with other therapeutics, particularly other antivirals, in order to treat or prevent viral infections. Clearly, with respect to combination therapy such a broad spectrum antiviral should have the benefit of reducing the toxicity or adverse effects of antivirals which are presently utilized, thereby providing a better therapeutic index.

3. SUMMARY OF THE INVENTION

The present invention relates to methods of treating or preventing vital infections in humans, animals and birds by administering an effective amount of PALA or a pharmaceutically acceptable analog alone or in combination with other therapeutic agents. Another aspect of the present invention encompasses pharmaceutical compositions and formulations for treating or preventing human or veterinary viral infections wherein said compositions comprise an effective amount of PALA or a pharmaceutically acceptable analog thereof. The invention is based in part on the discovery that although it has been reported that PALA when used alone is relatively nonefficacious in treatment of cancer, the opposite is true when PALA is used as an antiviral—PALA possesses broad spectrum antiviral activity when used alone and PALA has additive and/or synergistic effects when acting in concert with other therapeutics, including but not limited to antiviral agents and/or inhibitors of viral replication.

Thus, it is an object of the present invention to provide an antiviral compound which is effective against a broad spectrum of viruses.

A further object of the present invention is to provide combinational therapy which prevents viruses from potentially bypassing the inhibitory effect of PALA. In addition, a further object of the present invention is to provide combinational therapy which allows for reduced toxicity of PALA and/or the therapeutic agent with which PALA is used.

Another object of the present invention is to provide methods of treating humans, animals and birds suffering from (or potentially exposed to) infections caused by viruses, including retroviruses; and to provide methods for preventing such infections in humans, animals and birds (chemoprophylaxis).

A further object of the present invention is to provide pharmaceutical compositions for treating humans, animals and birds suffering from (or potentially exposed to) viral infections. Such pharmaceutical compositions are also effective for preventing such infections in humans, animals and birds.

An object of the present invention is to provide a broad spectrum antiviral compound which has a low level of toxicity, and therefore, has a higher therapeutic index.

Yet another object of the present invention is to provide a broad spectrum antiviral that has unique utility against drug resistant viral strains when used alone or in combination with other therapeutics, including but not limited to antiviral agents and/or inhibitors of viral replication.

Still a further object of the present invention is to provide pharmaceutically acceptable analogs of PALA which exhibit antiviral activity on oral administration.

These and other objects of the present invention will be apparent to those of ordinary skill in the art in light of the present description and appended claims.

4. BRIEF DESCRIPTION OF THE FIGURES

5. DETAILED DESCRIPTION OF THE INVENTION

Figure 1:
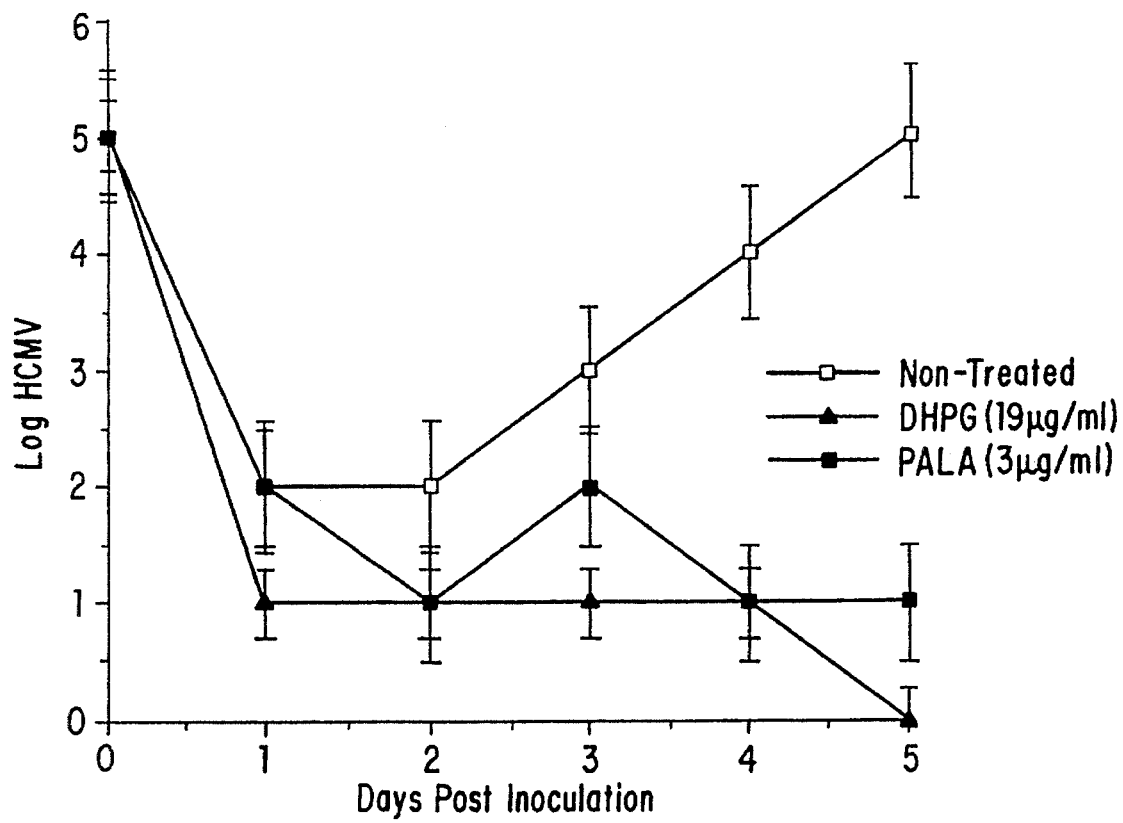
FIG. 1 is a graph of AD 169 HCMV titers recovered from supernatant assays after incubation with DHPG (ganciclovir).

The present invention encompasses a method of treating a broad spectrum of viral infections in humans and animals, including birds, comprising administering to the human or animal subject in need of treatment or prevention of a viral infection an effective amount of PALA or a pharmaceutically active analog thereof. The method of the invention also encompasses combination therapy in which PALA and at least one other therapeutic agent are administered as an admixture or sequentially. The present invention also encompasses pharmaceutical compositions in which the active ingredient comprises the compound PALA or an appropriate analog and, optionally, in an admixture with at least one selected drug for use in the treatment of viral infections in humans, animals and birds.

The invention is based, in part, on the discovery that PALA, a drug which has been reported to be ineffective in the treatment of cancer when used alone, is effective when used as a broad spectrum antiviral. PALA, when used alone or in combination with other drugs, demonstrates widespread utility as an antiviral agent useful in both human and veterinary medicine.

5.1 Treatment of Viral Infections with PALA

Viruses, by definition, are obligatory intracellular parasites which take over the host cell machinery and use existing intracellular structures e.g., polysomes, endoplasmic reticulum, golgi, and specific host cell macromolecules viz, enzymes, tRNA etc. to produce a template or transcript of viral mRNA. Viral nucleic acids are transcribed using unique polymerases and viral proteins are translated (both structural and non-structural) using viral mRNA. Post-translational modifications (cleavage by proteases and glycosylation) may occur. Viral assembly occurs de novo (naked nucleocapsids) or using a lipid membrane, in which are embedded repeating surface projections (glycoproteins). In the latter case, the envelope surrounds the nucleocapsid. The viruses which are amenable to treatment with PALA, in accordance with the invention, encompass all types and classes of known viruses including both DNA and RNA viruses (both positive and negative stranded viruses). PALA can be used against DNA and RNA viruses and virus types including but not limited to the following:

Adenoviruses
Poxviruses
    vaccinia
    molluscum contagiosum virus
    vaccinia viral constructs
Bunyaviruses
    Rift Valley fever virus
    Sandfly fever virus
    Dengue viruses
    Punta Toro
Flaviviruses
    yellow fever virus
    Japanese encephalitis virus
Herpesviruses
    Cytomegalovirus (CMV)
    varicella
    human herpesvirus-6
    Marek's disease virus (veterinary)
    Equine anemia virus
    herpesviruses 1 and 2
    Epstein-Barr virus (EBV)
Paramyxoviruses
    respiratory syncytial virus (RSV)
    measles virus
    parainfluenza viruses
    rinderpest virus (veterinary)
    Newcastle disease virus (veterinary)
    mumps
Orthomyxoviruses
    influenza A ($H_2N_2$ and $H_3N_2$)
    influenza B (certain strains)
    influenza C
Hepadnaviruses
    hepatitis B
Other Hepatitis viruses (not yet fully classified)
    hepatitis A (HAV)

hepatitis C (HCV)
hepatitis E (HEV)
Picoanaviruses
   polioviruses
   coxsackieviruses
   ECHO viruses
   foot and mouth disease (FMDV) (veterinary)
   rhinoviruses
Rhabdoviruses
   rabies virus
Togaviruses
   Venezuelan equine encephalitis virus
Filoviruses
   Ebola virus
   Marburg virus
Papovaviruses
   human papilloma virus
Rubiviruses
   rubella virus
Orbiviruses
   Colorado tick virus
   Junin and Machupo viruses
Hantaan Viruses
   Hantaan hemorrhagic fever virus
   Congo/Crimean hemorrhagic fever virus
Retroviruses and Lentiviruses
   HTLV 1 and 2
   HIV 1 and 2

As used herein, the term "viral infections" describes a diseased state in which a virus invades healthy cells, uses the cell's reproductive "machinery" to multiply or replicate and ultimately lyses the cell resulting in cell death, release of viral particles (virions) and the infection of other cells by the newly produced progeny viruses. Latent infection by certain viruses is also a possible result of viral infection. It is clear that one skilled in the art would understand the meaning of these terms and the disease and/or infections to which it relates.

Further as used herein the phrase "treating or preventing viral infections in humans, animals or birds" means to inhibit the replication of the particular virus or to prevent the virus from establishing itself in its host, and to ameliorate or alleviate the symptoms of the disease caused by the viral infection.

PALA and its pharmaceutically acceptable analogs can be used alone or in combination with other therapeutic agents when used against these viruses. It has been found that when treating herpesviruses it is preferred that PALA be used in combination with other therapeutic agents such as the antivirals acyclovir or ganciclovir. The use of PALA, or a pharmaceutically acceptable analog, in combination therapy against herpesviruses provides benefits over the presently available therapies; for example the reduced toxicity of the antivirals presently used to treat these viral infections. In addition, PALA, or a pharmaceutically acceptable analog thereof, can have a unique utility against drug resistant strains of herpesviruses, such as acyclovir or ganciclovir resistant strains. Moreover, PALA or a pharmaceutically acceptable analog thereof, may be useful in prolonging or blocking the development of drug resistant viral strains e.g., DHPG or acyclovir.

It has also been discovered that PALA, or a pharmaceutically acceptable analog thereof, can be used alone or in combination with other therapeutics, such as the antiviral rifampicin, to treat or prevent infection by vaccina virus or vaccina viral constructs used to prepare vaccines. The occupational hazards involved in using such vaccinia constructs would thus be minimized. Generally, immunocompromised individuals can be protected or treated with PALA, or a pharmaceutically acceptable analog thereof.

It has also been found that PALA, or a pharmaceutically acceptable analog thereof, is more effective as a single agent therapy in vivo against respiratory syncytial virus than ribavirin.

Five major types of viral hepatitis have been identified (Consolo and Freni, *Nephron* 61: 252–254, 1992), and these represent diverse molecular groups of viruses (both DNA and RNA). These viral hepatitis viruses are hepatitis A (HAV), hepatitis B (HBV), hepatitis C (non-A, non-B hepatitis or HCV), hepatitis D (delta agent or HDV) and hepatitis E (HEV). A broad spectrum antiviral is an ideal agent against these viruses because of their genetic and molecular diversity. The use of PALA, or a pharmaceutically acceptable analog, either alone or in combination with another therapeutic agent, including other antivirals, to treat or prevent viral infection by hepatitis A, hepatitis C and hepatitis B is within the scope of the present invention. In particular, PALA can be used alone, or in combination with DHPG (ganciclovir), phosphonoformate, 3TC (Biochem Pharma and Glaxo), $\alpha$-interferon ($\alpha$-2b IF) or steroids which are commonly used to block the inflammatory response in hepatitis, to treat or prevent viral infection from hepatitis B.

To illustrate its broad antiviral activity, we tested PALA against a number of viruses, e.g., those of military import such as flavi-, bunya- and togaviruses, and in a screen which included vaccinia virus. The presence of the latter virus is of unique import because of the widespread use of plasmid constructs in which vaccinia is used as a vector to produce live vaccines. The experiments were subsequently expanded from the flavi-, toga- and bunyaviruses to viruses of public health importance in the continental United States such as myxoviruses, herpesviruses (CMV, varicella), paramyxoviruses, and positive polarity RNA viruses (picornaviruses) as well as retroviruses. While not limited to any theory, we believe that PALA exerts its antiviral effect by either inhibiting early steps of pyrimidine biosynthesis, viz. ATCase, decreasing nucleotide pools or inhibition of viral DNA polymerase, yielding the activity noted in Tables 1–3, infra.

Moreover, PALA has been tested against duck hepatitis B in a primary duck hepatocyte culture; against simian varicella virus infection in African green monkeys; against vaccina virus in African green monkeys; and against human cytomegalovirus (HCMV) both in vitro and in rabbits. The results of these studies appear in the examples, infra.

PALA may be used in combination with another therapeutic agent(s) to enhance the antiviral effect achieved. For example, such additional antiviral agents include but are not limited to those which function on a different target molecule involved in viral replication; those which act at a different loci of the same molecule; those which inhibit salvage pathways (described below) in order to prevent or reduce the occurrence of viral resistance.

When PALA or a pharmaceutically acceptable analog of PALA is used in combination therapy it is preferred that PALA be given separately from, but simultaneously with the other agent. In addition, PALA can be given intermittently.

Although viruses possess their own DNA or RNA polymerases, the more complex viruses viz, herpesvirus and poxvirus, to name a few, also possess individual enzymes responsible for nucleoside biosynthesis, e.g., phosphoribosyltransferases or nucleoside phosphorylase(s) which are also present as host cell enzymes. These enzymes may impart an alternative route or "salvage pathway" for pyrimidine synthesis, bypassing the inhibitory effect of antiviral agents. Thus, as with certain tumors, viral resistance to antiviral compounds could emerge. However, this possibility may be circumvented by combinational therapy, e.g., using nucleoside analogues including but not limited to adenine arabinoside, adenine arabinoside monophosphate, idoxuridine, trifluorothymidine, acycloguanosine, bromovinyldeoxyuridine, bromovinyldeoxyarauridine (BVaraU by Bristol-Myers Squibb) fluoroiodoaracytosine, DHPA and ribavirin (virazole®), glycosylation inhibitors (e.g., 2-dGlc), protease inhibitors, interferons, nucleoside transport inhibitors such as dipyridamole and nitrobenzylthioinosine, DNA dependant RNA polymerase inhibitors, e.g., rifampicin (rifadin®), chain terminators, e.g., ganciclovir (DHPG), acyclovir (ACV), AZT, ddC, ddI in conjunction with PALA and other antiviral agent(s).

In addition to the experiment summarized in the Tables 1–3, infra, we conducted experiments using PALA in conjunction with other antiviral compound(s); for example, PALA was used in combination with ribavirin (virazole®) for Sandfly valley fever virus and with 2-deoxy-D-glucose (2-dGlc), a known antiviral against HSV which has undergone extensive clinical trials in man. Blough, H. A. and Giuntoli, R. G. (1979) *J. Amer. Med. Assoc.* 241:2798–2801. PALA can also be used optionally with rifampicin (rifadin®) for vaccinia; optionally with AZT, ddI, ddC and combinations thereof for HIV-1 and 2; optionally with adamantidine for influenza; optionally with ribavirin (virazole®) for Lassa fever, Hantaan and CCHF viruses; and optionally with acyclovin ACV for varicella-zoster and optionally with interferon-α or fluorouracil for human papilloma virus.

The results of the foregoing experiments demonstrate that PALA in combination with other viral inhibitors, achieved a higher inhibitory effect than either compound alone. For example, 2-dGlc had no effect itself against flaviviruses, but a potentiating effect was observed with PALA and 2-dGlc against SFS. Further, combinational therapy with PALA and AZT produced ca. a 20% additional decrease in viral replication of HIV-1, as measured by a reduction of p24 by radioimmunoprecipitation or by western blots (quantified by densitometry) when compared to untreated controls and those HIV-infected cells receiving a single antiviral (AZT only or PALA only). Moreover, the use of PALA in conjunction with another antiviral agent allows for the use of a lower dosage of one or both active agents so that the therapeutic index is increased, and toxic side effects are reduced.

Because PALA does not appear to significantly alter humoral immune response—at least in tumor bearing animals (Johnson, R. K. Swyryd, E. A. and Stark, G. R. (1978) *Cancer Res.* 38:371–378), the use of PALA in accordance with the present invention would permit concurrent immunization for certain viruses (with appropriate vaccines, e.g., inactivated viruses or synthetic peptides as immunogens). As mentioned above, a potential problem to be encountered will be the possible evolution of resistant strains through mutation or selection or because of the ability of certain viruses (or cells) to use "salvage" pathways for DNA synthesis; these salvage pathways appear to be operative in HSV-infected cells—hence no effect.

In addition, PALA is able to cross the bloodbrain barrier and thus, relatively high concentrations can be achieved in the retina and brain; thus, PALA may also prove useful in HIV-induced encephalopathy and in CMV-induced and varicella-induced retinitis.

5.2 Prophylactic and Other Uses of PALA

PALA may be used as a prophylactic for individuals entering geographic zones where certain "exotic RNA viruses" are prevalent, yet immunization is not available (for that virus) or has not taken effect. Additionally, polyvalent, genetically engineered vaccines may use a vaccinia construct; thus the possibility of generalized vaccinia in a patient and or a laboratory worker is real. The accessibility of a drug like PALA alone, or in combination with rifampicin (rifadin®), offers the treating physician a unique opportunity to intervene. Many of the above individuals (exposed occupationally) to such genetically engineered viruses could be treated with PALA on an outpatient basis either prophylactically or therapeutically.

PALA may also have usage in pregnancy to prevent perinatal transmission of viruses, provided that there is no teratogenic effect. PALA may be useful in transplant surgery, e.g., renal and bone marrow transplant recipients undergoing chemotherapy as well as cancer patients since organ or bone marrow grafts are frequently contaminated with CMV. To prevent the replication of the virus which is present in the donor tissue, both the recipient and the donor are treated with PALA either alone or with combinational therapy at the discretion of the treating physician, e.g., prior to donating or receiving the tissue or organ transplant.

PALA may be useful for respiratory syncytial virus (RSV) in addition to those paramyxoviruses (including measles) which infect man, therefore PALA could be administered to infants intravenously possibly without using the expensive positive pressure machines necessary for ribavirin (virazole®). In addition, the results with PALA on the flavi-, toga- and bunyaviruses (Table 1) provide a new therapeutic and chemoprophylactic approach against these "exotic" viruses that can be encountered in remote areas of the world; PALA should be efficacious against Ebola, Marburg and Lassa fever viruses. Furthermore, viruses of veterinary importance, e.g., foot and mouth disease (FMDV), rinderpest, Newcastle disease, pseudorabies and equine anemia and bovine rhinotracheitis viruses may be now amenable to intervention with PALA; thus PALA may prevent or control epizootics and prevent or ameliorate the severe economic loss associated with viral diseases including but not limited to livestock, birds or horses, especially race horses.

5.3 Dosage

In treating animals having a viral infection, particularly humans, a therapeutically effective amount of PALA is administered, i.e., a dose sufficient to inhibit viral replication. For example, PALA may be administered as an infusion (IV) at about 1 to about 100 mg/kilogram per day for about 1 week to about 1 month. A preferable dose is from about 25 to about 50 mg/kg; the equivalent daily dose of PALA or a pharmaceutically acceptable analog thereof based on surface area is from about 100 to about 600 mg/m$^2$. The most preferred dose is about 5 mg/kg to about 60 mg/kg for 1 week to about 1 month. Doses of PALA or its pharmaceutically acceptable analog should be administered in intervals of from about 1 week to about 1 month and preferably from about 7 to about 10 days. A preferred dose is administered to achieve peak plasma concentrations of PALA or its pharmaceutically acceptable analog from about 50 to about 100 μM. This may be achieved, for example, by the intravenous injection of a sterile about 0.05% to about 10% solution of the administered ingredients in buffered saline (≈pH 7.5) (any suitable saline solutions known to those skilled in the art of medicinal chemistry may be used). Desirable blood levels may be maintained by a continuous infusion of PALA as ascertained by plasma levels measured by HPLC. Combination therapy with PALA or a pharmaceutically acceptable analog is achieved by lowering the dose of each drug about 25% to 50%. It should be noted that the attending physician would know how to and when to terminate, interrupt or adjust therapy to lower dosage due to toxicity, or bone marrow, liver or kidney dysfunctions. Conversely, the attending physician would also know to adjust treatment to higher levels if the clinical response is not adequate (precluding toxicity). A program comparable to that discussed above can be used in veterinary medicine.

The magnitude of a prophylactic or therapeutic dose of PALA in the acute or chronic management of viral infections will vary with the severity of the condition to be treated and the route of administration. Again, it should be noted that the clinician or physician would know when to interrupt and/or adjust the treatment dose due to toxicity or bone marrow, liver or kidney dysfunctions. The dose, and perhaps the dosage frequency, will also vary according to the age, body weight, and response of the individual patient. In general, as discussed above, the total daily dose ranges for PALA or its pharmaceutically acceptable analog, for the majority of the viruses described herein, is from about 1 to about 100 mg/kg patient. Preferably, a daily dose range should be between about 5 to about 75 mg/kg, while most preferably a daily dose range should be between about 5 to about 60 mg/kg. Another preferred range is between about 25 to about 50 mg/kg per day. In managing the patient, the therapy should be initiated at a lower dose, perhaps about 5 mg/kg to about 10 mg/kg and increased up to about 25 mg/kg or higher depending on the patient's individual response. It is further recommended that infants, children, and patients over 65 years, and those with impaired renal, or hepatic function, initially receive low doses, and that they be titrated based on individual clinical response(s) and blood level(s). It may be necessary to use dosages outside these ranges in some cases as will be apparent to those of ordinary skill in the art. The various terms "an amount sufficient to alleviate or prevent viral infection", "an amount sufficient to treat or prevent viral infection" or "effective antiviral amount" are meant to encompass the above described dosage amounts and dose frequency schedule.

As discussed further below, any suitable route of administration may be employed for providing the patient with an effective dosage of PALA. For example, oral, parenteral (subcutaneous, intravenous and intramuscular); rectal, transdermal, vaginal and the like may be used. Dosage forms include tablets, troches, dispersions, suspensions, suppositories, solutions, capsules, creams, patches, minipumps (Alza Corporation) and the like.

5.4 Pharmaceutical Compositions

The pharmaceutical compositions of the invention which are useful in the treatment or prevention of viral infections in humans, animals and birds contain as an active ingredient PALA or a pharmaceutically acceptable analog thereof. These pharmaceutical compositions may also contain therapeutic agents including other antivirals, in addition to PALA or a pharmaceutically acceptable analog thereof; these novel compositions provide for combinational therapy for the treatment of viral infections. Such combinational therapy provides both additive and/or synergistic effects.

For example, pharmaceutical compositions containing PALA may optionally contain at least one other therapeutic agents such as nucleoside analogues, including nucleoside transport inhibitors; and chain terminators (e.g., dideoxynucleosides). Several compounds which are suitable for use in combinational therapy with PALA or a pharmaceutically active analog thereof can be found in Fields Virology, 2nd Edition, Raven 1990; White, D. O. and Fenner, F., Chapter 11 "Chemotherapy of Viral Diseases" in *Medical Virology*, 3rd Edition, Academic Press, Inc., Orlando, Fla. 1986, the disclosures of which are incorporated by reference herein. Suitable compounds which may be used in combinational therapy with PALA within the scope of the invention include but are not limited to 2-deoxy-D-glucose(2-dGlc), deoxynojirimycin, acycloguanosine, ribavirin (virazole®), rifampicin (rifadin®), adamantidine, rifabutine, ganciclovir, (DHPG) 3'-azido-3'-deoxythymidine (AZT or zidovudine®), 2',3'-dideoxyinosine (ddI), 2',3'-dideoxycytidine (ddC), fluoroiodoaracytosine, idoxuridine, trifluorothymidine, adenine arabinoside (ara-A), ara-AMP, bromovinyldeoxyuridine, bromovinylarauracil (BV-araU by Bristol-Meyers Squibb (1-beta-D-arabinofuranoside-E-5-[2-bromovinyl]uracil)) rimantadine, arildone, diarylamidine, (S)-9-(2,3-dihydroxypropyl)-adenine (DHPA), interferon-$\alpha$, dipyridamole, nitrobenzylthioinosine, S-(p-nitrobenzyl-)6-thioinosine and phosphonoformate. Novel pharmaceutical compositions encompassed by the present invention include but are not limited to PALA, or a pharmaceutically acceptable analog, and ribavirin (virazole®); PALA and rifampicin (rifadin®); PALA and AZT; PALA and ddI; PALA and ddC; PALA and adamantidine; PALA and acycloguanosine; PALA and 2-deoxy-D-glucose; PALA and deoxynojirimycin; PALA and interferon-$\alpha$ and PALA and ganciclovir. The present invention also encompasses pharmaceutical compositions which contain PALA, or a pharmaceutically acceptable analog, and, optionally more than one additional therapeutic compound to provide combinational therapy.

5.4.1 Preparation of PALA

PALA and a number of its analogues can be prepared according to methods described in U.S. Pat. Nos. 4,179,464, 4,215,070, 4,267,126, 4,348,522, 4,154,759, 4,178,306 and GB 2008118 and GB 2051070, the disclosures of which are incorporated in their entirety by reference herein. Further, PALA can alternatively be prepared according to the methods disclosed by Gloede, J. et al. (1988) *Pharmazie* 43(6):434; Henklein, P. et al. (1989) DD 272092 A1 Sep. 27, 1989; Kafarski, P. et al. (1982) *Synthesis* 3:219–221; Montero, J. L. et al. (1982) *Eur. J. Med. Chem.-Chim. Ther.* 17(1):97–99; Stiebitz, B. et al. (1991), DD 286589 A5 Jan. 31, 1991; Goodson, J. J. et al. (1980) *J. Chem. Soc., Perkin Trans.* 1(12): 2721–2727, the disclosures of which are incorporated in their entirety by reference herein.

5.4.2 PALA Analogs

In yet other particular embodiments of the present invention, a wide range of analogs of N-(phosphonoacetyl)-L-aspartic acid (PALA) may be used as broad spectrum antiviral agents. As is plain to those skilled in the art, PALA contains four highly acidic hydrogens (i.e., two carboxylic acid protons and two phosphonic acid protons) as well as a basic nitrogen substituent. Hence, many combinations between free acid, ester, inorganic or organic salt functionalities are possible. Such possibilities are better appreciated with the aid of the structural representation, below, of a generic formula of PALA which encompasses the free acids, salts, esters or compounds combining such functional groups. The terms "analog, analogs or analogues of PALA" as used herein are meant to encompass any salts, esters or other derivatives which can be made with PALA using its available functionalities. The term "PALA" as used herein is meant to encompass both the protonated acid or a pharmaceutically acceptable salt of N-(phosphonoacetyl)-L-aspartic acid. One preferred salt is the disodium salt; another is the tetrasodium salt, infra. The analogs of PALA can have particular utility in the pharmaceutical compositions of the present invention, especially those formulated for oral administration.

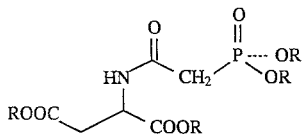

N-(phosphonoacetyl)-L-aspartic acid (PALA) nucleus

The R groups in the generic PALA nucleus illustrated above represent, independently, hydrogen, hydrocarbon, silane, organic salt or inorganic salt groups, as well as all possible combinations of such groups. When the R group is a hydrocarbon, the resulting analog can be referred to as a carboxylic acid ester or a phosphonate ester. The hydrocarbon group may have 1–20 carbon atoms, preferably 1–8, and may be cyclic, acyclic, aromatic or aliphatic in nature and may optionally contain functional groups such as hydroxyl groups, ether groups, amino groups, thioether groups, sulfhydryl groups, fluoro groups and the like. Specific examples of suitable hydrocarbon substituents include, but are not limited to, methyl ethyl, propyl, isopropyl, butyl, sec-butyl, isobutyl, tert-butyl, cyclohexyl, phenyl, benzyl, p-nitrobenzyl and the like.

The corresponding silane ester is obtained, of course, with R being a silane group, such as trialkylsilyl groups (e.g., trimethylsilyl, tri-tertbutylsilyl or methyl-di-tert-butylsilyl, and the like).

The present invention also contemplates the preparation and use of analogs of PALA as antiviral agents. In particular embodiments of the present invention, ammonium, mono-, di-, tri- and tetrasubstituted ammonium salts of PALA can be prepared by methods well-known to those skilled in the art, including, but not limited to, simple acid-base reactions between PALA and amines or passage through ion-exchange columns. As is readily apparent to one of ordinary skill, a wide variety of amines can be utilized to form the amine salt, including primary, secondary or tertiary amines. Indeed, even quaternary ammonium groups can form salts of PALA, so long as the PALA is already in the salt form. Of course, the amine salt of PALA can be associated, depending on the stoichiometry, strength of the particular base or substituent(s) present at the other acidic portions of the molecule, with only the phosphate group, one or both carboxylic acid groups, or all the acidic portions of the PALA nucleus as depicted in the structure above.

Though not intending to be limited solely to those species disclosed herein, the following amines are nonetheless enumerated for the benefit of the reader. Other suitable inorganic salts have already been noted elsewhere in the specification, and it should be understood that such inorganic salts could be present in combination with the hydrocarbon or silane ester groups, as well as the organic salts exemplified by the organic amines. Thus, inorganic sources of ammonium ion can be utilized to advantage, such as ammonium hydroxide, ammonium iodide, ammonium bromide, ammonium chloride and the like, in addition to ammonia, itself.

Organic amines are also suitable, as already mentioned. For example, lower alkyl (e.g., $C_1$–$C_4$ hydrocarbons) amine groups enjoy great utility. Alkanol amines, in which both amino and hydroxyl groups are present also, are particularly contemplated. Hence, methanolamine, ethanolamine, propanolamine, isopropanolamine, butanolamine and the like make attractive amine salts or analogs of PALA. Similarly, dialkanol, trialkanol, or tetraalkanolammonium groups are contemplated. Multiple amino group-containing compounds are also envisioned, such as ethylenediamine, diethylenetriamine or N-alkyl- or N-alkanol-substituted derivatives thereof. Moreover, the N-hydrocarbon substituents are defined similarly as the ester hydrocarbon groups described above, i.e., they may be cyclic, acyclic, aliphatic or aromatic and may optionally contain functional groups other than hydroxyl, such as ether groups, amino groups, thioether groups, sulfhydryl groups, fluoro groups and the like.

Illustrative methods for the preparation of PALA and its analogs are described in greater detail, for example, in the following references whose complete disclosures are incorporated by reference herein: Stiebitz et al., DD 286589 A5 (1991); Henklein et al., DD 272092 A1 (1989); Gloede et al., Pharmazie 43(6): 434 (1988); Mao et al., Antimicrob. Agents Chemother. 27(2): 197–202 (1985); Kafarski et al., Synthesis 3: 219–21 (1982); Goodson et al., J. Chem. Soc., Perkin Trans. 1(12): 2721–7 (1980); Montero et al., Eur. J. Med. Chem.-Chim. Ther. 17(1): 97–9 (1982); Cole et al., Biochem. J. 255 (3): 813–16 (1988); Starks et al., DE 2849396 (1979); Bakuniak et al., J. Environ. Sci. Health, Part B B18(4–5): 485–96 (1983); Collins et al., J. Biol. Chem. 246(21): 6599–605 (1971).

5.4.3 Pharmaceutical Preparations

The pharmaceutical compositions of the present invention comprise PALA as active ingredient, or a pharmaceutically acceptable analog thereof, and may also contain a pharmaceutically acceptable carrier, and optionally, other therapeutic ingredients.

As mentioned above, the term "pharmaceutically acceptable analogs" include salts, esters and other derivatives of PALA. The salts are prepared from pharmaceutically acceptable non-toxic acid or bases including inorganic acids or bases and organic acids or bases. Such salts may include alkali metal salts, such as sodium or potassium, and alkaline earth salts or ammonium salts. A variety of salts of PALA can be found in the patents of Schultz et al. and Parson et al. mentioned above.

Further, since the compound of the present invention is amphoteric, salts may be prepared from pharmaceutically acceptable non-toxic bases or acids including inorganic and organic bases or acids as well as metals. Suitable pharmaceutically acceptable base additions salts for the compound of the present invention include but are not limited to metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (n-methylglucamine) and procaine. A preferred salt is the tetrasodium salt of PALA and another preferred salt is the disodium salt of PALA.

In a particular embodiment of the present invention, preparations are disclosed which are suitable for oral, rectal, transdermal, topical, vaginal and parenteral (including subcutaneous, intramuscular, and intravenous) administration, although the most suitable route in any given case will depend on the nature and severity of the viral diseases being treated or prevented. In addition, pediatric formulations are within the scope of the present invention, where it may be necessary to add flavoring agents and to lower the dosage form. A preferred route of administration is by intravenous injection. The present compositions may be conveniently presented in unit dosage form, and prepared by any of the methods well known in the art of medicinal chemistry.

In practical use, PALA can be combined as the active ingredient in intimate admixture with a pharmaceutical carrier according to conventional pharmaceutical compounding techniques. The carrier may take a wide variety of forms depending on the form of the preparation desired for administration, e.g., oral or parenteral. In preparing the compositions for oral dosage form any of the usual pharmaceutical media may be employed. Usual pharmaceutical media includes, for example, water, glycols, oils, alcohols, flavoring agents, preservatives, coloring agents, and the like in the case of oral liquid preparations (for example, suspensions, solutions, and elixirs); in the case of aerosols, surfactants for delivery through mucosal membranes; or carriers such as starches, sugars, microcrystalline cellulose, diluents, granulating agents, lubricants, binders, disintegrating agents and the like in the case of oral solid preparations (for example, powders, capsules, and tablets). Oral solid preparations are preferred over the oral liquid preparations. The most preferred oral solid preparations are those that come in the form of tablets or capsules. Rectal preparations when used can be prepared in a carbowax composition.

Because of their ease of administration, tablets and capsules represent the most advantageous oral dosage unit form, in which case solid pharmaceutical carriers are employed. If desired, tablets may be further coated by standard aqueous or non-aqueous techniques.

In addition to the common dosage forms set out above, the compounds of the present invention may also be administered by controlled release means and/or delivery devices including Alzet® osmotic pumps which are available from Alza Corporation. Suitable delivery devices are described in U.S. Pat. Nos. 3,845,770; 3,916,899; 3,536,809; 3,598,123; 3,944,064 and 4,008,719, the disclosures of which are incorporated in their entirety by reference herein.

Pharmaceutical compositions of the present invention suitable for oral administration may be presented as discrete units (e.g., as capsules, cachets, or tablets, or aerosols sprays) each containing a predetermined amount of the active ingredient, as a powder or granules, or as a solution or a suspension in an aqueous liquid, a non-aqueous liquid, an oil-in-water emulsion, or a water-in-oil liquid emulsion, or for topical or vaginal use in an appropriate cream. Such compositions may be prepared by any of the well known methods employed in pharmacology, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 100 mg to about 500 mg of the active ingredient, and each cachet or capsule contains from about 100 mg to about 500 mg of the active ingredient, PALA. Most preferably, the tablet, cachet or capsule contains either one of three dosages, about 100 mg, about 200 mg or about 500 mg of the active ingredient.

The compound of the present invention is particularly suitable for encapsulation, for example in liposomes or for crosslinking with protein carriers and the like. Several delivery systems of this nature are described in "Biological Approaches to the Controlled Delivery of Drugs", editor R. L. Juliano, Volume 507, Annals of the New York Academy of Sciences (1987), the disclosure of which is hereby incorporated by reference.

The formulation listed below is suitable for intravenous, subcutaneous, or intramuscular injection.

|  | Quantity | | |
| --- | --- | --- | --- |
| Formula | A | B | C |
| Active ingredient PALA, disodium salt | 125 mg | 250 mg | 500 mg |
| Sterile, pyrogen free $H_2O$ with EDTA (1.0 mg/ml) of PALA q.s.a.d. to 5 ml | 25 mg/ml | 50 mg/ml | 100 mg/ml |

A suitable tablet or capsule (containing PALA) composition is presented, below:

|  | Tablets | | |
| --- | --- | --- | --- |
|  | Quantity per Tablet in mg. | | |
| Formula | A | B | C |
| Active ingredient, PALA, di-sodium | 100 | 200 | 500 |

5.5 Animal Model Systems for Evaluation of Combination Therapy

The following animal model systems may be utilized to evaluate the efficacy of various treatment regimens using PALA or, an analog thereof, in combination with any of the aforementioned compounds.

5.5.1 Murine Model System for Bunya- and Flavivirus

Punta Toro virus: Compounds are evaluated in vivo against hepatotropic infection induced by subcutaneous (s.c.) inoculation of Punta Toro (Adames) virus in 3 week-old C57BL/6 mice (9.6–13.6 g) for 21 days as previously described for ribavirin (virazole®) (used as a positive control) and ribamidine. Sidwell et al., (1988) *Antimicrob. Agents Chemother.*, 32:331–336.

Japanese encephalitis virus: Groups of 10 C57B1/6 mice (VAF+, Charles River Labs.) weighing 12–14 g are treated i.p. with phosphate-buffered saline (PBS) or drug twice daily (b.i.d.) on a 5-day schedule with the first dose administered on the day (day-1) preceding viral challenge. Five of the ten animals in each group are infected s.c. with 10–100 $LD_{50}$ of JE virus (Beijing strain) adequate to produce 100% mortality in the diluent controls) 6 h after the first dose of compound is administered (day 0). Controls include untreated, uninfected mice; untreated, virus-infected mice, diluent-treated, virus-infected (and uninfected) mice. Poly (ICLC), a ribarivin®, is used as a positive treatment control. Six days after viral challenge (day +6), brains of infected mice are harvested for virus titres. Suspensions of brain (10% w/v) are titrated by plaque assay in Vero cell cultures. Body weights are recorded on days −1 through +6. Weight change is determined as a measure of drug toxicity.

5.5.2 Rabbit Model System for HCMV

A total of 20 pigmented rabbits are used in this study. Animals are evaluated by slit lamp and indirect ophthalmoscopy to determine normal ocular morphology and lack of pre-existing pathology. Animals are handled as follows:

(1) On day 0, all rabbits are inoculated by mid-vitriol injection of $10^6$ PFU HCMV strain AD 169.

(2) Animals are maintained in individual cages and developing chorioretinal HCMV disease is monitored on day 2 PI. On day 2 PI, HCMV-inoculated animals are divided into 4 groups of animals with matched chorioretinal disease scores, and receive intravenous therapy as indicated below.

Group #1—five animals, intravenous injection of drug daily in two divided doses on days 2, 3, 4, 5 and 6 PI. Concentration of the drug is ½ of the ED90 value determined in in vitro assays.

Group #2—five animals, intravenous injection of drug daily in two divided doses on days 2, 3, 4, 5 and 6PI. Concentration of the drug is the ED90 value determined in in vitro assays.

Group #3—five animals, intravenous injection of drug daily in two divided doses on days 2, 3, 4, 5 and 6PI. Concentration of the drug is 1 to 2 times the ED90 value determined in in vitro assays.

Group #4—five animals, Placebo intravenous injections (sterile saline) on days 2, 3, 4, 5 and 6 PI.

(3) All animals receive daily indirect ophthalmoscopic examinations to evaluate clinical HCMV disease progression. The indirect ophthalmoscopic examinations are performed independently by two readers who are masked as to the therapy that the rabbits are receiving.

(4) All animals are sacrificed on day 8 PI. Chorioretina and iris tissues and vitreous (and in some cases lung tissue) samples are removed and processed for HCMV recovery by cell sonicate assay on Hs68 cell monolayers. Selected tissue samples are processed for histochemistry to evaluate HCMV-induced ocular pathology in treated and non-treated groups.

The clinical and histological results are evaluated together with viral recovery for all drug-treated, intravenous therapy groups and are correlated with each other and with the group receiving placebo therapy. The results from this study allow one to select the optimal drug concentration for use as intravenous therapy for CMV induced retinitis.

5.5.3 Primate Model for RSV

Twenty-three young, African green monkeys, seronegative to RSV are used. All are housed individually in cages in a single room at the Primate Center. They are maintained at a temperature of 75°±3° F. with a relative humidity of 50–60 percent. Purina monkey chow and water are supplied ad lib and the animals are monitored daily for clinical signs and food consumption. At the termination of the experiment, all animals are killed while under ketamine anesthesia with Beuthansia D Special (euthanasia solution, Shering Corporation) and are necropsied.

Two strains of RSV are used; one is the Long type strain, (ATCC VR-26) and the second is derived from an Australian human RSV isolate provided by Dr. Gail Wertz, School of Medicine, University of Alabama at Birmingham. The viruses are passed twice in African green monkeys and are prepared as a stock pool in BSC-40 cells (African green monkey kidney). Viral pools have a titer of ca. $10^5$ TCID$_{50}$/mL and are maintained at −70°.

Virus inoculation consisted of a $10^{-1}$ or 10–2 dilution of stock FSV administered by intratracheal catheter (1.0 ml) and intranasal instillation (1.0 ml). Throat swabs are taken daily and placed in 1.0 ml of tissue culture medium (minimum essential medium with 10 percent fetal bovine serum and antibiotics). Titrations are performed on the 1.0 ml of medium after expression of fluid from the swab (Table I). Titrations are performed by preparation of serial ten fold dilutions of each specimen and inoculation of each dilution into duplicate wells of 24 well plates seeded with BSC-40 cells. Titers are obtained by microscopic examination of the cultures for viral induced cytopathology and the titers are expressed as TCID$_{50}$ per ml.

A small portion of lung is taken at necropsy from each monkey, weighed and ground in glass tissue grinders to a 10 percent homogenate in pH 7.2 phosphate buffered saline of which 0.1 ml is cultured on blood agar for bacteriologic evaluation. A portion of the homogenate and lung lavage(s) is diluted in tenfold dilutions for titration of virus in BSC-40 cells.

The gross changes are documented and the airways are then perfused with 10% buffered formalin. Tissue samples are then collected from the trachea and the nasal cavity and the entire lung structure is immersed in 10% buffered formalin. After 48 hours of fixation sections are made of each lung lobe, the trachea and turbinates are processed, using a standardized paraffin technique and sectioned at 4–6µ and stained with hematoxylin-eosin (HE); certain sections are stained with Periodic Acid Shiff (PAS) and Immunoperoxidase using a polyclonal antibody produced in the goat against Monkey (IgG, IgM, C3) (Nordic Immunologic Laboratories, Capistrano Beach, Calif.) and Histomark immunoperoxidase kit (Kirkegaard and Perry Laboratories, Gaitherburg, Md.).

The gross and microscopic changes are evaluated together with viral titer. The immunoperoxidase procedures are used to define the basement membrane changes seen prominently with the A-2 (Wertz) strain of RSV.

The invention is further defined by reference to the following examples describing the present invention. It will be apparent to those skilled in the art, that many modifications, both to materials and methods, may be practiced without departing from the scope and spirit of this invention.

6. EXAMPLES

6.1 EXAMPLE 1

6.1.1 Materials and Methods

PALA was received as a crystalline powder, as the disodium salt. It was stored in actinic glassware, and dissolved in sterile water or in Minimal Eagle's medium with 1% bovine serum albumin (as a 10X or 100X solution). All solutions were sterilized by passage through Millipore filters. The following cell lines were used: Vero or CEM; Hep-2 and human foreskin cells. Viral inhibition was determined using the method described in Pauwels et al. (1988)

J. Virol. Methods 20:309–321, the disclosure of which is hereby incorporated by reference, using 3-(4,5 dimethylthiazol- 2-yl)-2,5-diphenyl tetrazolium bromide (MTT).

6.1.2 In Vitro Antiviral and Cytotoxicity Assays

All assays were carried out in Vero cells except for the use of CEM cells in the HIV-1 assay. Compounds were evaluated for antiviral efficacy against the following viruses (viral strain): a) Japanese encephalitis virus, JE, (Nakayama); b) yellow fever virus, YF, (Asibi); c) sandfly fever virus, SF, (Sicilian); d) Punta Toro virus (PT), (Adames); e) Venezuelan equine encephalomyelitis virus (VEE), (Trinidad donkey); f) vaccinia virus (VV), (Lederle vaccine); g) dengue type-4 (Caribbean) virus; h) human immunodeficiency virus type i or 2, HIV 1 or 2. Viruses (a-f) comprised the standard group against which drugs were evaluated. The in vitro antiviral and cytotoxic effects of the test compound were measured either: a) by observing inhibition of viral cytopathic effect using an MTT-assay [JE, YF, SF, PT, VEE, VV and HIV-1 viruses], Pauwels et al. (1988) J. Virol. Methods 20:309–321, or b) by a general plaque reduction assay [all other viruses].

Basic measurements and definitions used herein include: (a) Cellular toxicity or concentration 50%, $TC_{50}$, is defined as the drug concentration (μg/ml.) that reduces the cell number and their metabolic activity by 50% as compared to the viability for uninfected control cells in duplicate test wells in the MTT assay; (b) Viral inhibitory concentration 50%, $IC_{50}$ is defined as the drug concentration (μg/ml) at which 50% reduction of viral cytopathic effect (CPE) is observed in triplicate test wells. The therapeutic (or antiviral) index, TI, is a value proportional to the overall in vitro activity. It is calculated as a ratio of ($TC_{50}/IC_{50}$). It is a single drug concentration measurement of the relative anticellular and antiviral effectiveness of a compound during the same test and time period. All in vitro MTT assay results given represent an average of 2–6 individual test results.

6.1.3 Results

The assay methods described above allow for the measurement of both viral replication and toxicity levels. Viable cells convert MTT tetrazolium to the blue MTT formazan (using mitochondrial enzymes); dead cells are incapable of this conversion. In addition screening is also supplemented with standard cytopathology and toxicity assays (by light microscopy). Serial concentrations of PALA are assayed as previously described except the cell sheets were pretreated with PALA for 16 hours prior to viral challenge. (See, for example, the method described by Kumarasamy, R. and Blough, H. A. (1984) Virology 138:156–161.) Appropriate inhibitor and viral controls are used and toxicity is evaluated. Therapeutic indices are calculated in the usual fashion as mentioned above; the results of the screening of the flavi-, toga- and bunyaviruses (RNA viruses) are given in Table 1; similarly confirmatory data for these viruses is reported in Table 2.

TABLE 1

EFFECT of PALA on BUNYA-, FLAVI and TOGAVIRUSES

| Virus | Cell Line | $IC_{50}$[a] | $TC_{50}$[b] | TI[c] | $TI_{(95)}$[d] |
|---|---|---|---|---|---|
| Punta toro | Vero | 15.2 | >320 | >21.05 | >10.00 |
| Sandfly fever | Vero | 20.9 | >320 | >15.32 | 0.00 |
| Yellow fever | Vero | 16.6 | >320 | >19.22 | >10.68 |
| Japanese encephalitis | Vero | 17.2 | >320 | >18.59 | >10.40 |
| Venezuelan equine encephalitis | Vero | 0.0 | >320 | 0.00 | 0.00 |

Note:
TI is the Therapeutic Index, i.e., TC/IC;
[a] μg/ml at 50% inhibition;
[b] μg/ml at 50% inhibition;
[c] 50% inhibition; d) 95% inhibition.

TABLE 2

CONFIRMATORY DATA ON EFFECT OF PALA ON FLAVI-, BUNYA- AND TOGAVIRUSES

| Virus | Cell Line | $IC_{50}$[a] | $TC_{50}$[b] | TI[c] | $TI_{(95)}$[d] |
|---|---|---|---|---|---|
| Punta toro | Vero | 18.4 | >320 | >17.35 | >10.00 |
| Sandfly fever | Vero | 14.9 | >320 | >21.54 | 0.00 |
| Yellow fever | Vero | 13.4 | >320 | >23.82 | >10.38 |
| Japanese encephalitis | Vero | 7.0 | >320 | >18.80 | 0.00 |
| Venezuelan equine encephalitis | Vero | None | >320 | 0.00 | 0.00 |

Note:
TI is the Therapeutic Index, i.e., TC/IC; a) μg/ml at 50% inhibition; b) μg/ml at 50% inhibition; c) 50% inhibition; d) 95% inhibition.

The results with PALA alone, in vitro, are unambiguous; PALA possesses broad spectrum antiviral activity against all of these RNA viruses (except VEE) at concentrations of about 10 to about 25 μg/ml, together with minimal toxicity in all systems examined, as evidenced by a $TC_{50}$ value of greater than about 320 μg/ml; thus, PALA has a therapeutic index (TI) of about 20 to about 30 against the great majority of viruses examined.

These studies when expanded to the DNA viruses and the other RNA viruses (positive and negative stranded viruses as well as retroviruses) demonstrated that three of four DNA-containing viruses were equally sensitive to inhibition by PALA. With the exception of herpes virus-1 and 2, in which no inhibitory activity was observed, PALA exerted activity against all of the above at a concentration of about 10 μg/ml. An RNA positive stranded virus, Coxsackie B3 required about 33 μg/ml for 50% inhibition as shown in Table 3; the therapeutic indices for most of these viruses was about 32.

TABLE 3

EFFECT of PALA on OTHER RNA & DNA VIRUSES

| Virus | Cell Line | $IC_{50}$[a] | $TC_{50}$[a] | TI[a] |
|---|---|---|---|---|
| Varicella | Vero | 10 | >320 | 32.0 |
| Herpes-1 | Vero | None | >320 | 0.0 |
| CMV | HFF* | 10 | >320 | 32.0 |
| Vaccinia | Vero | 10 | >320 | 32.0 |
| Paramyxo-3 | Hep-2 | 10 | >320 | 32.0 |
| Coxsackie B3 | Vero | 33 | >320 | 9.7 |
| LENTIVIRUS: HIV-1 | CEM | 12.0 | 60 | ~5.0 |

*Human Foreskin Fibroblast; a) 50% inhibition.

7. EXAMPLE 2

Using the duck hepatitis model (DHBV), primary duck hepatocyte cells were treated with various concentrations of PALA (disodium salt) and evaluated for cytopathic effect. In addition, viral DNA replication was assessed using "slot" dot blots. At concentrations of 40–50 μM, a 50% reduction in plaques was observed ($IC_{50}$); at high concentrations, i.e., 0.500 μM, there was a 95% inhibition, with little or no toxicity. These experiments were performed three times with confirmatory results.

8. EXAMPLE 3

The subsections below describe experiments in which African green monkeys were infected with simian varicella virus and treated with PALA, acyclovir or a combination thereof. The results demonstrate that PALA in combination with acyclovir decreased rash and minimally reduced viremia, especially at the end of the infections cycle. Some concentration dependent immunosuppression was noted at high concentrations. In addition, PALA showed an excellent synergistic effect with BV-araU (Bristol-Myers Squibb).

8.1 Materials and Methods

Fifteen African green monkeys were weighed and bled for clinical chemistry hematology baselines. These monkeys had previously been shown to have no antibody to simian varicella sf virus. Each of the 15 monkeys were infected with simian varicella virus by intratracheal inoculation of $3.7 \times 10^4$ plaque forming units (PFU) of simian varicella virus. The monkeys were divided into five groups of three monkeys each and assigned to treatment groups as indicated in Table 4. The protocol resulted in the following treatment groups. Control monkeys, service as infection controls, received twice daily intravenous injections of phosphate buffered saline administered at 1.0 ml/kg of body weight. A second group of three monkeys received PALA at 50 mg/kg/day given by intravenous bolus injection into the saphenous vein. A third group was given a lower dose of PALA at 20 mg/kg/day administered in a similar manner. Acyclovir treatment was administered at a subeffective dose of 10 mg/kg/day also given as intravenous bolus injection into the saphenous vein. A fifth group of three monkeys received a combined treatment of PALA at 20 mg/kg/day and acyclovir at 10 mg/kg/day. The drugs were injected into opposite veins at each time of treatment.

Drug solutions were prepared daily prior to treatment. Treatment was begun 24 hours after virus inoculation. PALA was provided as a solution in vials containing 5 ml at 100 mg/ml. The contents of three vials were pooled and seven ml of the pooled drug diluted to 28 ml to give 25 mg/ml. Five ml of this solution was diluted to 50 ml to give 10 mg/ml. Drug was administered twice daily resulting in total daily doses of 50 or 20 mg/kg/day.

Acyclovir received as a gift from Burroughs Wellcome was weighed out as a 200 mg quantity. This was diluted with 5 ml of PBS and pH adjusted to 11.0 with 1N NaOH to effect solution. This was subsequently diluted to 40 ml to give a solution of 5 mg/ml and sterilized by filtration. Again, 1 ml per kg of body weight was administered by intravenous injection twice daily resulting in a dose of 10 mg/kg/day.

The clinical course of simian varicella infection was followed by collection of 2 ml of blood in heparin on day 2, 5, 7, 9 and 11 post-inoculation. The lymphocytes in the 2 ml specimen were separated on ficol-hypaque gradients, washed twice in RPMI-1640 medium and suspended in 10 ml of this medium. The 10 ml volume was divided between two 25 cm² tissue culture flasks seeded 24 hours earlier with Vero cells. After 5–7 days incubation, the culture fluids were discarded from the flasks and the cell monolayer fixed with methanol and stained with methylene blue-basic fuchsin. When dried the number of plaques in each flask were counted and the mean number of plaques between the two paired flasks were determined and expressed as a quantitation of viremia per ml of blood.

Rash was evaluated daily using a subjective scoring of severity from ± to 4+. A ± score indicates less than 10 vesicles seen on the skin of the monkey while 4+ indicates numerous vesicles covering the majority of the body surface. General clinical condition was assessed daily and anorexia noted by counting the number of food biscuits consumed daily. Monkeys dying during the course of the experiment were necropsied and simian varicella was determined as the cause of death based on the typical pathology. Baseline hematology and clinical chemistry tests were performed at three days before virus inoculation and again on day 0, immediately before virus inoculation. Following inoculation of simian varicella virus blood was taken for hematology and clinical chemistry tests at 3, 7, 9 and 11 days.

At 14 and 21 days after virus inoculation, blood was taken and the serum separated for quantitation of antibody. Antibody titers were obtained in a serum neutralization test employing a plaque reduction assay. The antibody titer expressed is the dilution of serum resulting in an 80 percent reduction in the number of plaques from that number occurring in control cultures without added serum.

8.2 Results

Table 4 presents data relating to the daily scoring of the rash. Each of the three control monkeys developed rash with one monkey developing a maximum 4+ rash on day 11. This monkey died the following day with simian varicella involving the lungs and liver. The remaining two control monkeys developed maximum rash of 2+ and 3+ persisting for two days in each monkey. Two of the three monkeys treated with PALA at 50 mg/kg/day developed maximum 4+ rash. The third monkey only showed a 1+ rash on day 9 but died on day 10 with systemic simian varicella. The lower dose of PALA resulted in a 1+ rash in one monkey and a 2+ rash in the second monkey. The third monkey showed a 3+ rash on day 10 and died later that same day. Acyclovir at a subeffective dose of 10 mg/kg/day resulted in a moderately severe 3+ rash in two monkeys and mild 1+ rash in a third monkey. The combination at 10 mg/day appeared to moderate the rash with only ± scores seen on most of the days with a maximum 1+ score in a single monkey.

Viremia was severe in one control monkey (>1000 PFU/ml of blood) and moderate (100–300 PFU/ml of blood) in the other two control monkeys (Table 3). In the monkeys receiving PALA at 50 mg/kg/day, one monkey had a severe viremia and died, a second had a moderately severe viremia (300–800 PFU/ml) while a third had a moderate viremia. Similar results were seen in the monkeys treated with 20 mg/kg/day of PALA. Acyclovir at 10 mg/kg/day was found to have no effect in moderating viremia. Two monkeys had severe viremia and one monkey presented with moderately severe viremia. A slight benefit of the combined treatment with PALA and acyclovir was seen. One monkey had a moderately severe viremia, one a moderate viremia and a third minimal viremia.

Hematology tests showed no consistent pattern of abnormal values. Thrombocytopenia was seen on day 11 in one monkey (M636) treated with PALA at 50 mg/kg/day and in two monkeys (M642 and M639) treated with acyclovir. Chemistry values did reflect the hepatitis present as a consequence of simian varicella virus. No abnormalities were seen resulting from treatment with the drugs at the doses employed.

Titers of serum neutralizing antibody were comparable in the monkeys in the control groups and in the monkeys treated with both doses of PALA or with acyclovir. The monkeys treated with the combination of PALA and acyclovir did show lower titers of antibody to simian varicella virus when compared to the titers in the other monkeys. It is likely that this reflects the effects of inhibition of virus replication by the combination therapy.

TABLE 6

Effect of Treatment with PALA and Acyclovir Upon Serum Neutralizing Antibody Titers to Simian Varicella Virus

| Treatment Group | Monkey Number | Serum Neutralizing Antibody Titer - Days P.I. | |
|---|---|---|---|
| | | 14 Days | 21 Days |
| Control | M644 | Dead | Dead- |
| | M634 | 1:640 | 1:1280 |
| | M647 | 1:320 | 1:1280 |
| PALA: 50 mg/kg/day | M646 | Dead | Dead |
| | M636 | 1:80 | 1:1280 |
| | M635 | 1:320 | ≧1:1280 |
| PALA: 20 mg/kg/day | M633 | Dead | Dead |
| | M637 | 1:640 | ≧1:1280 |

TABLE 4

Effect of PALA and Acyclovir in Combination Treatment of Simian Varicella Virus: Rash

| Treatment Group | Monkey Number | Severity of Rash - Days Post-Infection | | | | | | | | |
|---|---|---|---|---|---|---|---|---|---|---|
| | | 7 | 8 | 9 | 10 | 11 | 12 | 13 | 14 | 16 |
| Control PBS | M644 | – | – | 1+ | 3+ | 4+ | Dead | | | |
| | M634 | – | ± | 2+ | 2+ | 1+ | ± | – | – | – |
| | M647 | ± | 1+ | 2+ | 3+ | 3+ | 1+ | ± | ± | ± |
| PALA: 50 mg/kg/d | M646 | – | ± | 1+ | Dead | | | | | |
| | M636 | – | 1+ | 2+ | 2+ | 2+ | 3+ | 4+ | 4+ | 3+ |
| | M635 | – | – | 2+ | 2+ | 2+ | 3+ | 4+ | 4+ | 3+ |
| PALA: 20 mg/kg/d | M633 | – | 1+ | 2+ | 3+ | Dead | | | | |
| | M637 | – | – | – | – | 1+ | 2+ | 2+ | 2+ | – |
| | M638 | – | – | ± | 1+ | 1+ | 1+ | 1+ | 1+ | – |
| Acyclovir: 10 mg/kg/d | M642 | – | ± | ± | 1+ | 1+ | ± | ± | ± | – |
| | M639 | 1+ | 1+ | 1+ | 2+ | 3+ | 3+ | 3+ | 2+ | 1+ |
| | M643 | 1+ | 2+ | 2+ | 3+ | 2+ | 2+ | 1+ | 1+ | ± |
| PALA: 20 mg/kg/d +Acyclovir: 10 mg/kg/d | M640 | – | – | – | ± | 1+ | ± | – | – | – |
| | M645 | – | – | ± | ± | ± | ± | ± | ± | – |
| | M641 | – | – | ± | ± | ± | ± | – | – | – |

Treatment given by i.v. injection twice daily as divided doses beginning 24 hours after virus inoculation.

TABLE 5

Effect of PALA and Acyclovir in Combination Treatment of Simian Varicella Virus: Viremia

| Treatment Group | Monkey Number | Mean PFU on Days Post-Infection | | | | |
|---|---|---|---|---|---|---|
| | | 3 | 5 | 7 | 9 | 11 |
| Control PBS | M644 | 6 | 105 | >1000 | >1000 | Dead |
| | M634 | 16 | 138 | 51 | 0 | 0 |
| | M647 | 19 | 181 | 233 | 0 | 0 |
| PALA: 50 mg/kg/d | M646 | 1 | 136 | >1000 | >1000 | Dead |
| | M636 | 7 | 154 | 508 | 89 | 2 |
| | M635 | 7 | 148 | 213 | 10 | 0 |
| PALA: 20 mg/kg/d | M633 | 13 | 195 | >1000 | >100 | Dead |
| | M637 | 9 | 130 | 173 | 4 | 0 |
| | M638 | 5 | 79 | 305 | 7 | 0 |
| Acyclovir: 10 mg/kg/d | M642 | 9 | 342 | >1000 | 322 | 0 |
| | M639 | 2 | 90 | >1000 | 706 | 0 |
| | M643 | 5 | 210 | 504 | 0 | 0 |
| PALA: 20 mg/kg/d +Acyclovir: 10 mg/kg/d | M640 | 0 | 8 | 161 | 13 | 0 |
| | M645 | 12 | 113 | 550 | 11 | 0 |
| | M641 | 7 | 48 | 30 | 0 | 0 |

Treatment given by i.v. injection twice daily as divided doses beginning 24 hours after virus inoculation.

TABLE 6-continued

Effect of Treatment with PALA and Acyclovir Upon Serum Neutralizing Antibody Titers to Simian Varicella Virus

| Treatment Group | Monkey Number | Serum Neutralizing Antibody Titer - Days P.I. | |
|---|---|---|---|
| | | 14 Days | 21 Days |
| | M638 | 1:160 | 1:320 |
| Acyclovir: 10 mg/kg/day | M642 | 1:640 | 1:640 |
| | M639 | 1:160 | 1:1280 |
| | M643 | 1:160 | 1:160 |
| PALA: 20 mg/kg/day +Acyclovir: 10 mg/kg/day | M640 | 1:80 | 1:640 |
| | M645 | 1:20 | 1:320 |
| | M641 | 1:80 | 1:640 |

Titer expressed as the dilution of serum resulting in a reduction in the number of viral plaques by 80 percent or more from the number appearing in control cultures.

9. EXAMPLE 4

In vitro drug efficacy during AD169 infection on Hs68 cell monolayers.

These experiments were performed to confirm the in vitro efficacy of the PALA at a concentration of 10 μg/ml during HCMV infection. In vitro infection on Hs68 cell monolayers and efficacy evaluations were performed for the following HCMV virus isolates: [1] AD169, a standard laboratory cytomegalovirus strain; 2] a DHPG resistant HCMV isolate (Thymidine kinase resistant DHPG; $ED_{50}=>55$ µg) and [3] a recently obtained HCMV clinical isolate. This study also evaluated the reduction in HCMV titers during active suppression with the experimental drug and with DHPG.

These subsections demonstrate that all three strains: CMV laboratory strain, the human isolate of HCMV and the DHPG resistant strain were sensitive to PALA with viral yield reduction of 2–3 $\log_{10}$.

9.1 Methods $10^4$ PFU/ml HCMV of either: [1] strain AD 169; [2] DHPG resistant HCMV; or [3] the recently isolated clinical HCMV strain characterized as described above was inoculated onto confluent Hs68 cell monolayers (35 mm culture dishes) and adsorbed to the monolayers for 1 hour at 37° C. The inoculum was aspirated and medium containing the experimental drug or DHPG, or no drug in the medium was added to the HCMV-inoculated monolayer. Medium containing the appropriate drug additives was changed daily. At 24 hour intervals, from day 1 through day 7 PI, the HCMV-inoculated drug-treated monolayers were handled as follows: The supernatant containing cell-free virus was removed from the cells and the titer of HCMV cell-free virus in the supernatant was determined by standard plaque assay. The cell monolayer was washed with HBSS to remove residual drug, and the cells harvested by scraping. The cells were sonicated and centrifuged to pellet cell debris. The titer of the cell-free HCMV released from the infected cell monolayer was determined. The efficacy of the drug was represented as reduction in HCMV PFU/ml compared to non-drug-treated HCMV PFU/ml and to DHPG HCMV inhibition.

9.2 Results

9.2.1 AD169 Infected Hs68 Cell Monolayers

Figure 2:
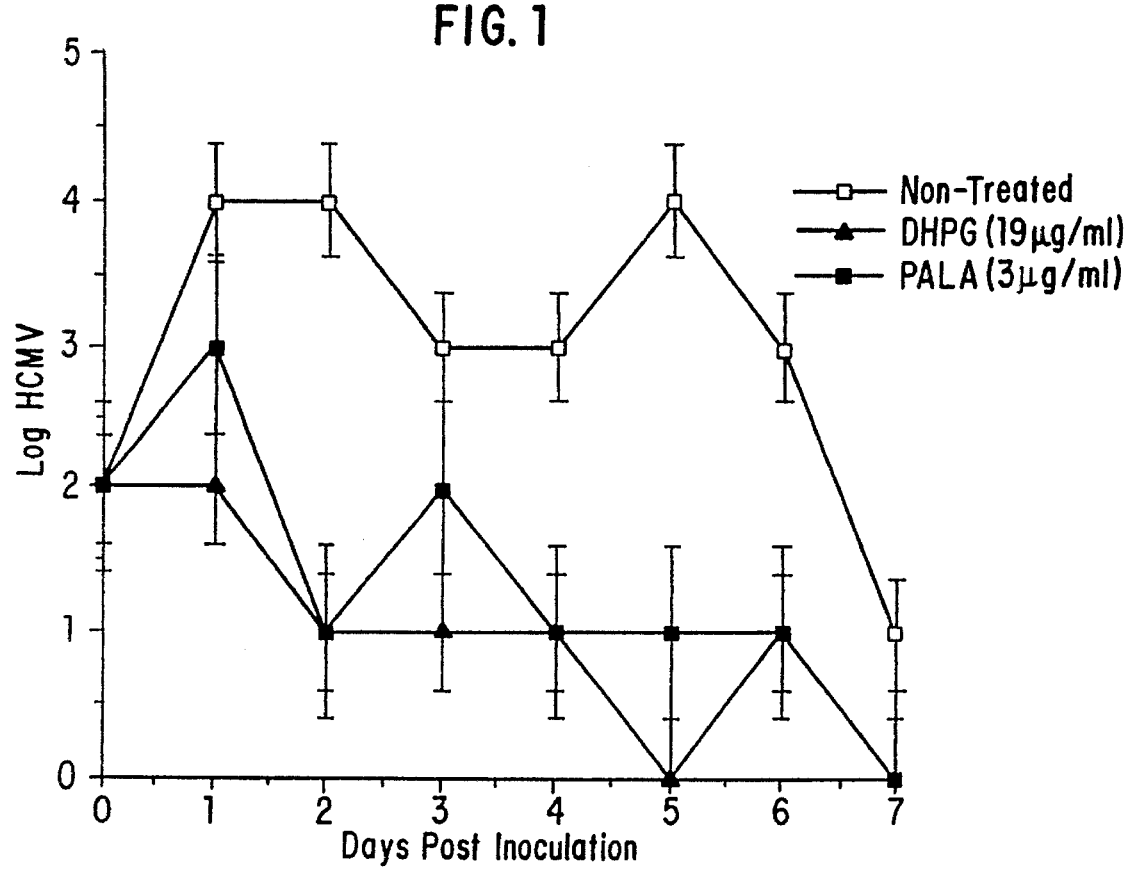
FIG. 2 is a graph of AD 169 cell associated HCMV titers recovered from sonicated cell pellets after incubation with DHPG, PALA or placebo.

PALA used at a concentration of 3 µg/ml was effective in reducing HCMV titers when compared to placebo treated controls. When the PALA was compared to DHPG in vitro therapy (19 µg/ml; ED50 for AD 169), the reduction in HCMV titers was similar to the DHPG treated monolayers, but, titers remained slightly higher than the DHPG titers. The HCMV titer reduction after therapy with the PALA was similar for the supernatant (cell free HCMV) and for the cell pellet (cell associated HCMV titer). A rebound (currently unexplained) in HCMV titers from the cell supernatant and from the cell pellet assays was evident on day 3 PI. The titers remained elevated when compared to DHPG on days 4 and 5 PI. No samples were processed after day 5 due to the loss of cells from the monolayer. By day 5 PI, approximately 50% of the monolayer in the drug treated samples had been lost. HCMV titers are presented in Table 7a and FIGS. 1 and 2.

9.2.2 Clinical HCMV Isolate

Figure 3:
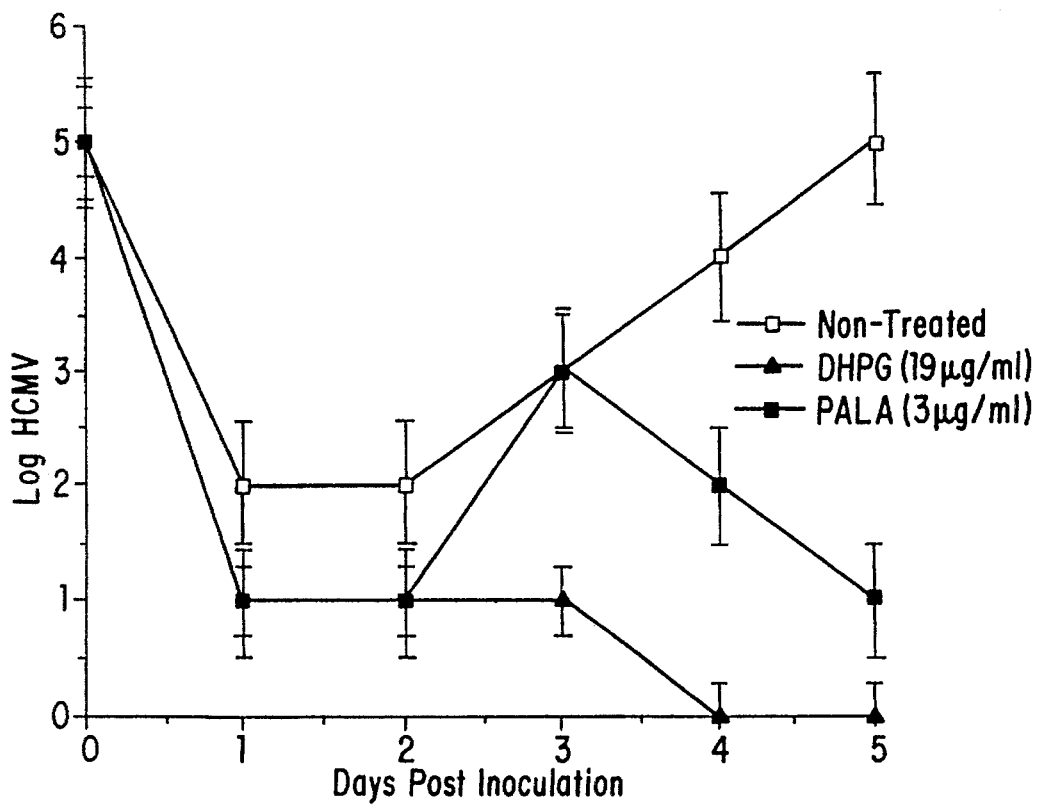
FIG. 3 is a graph of HCMV clinical isolate titers recovered from supernatant assay after incubation with DHPG, PALA or placebo.
Figure 4:
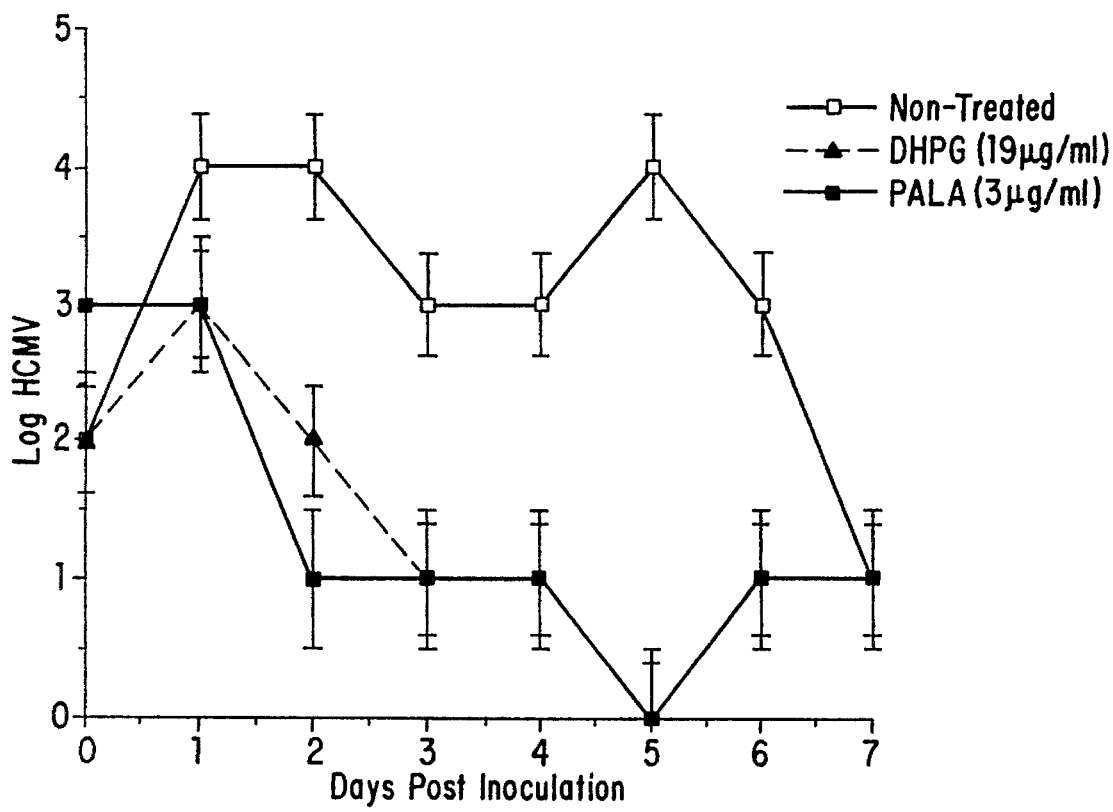
FIG. 4 is a graph of HCMV cell associated clinical isolate titers recovered from sonicated cell pellets after incubation with DHPG, PALA or placebo.

A clinical isolate was obtained from a confirmed case of HCMV neonatal infection. The virus was confirmed as HCMV by neutralization. PALA and DHPG were effective in reducing the titer of this clinical isolate of HCMV. There was no difference between these two therapies and their effect on reducing HCMV titer. HCMV titers are presented in Table 7b and in FIGS. 3 and 4.

9.2.3 DHPG Resistant HCMV

Figure 5:
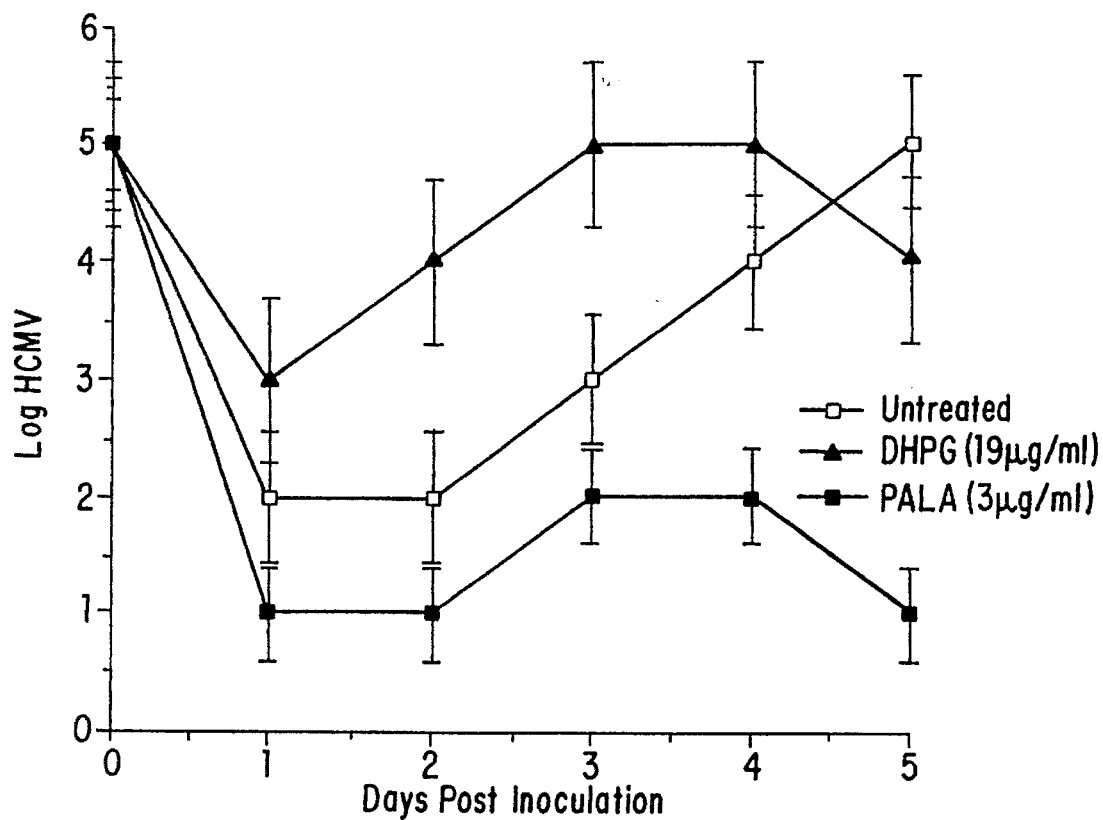
FIG. 5 is a graph of HCMV DHPG resistant isolate titers recovered from supernatant assays after incubation with DHPG, PALA or placebo.
Figure 6:
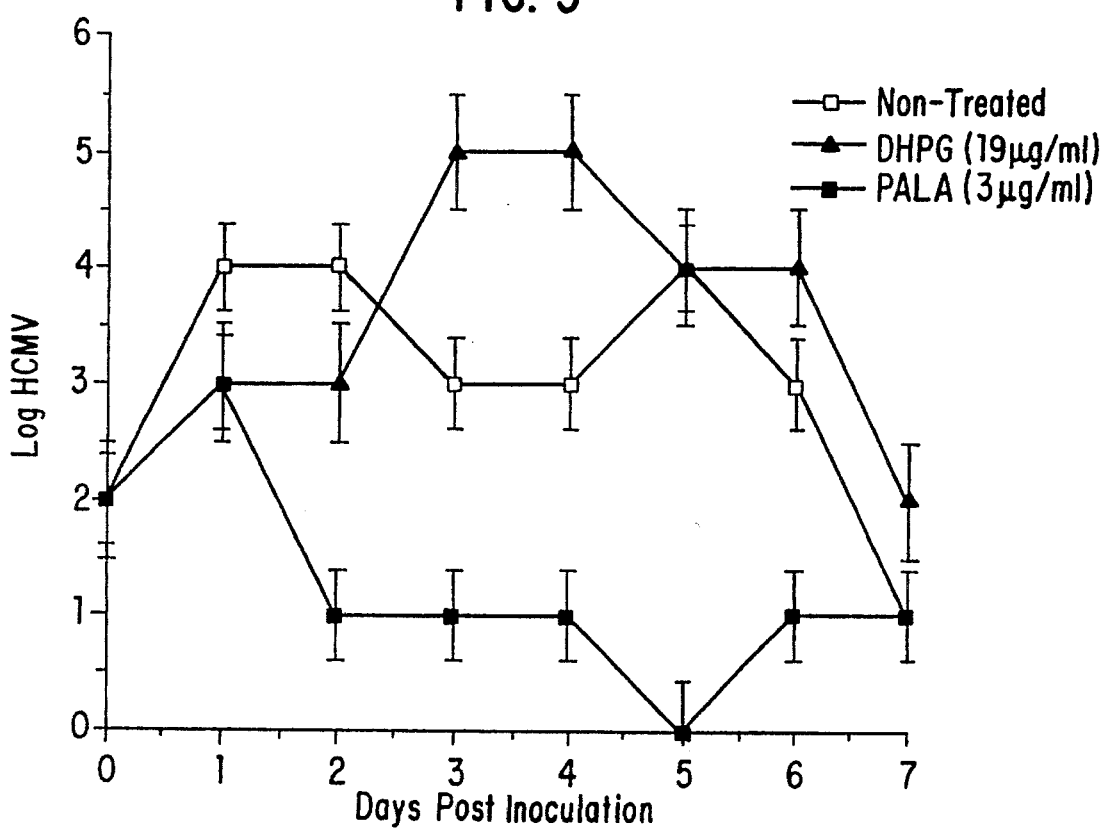
FIG. 6 is a graph of HCMV cell associated DHPG resistant virus titers recovered from sonicated cell pellets after incubation with DHPG, PALA or placebo.

A DHPG resistant HCMV isolate (characterized previously as a DHPG resistant isolate by in vitro decreases in DHPG sensitivity; the virus has altered thymidine kinase activity) was used in these in vitro assays. DHPG was not effective in reducing the titer of HCMV in either the cell associated or cell free assays. The titer of DHPG resistant HCMV in the DHPG treated group was the same as or higher than the placebo treated monolayers (Not statistically significant). PALA was effective in reducing the DHPG resistant HCMV titer. By days 4–5 PI, the PALA treated monolayers had significantly lowered HCMV titers than DHPG treated or placebo treated monolayers. HCMV titers are presented in FIGS. 5 and 6.

TABLE 7a

Cell free (supernatant) HCMV Titers after incubation with DHPG, PALA and placebo.

| Days PI | Control | DHPG | | | PALA | | |
| --- | --- | --- | --- | --- | --- | --- | --- |
| | | AD 169 | $DHPG^R$ | Clin Isolate | AD169 | $DHPG^R$ | Clin Isolate |
| 0 | $10^5$ | $10^5$ | $10^5$ | $10^5$ | $10^5$ | $10^5$ | $10^5$ |
| 1 | $10^2$ | $10^1$ | $10^3$ | $10^1$ | $10^1$ | $10^1$ | $10^2$ |
| 2 | $10^2$ | $10^1$ | $10^4$ | $10^1$ | $10^1$ | $10^1$ | $10^1$ |
| 3 | $10^3$ | $10^1$ | $10^5$ | $10^1$ | $10^3$ | $10^2$ | $10^2$ |
| 4 | $10^4$ | 0 | $10^5$ | $10^1$ | $10^2$ | $10^2$ | $10^1$ |
| 5 | $10^5$ | 0 | $10^4$ | 0 | $10^1$ | $10^1$ | $10^1$ |

TABLE 7b

Cell Associated (cell pellet sonicate) HCMV Titers after incubation with DHPG, PALA and placebo.

| Days PI | Control | DHPG | | | PALA | | |
| --- | --- | --- | --- | --- | --- | --- | --- |
| | | AD 169 | $DHPG^R$ | Clin Isolate | AD159 | $DHPG^R$ | Clin Isolate |
| 0 | $10^2$ | $10^2$ | $10^2$ | $10^2$ | $10^2$ | $10^2$ | $10^2$ |
| 1 | $10^4$ | $10^2$ | $10^3$ | $10^3$ | $10^3$ | $10^3$ | $10^3$ |
| 2 | $10^4$ | $10^1$ | $10^3$ | $10^2$ | $10^1$ | $10^1$ | $10^2$ |
| 3 | $10^3$ | $10^1$ | $10^5$ | $10^1$ | $10^1$ | $10^1$ | $10^1$ |
| 4 | $10^3$ | $10^1$ | $10^5$ | $10^1$ | $10^1$ | $10^1$ | $10^1$ |
| 5 | $10^4$ | 0 | $10^4$ | 0 | $10^1$ | 0 | 0 |
| 6 | $10^3$ | $10^1$ | $10^4$ | $10^1$ | $10^1$ | $10^1$ | $10^1$ |
| 7 | $10^1$ | 0 | $10^2$ | $10^1$ | 0 | $10^1$ | $10^1$ |

10. EXAMPLE 5

Ascending dose and frequency efficacy evaluation of single- and combination-agent PALA and DHPG (ganciclovir) in the rabbit model of HCMV chorioretinitis.

These studies were performed to evaluate the efficacy of single and combination-agent PALA and DHPG during intravenous therapy in an ascending dose concentration and frequency study by comparing clinical, virus recovery and histopathological HCMV-induced disease severity. Two concentrations of the experimental drug, 20 and 50 mg/kg were evaluated at 2 different administration frequencies, daily and every other day from day 1 PI through day 10 PI. In vivo efficacy of the—experimental drug was compared to intravenous DHPG therapy. The results demonstrated that an intravenous efficacy rating of Combination-agent low dose PALA plus low dose DHPG therapy (Group #6) >>Single-agent DHPG (Group #7) >>Control (Group #8)=Single-agent high (Groups #1 and #2) and low (Group #3) dose PALA >>Combination-agent high dose PALA plus low dose DHPG (Group #5) >>Combination-agent high dose PALA plus low dose DHPG (Group #4).

10.1 Methods

A total of 32 pigmented rabbits were used in this study. Animals were evaluated by slit lamp and indirect ophthalmoscopy to determine normal ocular morphology and lack of preexisting pathology. Animals were handled as follows:

[1] On day 0, all rabbits were inoculated by mid-vitreal injection of $10^5$ PFU HCMV strain AD 169 in 100 μl.

[2] Animals were maintained in individual cages and developing chorioretinal HCMV disease was monitored daily. On day 2 PI, HCMV-inoculated animals were divided into 8 groups of 4 rabbits each with matched chorioretinal disease scores. The HCMV-infected rabbits received intravenous therapy as indicated below:

Group #1—4 animals, intravenous injection of high dose experimental drug (50 mg/kg) daily from day 2 through 10 PI. A total of 9 IV injections.

Group #3—4 animals, intravenous injection of low dose experimental drug (20 mg/kg) daily from day 2 through 10 PI. A total of 9 IV injections.

Group #4—4 animals, intravenous injection of high dose experimental drug (50 mg/kg) daily from day 2 through 10 PI (a total of 9 IV injections) plus high dose DHPG 10 mg/kg/day in 2 divided doses from day 2 through 10 PI (a total of 18 IV injections).

Group #5—4 animals, intravenous injection of high dose experimental drug (50 mg/kg) daily from day 2 through 10 PI (a total of 9 IV injections) plus low dose DHPG 5 mg/kg/day in 2 divided doses from day 2 through 10 PI (a total of 18 IV injections).

Group #6—4 animals, intravenous injection of low dose experimental drug (20 mg/kg) daily from day 2 through 10 PI (a total of 9 IV injections) plus low dose DHPG 5 mg/kg/day in 2 divided doses from day 2 through 10 PI (a total of 18 IV injections).

Group #7—4 animals, intravenous injection of DHPG 10 mg/kg/day in 2 divided doses from day 2 through day 10 PI. A total of 18 IV injections.

Group #8—4 animals, intravenous injection of sterile saline on days 2 through 10 PI.

[3] All animals received daily indirect ophthalmoscopic examinations to evaluate clinical HCMV disease progression (From days 2 through 10 PI). The indirect ophthalmoscopic examinations were performed independently by two readers who were masked as to the therapy that the rabbits were receiving.

[4] All animals were sacrificed on day 12 PI. Chorioretina and iris tissues and vitreous samples will be removed and processed for HCMV recovery by cell sonicate assay on Hs68 cell monolayers. Selected ocular and lung tissue samples were processed for histochemistry to evaluate HCMV-induced ocular pathology in treated and non-treated groups.

The clinical, virus recovery and histological efficacy results for all drug-treated intravenous therapy groups were correlated with each other and with the placebo therapy group.

10.2 Results

Single-Agent Intravenous Therapy Groups

Figure 7:
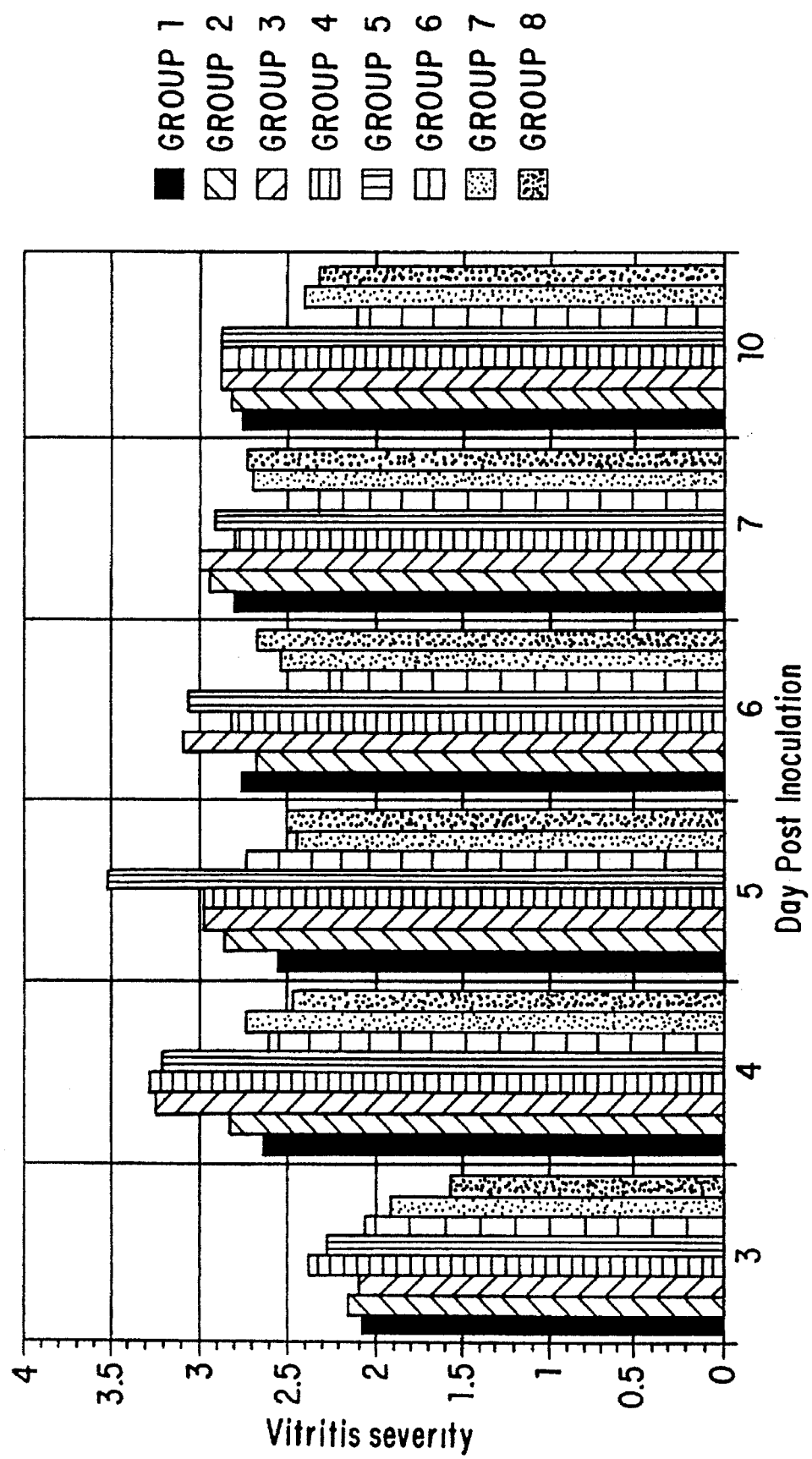
FIG. 7 is a bar graph of the vitreitis severity found in the animals of Example 5, infra.

FIG. 7 summarizes data on the efficacy of single-agent and combination agent intravenous therapy during HCMV-induced chorioretinal disease in the rabbit. Summaries of individual therapies follow.

Group #1: High dose PALA (50 mg/kg) IV daily single-agent therapy from day 2 through 10 PI.

Single-dose daily intravenous administration of PALA at a concentration of 50 mg/kg was only marginally effective in reducing the development of disease in the HCMV inoculated animals. Vitreitis developed to moderate levels within 3–4 days post inoculation. The further progression of vitreitis hindered the comprehensive evaluation of chorioretinal disease in these animals and consequently, the histological evaluations will become more important in determining the extent of chorioretinal disease and single-agent efficacy of the PALA formulation. Optic nerve head edema and redness (clinical signs of HCMV infection in this rabbit model) were present on days 3 through 7 PI. By the conclusion of the study, in animals where the fundus was partially visible, inflammation and redness of the optic nerve head was decreasing. Although the view of the fundus and developing HCMV chorioretinal disease was obscured by the degree of vitreitis in these animals, the clinical impression in these high dose PALA treated animals was that the therapy was only minimally effective and the development and progression of HCMV-induced chorioretinal disease was not stopped by this high dose single-agent therapy.

Preliminary evaluation of histology demonstrated moderate areas of chorioretinal HCMV disease restricted to the inner retina. Occasionally, the HCMV infection involved larger areas of the chorioretina in disseminated disease. Edema and vascular congestion of the choroid was prominent at moderate levels. The areas of HCMV-induced disease in these PALA treated eyes were focal to geographic, indicating a moderate chorioretinal infection. The areas of immune cell involvement consisted of monocytic and polymorphonuclear cell infiltrates. These preliminary histological evaluations confirm the clinical disease impressions. At sacrifice, the lungs appeared clear and non congested. Samples have been processed for routine histology and results are pending.

No HCMV was recovered from any chorioretinal cell sonicate co-culture on day 12 PI. The lack of HCMV recovery may be (and probably is) directly related to the time point selected for HCMV recovery, i.e., day 12 post inoculation. To evaluate more fully the efficacy of these single-agent therapies, a time course sacrifice of animals throughout the course of therapy would be necessary. (In non-treated eyes, HCMV is present usually up to day 8 or 9 PI. Recovery after day 9 or 10 PI is variable).

Group #2: High dose PALA (50 mg/kg) IV every other day single-agent therapy from day 2 through 10 PI.

Single-dose intravenous administration of PALA at a concentration of 50 mg/kg every other day was marginally effective in reducing the development of disease in the HCMV inoculated animals. Disease development in animals treated with this concentration of PALA was similar to the HCMV disease progression in the 50 mg/kg daily IV therapy group. Vitreitis developed to moderate to severe levels within 3–4 days post inoculation. The progression of vitreitis hindered the comprehensive evaluation of chorioretinal disease in these animals and consequently, the histological evaluations will become more important in determining the extent of chorioretinal disease and single-agent efficacy of the PALA formulation. Optic nerve head edema and redness (clinical signs of HCMV infection in this rabbit model) were severe on days 3–4 PI and could not be evaluated on days 5 through 7 PI, indicating progressive HCMV disease in the eye despite therapy. Although the view of the fundus and developing HCMV chorioretinal disease was obscured by the degree of vitreitis in these animals, the clinical impression of HCMV-induced disease in these high dose every other day PALA treated animals was that this therapeutic regimen was not effective in reducing the development of HCMV disease. The development of HCMV-induced disease in these two high dose PALA therapy groups was not different from each other. (FIG. 7) At sacrifice, the lungs appeared clear and non congested.

No HCMV was recovered from any chorioretinal cell sonicate co-culture on day 12 PI. The lack of HCMV recovery may be (and probably is) directly related to the time point selected for HCMV recovery.

Group #3: Low-dose PALA (20 mg/kg) IV daily single-agent therapy from day 2 through 10 PI.

Single-agent intravenous administration of PALA at a concentration of 20 mg/kg every other day was not effective in reducing the development of disease in the HCMV inoculated animals compared to other therapy groups and to placebo therapy. The disease progression was similar to that reported for Group #2.

Preliminary histological results indicate diffuse disease with moderate to severe chorioretinal disease.

No HCMV was recovered from any chorioretinal cell sonicate co-culture on day 12 PI. The lack of HCMV recovery may be directly related to the time point selected for HCMV recovery.

Group #7: HCMV-inoculated DHPG IV treated animals (10 mg/kg/day in 2 divided doses) from days 2 through 10 PI—

DHPG was used in this experiment as the control therapy. Animals received DHPG therapy beginning day 2 post inoculation and continuing through day 10 post inoculation. The 10 mg/kg/day DHPG therapy in two divided doses did reduce the development of HCMV chorioretinal infection and disease. By day 6–7 PI, in 70% of the DHPG treated eyes, the average involvement of HCMV chorioretinal disease had stabilized and the disease had begun to resolve by day 8 PI. Although the fundus view was partially obscured by the development of vitreitis, the chorioretinal disease remained predominantly focal with moderate involvement of the optic nerve head in inflammation. The choroid remained congested through day 10 PI. Vitreitis in these animals remained at moderate levels from day 4 through day 10 PI. The clinical impression of disease in these treated eyes was that this DHPG single agent therapy group was the most improved of all therapy groups. Throughout the study, the DHPG therapy group had consistently lower vitreitis (indirectly chorioretinal disease involvement) than the three PALA single-agent therapies. Because of the development of moderate to severe vitreitis in this therapy group, statistical comparisons to the placebo treated group are not possible (control and DHPG treated groups were of similar vitreitis involvements. At sacrifice, the lungs appeared normal. Samples have been processed for routine histology and results are pending.

No HCMV was recovered from any chorioretinal cell sonicate co-culture on day 12 PI. The lack of HCMV recovery may be (and probably is) directly related to the time point selected for HCMV recovery.

Group #8: HCMV-inoculated Placebo-treated (Placebo+ EDTA) animals—

Placebo treated animals received daily single injections of sterile saline +EDTA beginning on day 2 PI and continuing through day 10 PI. Placebo treated eyes had developed mild chorioretinal and vitreous disease by day 2 PI. The disease consisted of focal areas of retinal infiltration, optic nerve inflammation and redness and mild vitreitis. The vitreitis consisted of vitreous strands and peripheral cellular infiltrates and cloudiness. Placebo therapy did not arrest the development of chorioretinal disease and vitreitis in these animals. Chorioretinal disease increased and the developing vitreitis in these HCMV infected eyes developed to severe levels by day 3–4 PI interfering with comprehensive evaluation of chorioretinal disease. After day 5 PI, the vitreitis obscured comprehensive evaluation of retinal and choroidal disease.

Preliminary histological evaluation of placebo-treated eyes demonstrated that HCMV infection had progressed from the inner retinal areas to involve the photoreceptor layer. Histology demonstrated areas of retinal edema, mixed cellular infiltration and occasional retinal detachment. Areas of extensive retinal HCMV disease involvement were next to areas of normal retina. Histology demonstrated moderate to extensive involvement of the choroid and retina. At sacrifice, lung observation demonstrated mild to moderate opacification and hemorrhage in 2 rabbits. A mild to moderate edema (congestion) was also present.

No HCMV was recovered from any chorioretinal cell sonicate co-culture on day 12 PI. The lack of HCMV recovery may be (and probably is) directly related to the time point selected for HCMV recovery.

COMBINATION-AGENT PALA and DHPG INTRAVENOUS THERAPY:

Group #4: High dose PALA (50 mg/kg) daily IV therapy from day 2 through 10, plus IV high dose DHPG (10 mg/kg/day in 2 divided doses on days 2 through 10 PI). and Group #5: High dose PALA (50 mg/kg) daily IV therapy from day 2 through 10, plus IV low dose DHPG (5 mg/kg/day in 2 divided doses on days 2 through 10 PI).

Combination intravenous therapy with daily high dose PALA (50 mg/kg) and daily DHPG (10 mg/kg) [Group #4] or with high dose PALA (50 mg/kg) plus DHPG (5 mg/kg in two divided doses) from days 2 through 10 post inoculation was not effective in reducing the development of HCMV induced chorioretinal disease. In fact, the vitreitis (indirect measurement of HCMV disease) in these combination therapy groups was more severe than the disease in the single-agent therapy, combination-agent therapy or placebo therapy groups. The increase in severity of HCMV-induced disease may be interpreted as an antagonism of the two compounds. Specifically the antagonism of the 50 mg/kg PALA and DHPG at either 10 or 5 mg/kg. Prior to vitreitis development that obscured visualization of the fundus, the optic nerve head was exhibiting redness and inflammatory changes characteristic of the HCMV-induced disease. On day 10 PI, the optic nerve head alterations had not decreased in those animals where the nerve head was visible. Based upon the clinical impression of HCMV-induced disease in these high dose PALA combination treated eyes, the combination therapy resulted in disease that was more severe than placebo or disease in single-agent therapy groups. Although only 8 eyes were evaluated/high-dose PALA combination therapy group, the combinations appear to be antagonistic, i.e., disease in the combination groups was more severe than the 50 mg/kg USNUS08 or 10 mg/kg DHPG single-agent therapy groups. Lung involvement was not evident at sacrifice. Selected samples are being processed for histology.

No HCMV was recovered from any chorioretinal cell sonicate co-culture on day 12 PI. The lack of HCMV recovery may be (and probably is) directly related to the time point selected for HCMV recovery.

Group #6: Low dose PALA (20 mg/kg) daily IV therapy from day 2 through 10, plus low dose IV DHPG (5 mg/kg/day in 2 divided doses on days 2 through 10 PI).

Combination intravenous therapy with daily low dose PALA (20 mg/kg) and daily low dose DHPG (5 mg/kg) [Group #6] was the most effective combination-agent therapy. This combination was more effective in reducing the vitreitis and optic nerve head changes than any other single-agent or combination-agent therapeutic regimen evaluated. This combination-agent therapy was superior to all other therapies throughout the course of the therapy (day 2 through 10 post inoculation). In fact, the vitreitis (indirect measurement of HCMV disease) in this combination therapy group was less severe than in any other single-agent therapy, combination-agent therapy or placebo therapy group. The decrease in severity of HCMV-induced disease may be interpreted as an additivity of the two compounds (additional samples will need to be evaluated before this conclusion can be supported by statistical analysis). Prior to vitreitis development that obscured visualization of the fundus, the optic nerve head was exhibiting moderate redness and inflammatory changes characteristic of the HCMV-induced disease. On day 10 PI, the optic nerve head alterations had decreased in those animals where the nerve head was visible. Based upon the clinical impression of HCMV-induced disease in these low dose PALA combination treated eyes, the combination therapy resulted in disease that was less severe than disease in placebo treated or disease in single-agent therapy groups. Lung involvement was not evident at sacrifice.

No HCMV was recovered from any chorioretinal cell sonicate co-culture on day 12 PI. The lack of HCMV recovery may be (and probably is) directly related to the time point selected for HCMV recovery.

10.3 Conclusion

[1] PALA when used as single-agent high dose or low dose therapy during HCMV-induced infection in the rabbit was not effective in reducing the development and progression of ocular disease (based upon vitreitis and optic nerve head HCMV-induced changes).

[2] DHPG used as a single-agent therapy was effective in reducing the severity of HCMV-induced chorioretinal disease in the rabbit.

[3] Combination-agent therapy involving HIGH dose PALA were not effective in reducing ocular HCMV-induced disease progression. In fact, these high dose combination therapies demonstrated an antagonistic antiviral effect resulting in HCMV-induced ocular disease severity that was more severe than disease observed in other single- and combination-agent therapy groups.

[4] The combination-agent therapy using intravenous low dose PALA and low dose DHPG was effective in reducing the development and severity of HCMV-induced disease in this model. This combination-agent therapy regimen is demonstrating an additive or synergistic anti-HCMV effect.

[5] PALA alone or in combination with DHPG prevented interstitial pneumonitis; thus PALA may be useful as a single agent therapy for related disorders.

11. EXAMPLE 6

PALA efficacy evaluation in the rabbit: confirmation of clinical single-and combination-agent efficacy with critical analysis of reductions in HCMV titers in the chorioretina on post therapy days 3, 4, 5, and 6.

These experiments were performed to confirm the efficacy of the PALA during intravenous therapy after HCMV infection in the rabbit model by comparing clinical, and histopathological HCMV-induced disease severity. PALA intravenous therapy was evaluated by HCMV recovery during therapy. HCMV titers from chorioretinal sonicate co-cultures were compared to DHPG and placebo recovery titers. High dose PALA therapy was evaluated as a single agent and as a combination agent therapy in conjunction with DHPG.

11.1 Methods

A total of 41 pigmented rabbits were used in this study. Animals were evaluated by slit lamp and indirect ophthalmoscopy to determine normal ocular morphology and lack of pre-existing pathology. Animals were handled as follows:

[1] On day 0, all animals were evaluated by ophthalmoscopy to insure that all posterior segments were normal. Following the fundus examination, animals received topical eyedrops to dilate the pupils. The topical eye drop therapy continued daily throughout the course of the study.

[2] On day 0, all rabbits were inoculated by mid-vitreal injection of $10^5$ PFU HCMV strain AD 169 in 100 μl. Other rabbits were sham-inoculated with non-infected Hs68 cell monolayer supernatant. These sham-inoculated animals were controls for the IV therapy groups.

[3] Animals were maintained in individual cages and developing chorioretinal HCMV disease was monitored daily. On day 2 PI, HCMV-inoculated animals were divided into groups of 4–6 HCMV-inoculated rabbits plus 1 sham-inoculated rabbit. The HCMV-infected and sham-inoculated rabbits received intravenous therapy as indicated below:

Single-agent PALA intravenous therapy daily

Group #1: 4 HCMV-inoculated and 1 sham-inoculated animal, intravenous injection of high dose PALA (50 mg/kg) on days 2 through 10 PI. A total of 9 IV injections.

Animals in this group were sacrificed in a time course study on day 3, 4, 5 and 6 PI to evaluate reductions in HCMV recovery and titer. Eyes were removed and processed for cell-sonicate recovery of HCMV. The sham-inoculated animal was sacrificed on day 12 PI, and used to evaluate the toxic effects of PALA on the retina and choroid after intravenous administration.

Combination-agent PALA and DHPG intravenous therapy: titer determinations and clinical efficacy validation.

Group #2: 7 HCMV-inoculated and 1 sham-inoculated animal, intravenous injection of high dose PALA (50 mg/kg) on days 2 through 10 PI (A total of 9 IV injections) plus high dose DHPG 10 mg/kg/day in 2 divided doses from day 2 through 10 PI (a total of 18 IV injections).

One animal from this therapy group was sacrificed on days 3, 4, 5, and 6 PI. The eyes were enucleated and processed for HCMV recovery by cell sonicate recovery to determine the presence of HCMV and the titer of virus in the chorioretina. The remaining 2 HCMV-infected and 1 sham inoculated rabbit were evaluated through day 12 PI. These remaining animals were used to confirm the clinical impressions of PALA combination efficacy as demonstrated previously in Example 5.

Group #3: 6 HCMV-inoculated and 1 sham-inoculated animal, intravenous injection of mid-dose PALA (25 mg/kg) on days 2 through 10 PI (A total of 9 IV injections plus mid dose DHPG 7.5 mg/kg/day in 2 divided doses from day 2 through 10 PI (a total of 18 IV injections).

One animal from this therapy group was sacrificed on days 3, 4, 5, and 6 PI. The eyes were enucleated and processed for HCMV recovery by cell sonicate recovery to determine the presence of HCMV and the titer of virus in the chorioretina. The remaining 2 HCMV-infected and 1 sham inoculated rabbit were evaluated through day 12 PI. These remaining animals were used to confirm the clinical impressions of PALA combination efficacy as demonstrated previously in Example 5, and to fine tune the efficacy evaluations.

Group #4: 6 HCMV-inoculated and 1 sham-inoculated animal, intravenous injection of low dose PALA (10 mg/kg) on days 2 through 10 PI (A total of 9 IV injections) plus low dose DHPG 5 mg/kg/day in 2 divided doses from day 2 through 10 PI (a total of 18 IV injections).

One animal from this therapy group was sacrificed on days 3, 4, 5, and 6 PI. The eyes were enucleated and processed for HCMV recovery by cell sonicate recovery to determine the presence of HCMV and the titer of virus in the chorioretina. The remaining 2 HCMV-infected and 1 sham inoculated rabbit were evaluated through day 12 PL. These remaining animals were used to confirm the clinical impressions of PALA combination efficacy as demonstrated previously in Example 5.

Single-agent Positive and Negative Controls

Group #5: 6 HCMV-inoculated animals, intravenous injection of DHPG 10 mg/kg/day in 2 divided doses from day 2 through day 10 PI. A total of 18 IV injections.

Animals in this group were sacrificed in a time course study on day 3, 4, 5 and 6 PI to evaluate reductions in HCMV recovery and titer. Eyes were removed and processed for cell-sonicate recovery of HCMV from the retina. The remaining 2 animals were sacrificed on day 12 PI, and were used to evaluate the clinical efficacy course of PALA on the retina and choroid after intravenous administration.

Group #6: 6 HCMV-inoculated animals, intravenous injection of sterile saline on days 2 through 10 PI.

Animals in this group were sacrificed in a time course study on day 3, 4, 5 and 6 PI to evaluate reductions in HCMV recovery and titer in the retina.

Eyes were removed and processed for cell-sonicate recovery of HCMV. The remaining 2 animals were sacrificed on day 12 PI, and were used to evaluate the clinical efficacy course of PALA on the retina and choroid after intravenous administration.

[4] All animals received daily indirect ophthalmoscopic examinations or slit lamp examinations with a hand held 90 diopter lens to evaluate clinical HCMV disease progression (from days 2 through 10 PI). The fundus examinations are performed independently by two readers who were masked as to the therapy that the rabbits received.

[5] All animals were either sacrificed in a time course study to evaluate PALA single-and combination-agent reductions in HCMV titer or on day 12 PI to confirm the clinical course PALA therapeutic efficacy.

The clinical, virus recovery and histological efficacy results for all drug-treated intravenous therapy groups were correlated with each other and with the placebo therapy group.

Summary of individual animals throughout the course of the efficacy evaluation.

Day-1 All animals pre-evaluated by slit lamp biomicroscopy and fundus examination. Animals numbered 1 through 36; and S1–S5. Rabbits were immediately randomized into groups of animals that received therapy intravenous therapy as indicated below:

Group #1: Rabbits #1, 2, 3, 4 and sham-inoculated rabbit S1–50 mg/kg PALA.

Group #2: Rabbits #5,6,7, 8,9, 10, 11 and 1 sham-inoculated animal #S2—received daily intravenous injections of high-dose PALA (50 mg/kg) and high-dose DHPG (10 mg/kg/day).

Group #3: Rabbits #12, 13, 14, 15, 16, 17 and 1 sham-inoculated animal #S3—received daily intravenous injections of mid-dose PALA (25 mg/kg) plus mid-dose DHPG (7.5 mg/kg/day).

Group #4: Rabbits #18, 19, 20, 21, 22, 23 and 1 sham-inoculated animal #S4—received daily intravenous therapy with low dose PALA (10 mg/kg) plus low dose DHPG (5 mg/kg/day).

Group #5: Rabbits #24, 25, 26, 27, 28, 29 and 1 sham-inoculated animal, #S5—received daily intravenous therapy with high-dose DHPG (10 mg/kg/day).

Group #6: Rabbit #30, 31, 32, 33, 34, 35 and 36 received daily placebo intravenous therapy (sterile saline injections).

Sacrifice of HCMV inoculated single- and combination-agent treated animals:

Day 3 post inoculation: Sacrifice and chorioretinal cell sonicate culture for recovery of HCMV—Group #1: Rabbit #1

Group #2: Rabbit #11
Group #3: Rabbit #16
Group #4: Rabbit #23
Group #5: Rabbit #28
Group #6: Rabbit #34

Day 4 Post inoculation: Sacrifice and chorioretinal cell sonicate for recovery of HCMV—Group #1: Rabbit #2

Group #2: Rabbit #7
Group #3: Rabbit #12
Group #4: Rabbit #18
Group #5: Rabbit #24
Group #6: Rabbit #30

Day 5 Post inoculation: Sacrifice and chorioretinal cell sonicate culture for recovery of HCMV—Group #1: Rabbit #3

Group #2: Rabbit #8
Group #3: Rabbit #13
Group #4: Rabbit #19
Group #5: Rabbit #26
Group #6: Rabbit #31

Day 6 Post inoculation: Sacrifice and chorioretinal cell sonicate culture for recovery of HCMV—Group #1: Rabbit #4

Group #2: Rabbit #6
Group #3: Rabbit #14
Group #4: Rabbit #21
Group #5: Rabbit #27
Group #6: Rabbit #33

Day 12 Post inoculation: Sacrifice and processing of tissues for histological evaluation or for culture HCMV recovery from chorioretinal cell sonicate cultures. The animals sacrificed at the conclusion of the efficacy evaluation were observed daily by indirect ophthalmoscopy. The clinical impressions of the HCMV disease in these animals was used to construct the vitreitis and chorioretinal disease profiles demonstrated graphically in this report. Animals that were sacrificed at the conclusion of the evaluation included:

Group #1: No HCMV infected rabbits, S1
Group #2: Rabbit #9, 10, S2
Group #3: Rabbit #15, 17, S3
Group #4: Rabbit #20, 22, S4
Group #5: Rabbit #25, 29, S5
Group #6: Rabbit #32, 35, 36

Clinical Disease Impressions: Vitreitis and Chorioretinal Disease Development

Figure 8:
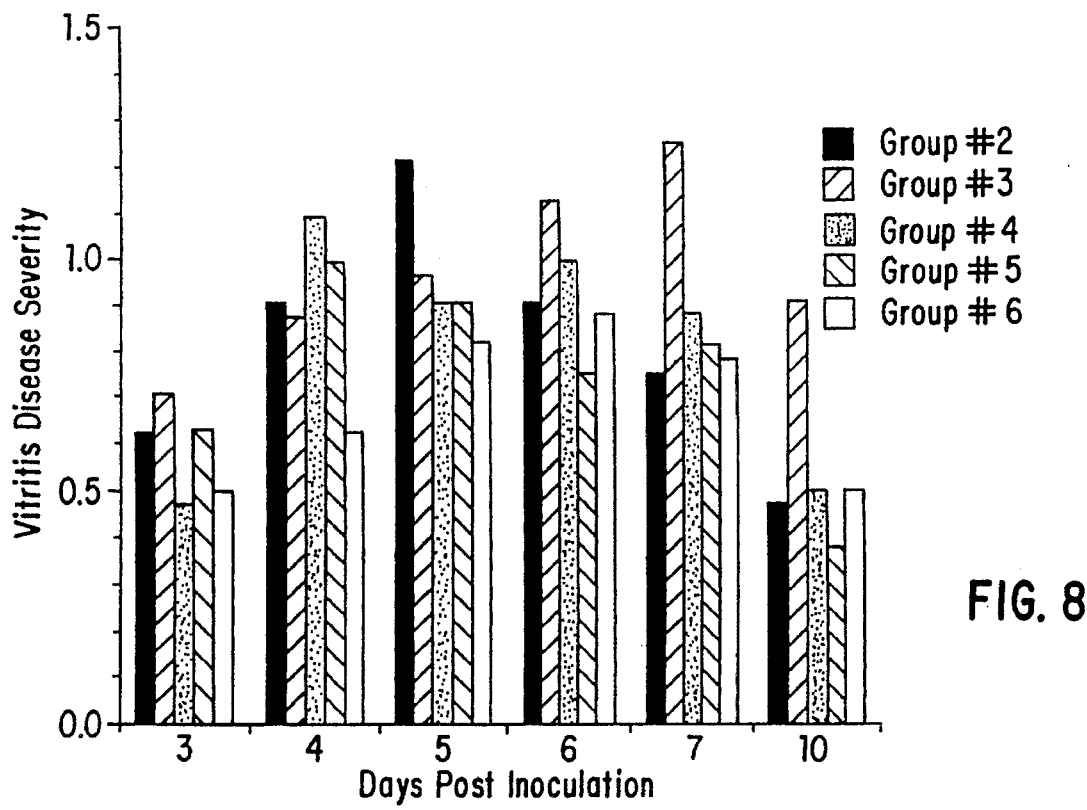
FIG. 8 is a bar graph of the average vitreitis disease severity in single- and combination-agent therapy groups of Example 6.

FIG. 8 summarizes data on the development of chorioretinal and vitreitis development in the intravenous combination and single-agent therapy groups. Chorioretinal disease development was partially obscured by the development of vitreitis on days 5–8 Pi as was demonstrated in the previous efficacy evaluation. The average scores for these days PI are based upon clinical impressions and the previous days fundus examination evaluation.

Table 8, 9, 10, and 11 summarize clinical vitreitis, chorioretinitis and optic nerve head scorn and HCMV recovery from 2 eyes/therapy group on days 3, 4, 5, and 6 PI.

11.2 Results

Single-agent PALA intravenous therapy

Group #1: PALA single-agent therapy 50 mg/kg/day

All rabbits in this therapy group were sacrificed in the time course HCMV recovery study. No animals in this single-agent therapy group were evaluated sequentially throughout the course of the intravenous therapy. The sham-inoculated PALA 50 mg/kg/day treated animal, #S1, did not develop any vitreitis nor chorioretinal disease during the course of the study.

HCMV recovery by cell sonicate assay in this single-agent therapy group demonstrated virus presence in the chorioretina on days 3, 4, 5, and 6 PL HCMV titer in the culture samples was highest on day 3 PI, when an average of 104 pfu HCMV was recovered from the samples. HCMV was recovered from both eyes of animals sacrificed in the time course evaluation. HCMV titers decreased throughout the recovery course such that by day 6 PI, only an average of 101 pfu HCMV was detected in the culture. HCMV recovery in this single agent therapy group was better than recovery in placebo treated eyes, but, HCMV titers in this group were higher than other combination agent or single-agent DHPG treatment groups.

Group #2: Combination agent PALA (50 mg/kg/day) plus DHPG (10 mg/kg/day)

Clinical disease, both vitreitis and chorioretinal disease was minimal in this high-dose PALA plus high-dose DHPG therapy group. Vitreitis, the indirect measurement of chorioretinal HCMV involvement was comparable to single-agent DHPG therapy on all days with the exception of day 5 PI. Chorioretinal disease in this high dose therapy combination group possibly demonstrated an additive efficacy effect when compared to the single agent DHPG therapy group. This high dose combination group was markedly better than the other PALA plus DHPG therapy groups and significantly better than placebo therapy. Optic neuritis was low on all days post inoculation in this group. The average neuritis scores in this group were better than all other combination agent and single agent therapy groups. This observation is important and demonstrates an advantage to this therapy regimen compared to other combination and single-agent therapies. Optic nerve head changes in this model of HCMV infection are a reliable measurement and assessment of chorioretinal disease development and HCMV-induced pathology.

HCMV recovery by assay of retinal tissue in this high-dose combination-agent therapy group demonstrated virus presence in the chorioretina only on days 3 and 4PI. Although only 2 samples were processed/time point/therapy group, the fact that no virus was recovered on day 5, and 6 is of interest. HCMV titer in the culture samples was highest on day 3 PI, when an average of 103.5 pfu HCMV was recovered from the samples. HCMV was recovered from both eyes of the inoculated drug treated animal sacrificed in the time course evaluation only on day 3 PI. By day 4 PI, only 1 of the 2 eyes demonstrated the presence of HCMV by culture. The titer of HCMV in this chorioretinal sample was $10^1$ pfu HCMV. The dramatic reduction in HCMV titer from day 3 to day 4 PI demonstrates the potential additive response of this combination-agent therapy regimen. No HCMV could be recovered from the chorioretinal samples using combinational treatment. HCMV recovery in this high dose combination agent therapy group was better than recovery in placebo treated eyes and better than the HCMV recovery (both frequency and titer of HCMV) in the earlier PALA plus DHPG combination therapy groups. The reduction in HCMV titers in this group are better than other combination agent therapy groups and appear to be as good as the HCMV titer reduction observed in the single-agent DHPG treatment group.

Group #3: Combination agent PALA (25 mg/kg/day) plus DHPG (7.5 mg/kg/day) [mid-dose combination therapy] and Group #4: Combination agent PALA (25 mg/kg/day) plus DHPG (5 mg/kg/day) [low-dose combination agent therapy].

Clinical disease, both vitreitis and chorioretinal disease were moderate in the mid-dose and low-dose PALA plus mid-dose DHPG therapy group. Vitreitis scores in these combination agent therapy groups were not improved when compared to the high-dose combination or the single-agent DHPG therapy groups. Vitreitis remained elevated on day 10 in the mid-dose combination therapy group. Chorioretinal disease assessment demonstrated moderate levels of disease in both combination therapy groups that was clearly visible as retinal pathology on day 10 PI. The average chorioretinal and vitreous disease in these combination therapy groups was more severe than in the high dose combination agent therapy group. The disease progression in the mid-dose therapy group was not different from the disease state in the low-dose combination therapy group. Vitreitis and chorioretinal disease were evident at moderate levels in both of these combination groups. In both the mid-dose and low-dose combination therapy groups the vitreitis and chorioretinal disease more severe than in the high-dose combination and the DHPG single-agent therapy groups. Optic neuritis and optic nerve head changes were present in these two mid-and low-dose therapy groups throughout the study. Both combination therapy groups demonstrated moderate levels of optic nerve head neuritis and pathology. The optic nerve head changes in these groups were not different from the single-agent DHPG therapy group or the placebo therapy group. Optic nerve head changes in these groups were worse when compared to the high dose combination agent therapy group.

HCMV recovery from chorioretinal cell sonicate cultures in these combination therapy groups was intermediate between the placebo HCMV recovery and the single-agent DHPG HCMV recovery. In the mid-dose recovery group, HCMV was recovered from sonicate cultures on days 3, 4, and 6 PI. Titers decreased from an average of 104 on day 3 to and average of 101 on day 6 PI. The HCMV recovery was less than recovery in the placebo therapy group. HCMV recovery was not reduced as rapidly in the mid-dose group when compared to the high dose combination therapy group or the single-agent DHPG therapy group.

HCMV recovery from chorioretinal cell sonicate cultures in the low-dose combination agent group was comparable to the mid-dose therapy group. Fewer chorioretinal samples were positive on days 4, 5, and 6 in this low dose combination therapy group than in the placebo group or the single agent PALA therapy groups. The HCMV titer and frequency of recovery in this low-dose therapy groups was similar to the mid-dose combination HCMV therapy group recovery frequency and HCMV titer.

Histology was performed on the mid-dose and low-dose combination therapy group. The histology is summarized below.

Mid-dose PALA plus DHPG therapy. The histology in this mid-dose combination therapy group demonstrated a mild to moderate accumulation of mixed cell infiltrates in the retina and in the vitreous adjacent to the retina. The retinal destruction was focal to geographic with edema, necrosis and complete obliteration of the full thickness retina. The choroid was moderately congested and edematous. Optic nerve head changes included focal infiltration of the nerve and accumulation of a mixed cell infiltrate at the vitreous interface. The pathology was significant in this sample. This pathology, if compared to the pathology demonstrated in Example 5, was more severe than in the pathology noted in the high-dose PALA plus DHPG therapy groups and in the single-agent therapy group. The pathology in this mid-dose combination therapy group was not as severe as that noted in placebo treated chorioretinal samples (Example 5).

Low-dose PALA plus DHPG therapy. Vitreitis was moderate to severe in this sample. The chorioretinal pathology was limited to discrete areas of immune cell infiltration separated by areas of normal retina and choroid. In areas that were involved in the HCMV reaction, the retina demonstrated edema, immune cell infiltration, necrosis and loss of the normal cellular architecture. The choroid was severely congested with marked engorgement of choroidal vessels and frequent areas of choroiditis. The pathology in this low-dose combination therapy group was similar to the pathology in the mid-dose therapy group. The pathology was more severe and geographic than the pathology in the high dose PALA plus DHPG combination therapy group and in the DHPG single agent therapy group.

Group #5: Single-agent DHPG (10 mg/kg/day).

Animals in this single agent therapy group received DHPG therapy beginning day 2 post inoculation and continuing through day 10 post inoculation. The 10 mg/kg/day DHPG therapy in two divided doses. As demonstrated in Example (5), DHPG therapy did reduce the development of HCMV chorioretinal infection and disease and vitreitis. Chorioretinal disease remained focal with moderate involvement of the optic nerve head in inflammation and in immune cell infiltration of the optic nerve head. The choroid remained moderately congested. The clinical impression of disease in these treated eyes was similar to the high-dose PALA plus DHPG combination therapy group. HCMV disease in this single-agent group was better than the mid-dose and low-dose combination therapy group and better than the placebo treatment group. The clinical disease in the single-agent DHPG treatment group was similar to the high-dose PALA combination treatment group. In fact, the high-dose combination therapy regimen may be slightly better than the single-agent DHPG treatment thus indicating an additive effect of the two intravenous therapy groups.

HCMV recovery from cell sonicate cultures demonstrated a rapidly decreasing HCMV recovery rate and titer of HCMV recovered from the samples. On day 3 PI, HCMV was recovered from both chorioretinas in this therapy group. The titer of HCMV was determined to be 103 pfu. By day 4 PI, HCMV recovery had decreased to a titer of 101 and was evident in only 1 of the 2 chorioretinal samples. No HCMV was recovered on day 5 PI, however, a low titer (101 was recovered from 1 chorioretinal sample on day 6 PI. The decrease in frequency of HCMV recovery and in HCMV titer was better than the mid-dose and low-dose combination therapy group and the single agent PALA group and the placebo therapy group. The pattern of HCMV recovery was not different from that demonstrated in the high-dose combination therapy group.

Group #6: Placebo therapy.

Placebo treated animals received daily single injections of sterile saline + EDTA beginning on day 2 PI and continuing through day 10 PI. Placebo treated eyes developed mild to moderate vitreitis. The vitreitis in the placebo treated group was not as severe as in the other single-agent and combination-agent therapy groups. Chorioretinal disease in these placebo treated eyes was markedly worse than the other therapy groups. Focal retinal vein hemorrhages and intraretinal bleeding was frequent. The focal areas of HCMV disease were numerous and resulted in an average chorioretinal disease scores of 1.5 to 2+. The disease consisted of focal to geographic areas of retinal infiltration, optic nerve inflammation and redness and mild vitreitis. The vitreitis consisted of vitreous strands with peripheral cellular infiltrates, cellular clumping and cloudiness. Placebo therapy did not arrest the development of chorioretinal disease. The average level of optic neuritis and inflammation in the placebo treated eyes was comparable to the other therapy groups.

HCMV recovery from the placebo treatment group demonstrated HCMV recovery on days 3–6 PI in decreasing titers from 104 to 102 in the time course evaluation. The placebo treatment group demonstrated the highest titer recovery compared to the other therapy groups.

11.3 Conclusion

[1] The combination agent therapy using high dose PALA plus DHPG was superior to all other combination agent therapies. In fact, this high dose therapy demonstrated an additive antiviral efficacy effect when compared to DHPG therapy alone.

[2] HCMV was recovered in a time course analysis from all therapy groups. Differences in the frequency of recovery (e.g. the number of virus recovery samples that were positive HCMV) decreased with increasing time post therapy. It appears that the titer of the virus recovered from the chorioretinal sonicate samples also decreased with increasing time post inoculation. The decreases in recovery of HCMV and in HCMV titer corresponded to the therapy that the rabbits were receiving.

[3] Combination agent high dose PALA plus DHPG (therapy group #2) was the most effective combination agent therapy for reducing clinical disease and for reducing HCMV recovery in the chorioretinal cultures. This combination therapy was as good as single-agent DHPG therapy. This combination agent therapy demonstrated an additive antiviral effect when compared to single-agent DHPG therapy.

[4] Ranking of the efficacy of the combination and single-agent therapy groups with regards to the reduction in HCMV recovery:

High-dose combination-agent PALA plus DHPG (Group #2)≈single-agent DHPG (Group #5)>>Mid-Dose Combination agent PALA plus DHPG (Group #3)>Low-dose Combination agent PALA plus DHPG (Group #4)>Single agent PALA (Group #1)>Placebo (Group #6).

[5] Combination therapy of high dose PALA plus DHPG was the most effective at preserving retinal structure (opthalmologically) and this was confirmed by final histopathology.

TABLE 9

Optic neuritis scores for animals treated with single and combination-agent intravenous therapy.

| Group # | Animal | 10/19 3 ONH | 10/20 4 ONH | 10/21 5 ONH | 10/22 6 ONH | 10/23 7 ONH | 10/26 10 ONH |
|---|---|---|---|---|---|---|---|
| 2 | 9 | | NR | 2 | 2 | 2 | 0.5 |
| 2 | 10 | 2* | 2 | 4 | 4 | 5 | 1.5 |
| 2 | S2 | 2 | 0 | 0 | 0 | 0 | 0 |
| 3 | 15 | NR | NR | 4 | 4 | 3 | 3 |
| 3 | 17 | NR | 2 | 4 | NR | 6 | 2 |
| 3 | S3 | 0 | 0 | 0 | 0 | 0 | 0 |
| 4 | 20 | 0 | 2 | NR | 2 | NR | 3 |
| 4 | 22 | NR | NR | 2 | 2 | 6 | 2 |
| 4 | S4 | 0 | 0 | 0 | 0 | 0 | 0 |
| 5 | 25 | NR | NR | 4 | 3 | 3 | 3 |
| 5 | 29 | 2 | NR | 5 | 1 | 6 | 3 |
| 5 | S5 | 0 | 0 | 0 | 0 | 0 | 0 |
| 6 | 35 | 0 | 1 | 5 | 6 | 3 | 3 |
| 6 | 36 | NR | 4 | 4 | NR | NR | 4 |

ONH - Optic Never Head;
NR - not read;
*Scores represent the sum of optic nerve head alterations (neuritis) for both eyes/rabbit.

TABLE 8

Chorioretinal and vitreitis scores for animals treated with single-and combination-agent intravenous therapy.

| Group # | Animal | 10/19 3 V | C | 10/20 4 V | C | 10/21 5 V | C | 10/22 6 V | C | 10/23 7 V | C | 10/26 10 V | C |
|---|---|---|---|---|---|---|---|---|---|---|---|---|---|
| 1 | S1 | 0 | 0 | 0 | 0 | 0 | 0 | 0 | 0 | 0 | 0 | 0 | 0 |
| 2 | 9 | 3.5 | 0 | 5.5 | CT | 5.75 | CT | 4 | 0.5 | 3.5 | 0.5 | 2.25 | 0 |
| 2 | 10 | 1.5 | 0 | 1.75 | 0.5 | 4 | CT | 3.25 | 0.5 | 2.5 | 0.5 | 1.5 | 0 |
| 2 | S2 | 0 | 0 | 0 | 0 | 0 | 0 | 0 | 0 | 0 | 0 | 0 | 0 |
| 3 | 15 | 3.5 | 0.75 | 5.25 | 0.5 | 4 | CT | 4.5 | 1 | 4.5 | 0.5 | 3.75 | 0 |
| 3 | 17 | 2.25 | 1 | 1.75 | 1.5 | 3.75 | 1 | 4.5 | CT | 5.5 | CT | 3.5 | CT |
| 3 | S3 | 0 | 0 | 0 | 0 | 0 | 0 | 0 | 0 | 0 | 0 | 0 | 0 |
| 4 | 20 | 1.75 | 0 | 4.5 | CT | 3 | 1 | 4 | CT | 5 | CT | 2.25 | 1 |
| 4 | 22 | 2 | 0.5 | 4 | CT | 4.25 | 1 | 4 | CT | 2 | 0 | 1.75 | 0 |
| 4 | S4 | 0 | 0 | 0 | 0 | 0 | 0 | 0 | 0 | 0 | 0 | 0 | 0 |
| 5 | 25 | 3 | 0 | 4 | 0.5 | 4.5 | CT | 3.5 | 0.5 | 3.5 | 0 | 1.75 | 0 |
| 5 | 29 | 2 | 0 | 4.25 | CT | 2.75 | 0.5 | 2.5 | 0 | 3 | 0 | 1.25 | 0 |
| 5 | S5 | 0 | 0 | 0 | 0 | 0 | 0 | 0 | 0 | 0 | 0 | 0 | 0 |
| 6 | 35 | 1.75 | 0 | 1.5 | 2 | 2.5 | 2 | 2.5 | CT | 1.75 | 0 | 1 | 0 |
| 6 | 36 | 3.25 | 1.5 | 3.5 | 1.5 | 4 | 1.5 | 4.5 | CT | 4.5 | CT | 3 | 1.75 |

*Scores represent sum of both eyes/rabbit;
CT can't tell chorioretinal disease due to vitreitis

TABLE 10

HCMV recovery from chorioretinal cell sonicate cultures on days 3 to 6 post inoculation.

| Day of sacrifice | Animal number | HCMV Recovered OD | HCMV Recovered OS | HCMV Titer OD | HCMV Titer OS |
|---|---|---|---|---|---|
| 3 | 1 | + | + | $10^4$ | $10^4$ |
| 3 | 11 | + | + | $10^3$ | $10^3$ |
| 3 | 19 | + | − | $10^4$ | — |
| 3 | 23 | + | + | $10^2$ | $10^4$ |
| 3 | 28 | + | + | $10^3$ | $10^3$ |
| 3 | 34 | + | − | $10^4$–$10^5$ | — |
| 4 | 2 | + | + | $10^3$ | $10^2$ |
| 4 | 7 | − | + | — | $10^1$ |
| 4 | 12 | + | − | $10^2$ | — |
| 4 | 18 | − | + | — | $10^3$ |
| 4 | 24 | + | − | $10^1$ | — |
| 4 | 30 | + | + | $10^3$ | $10^3$ |
| 5 | 3 | + | + | $10^1$ | $10^2$ |
| 5 | 8 | − | − | — | — |
| 5 | 13 | − | − | — | — |
| 5 | 19 | − | − | — | — |
| 5 | 26 | − | − | — | — |
| 5 | 31 | − | − | — | $10^2$ |
| 6 | 4 | + | + | $10^1$ | $10^1$ |
| 6 | 6 | − | − | — | — |
| 6 | 14 | − | + | — | $10^1$ |
| 6 | 21 | + | − | $10^1$ | — |
| 6 | 27 | + | − | $10^1$ | — |
| 6 | 33 | − | + | — | $10^2$ |

The cultures represent HCMV cell sonicate cultures during intravenous therapy. Cultures were plated onto 12 wells in a costar cluster. All negative cultures were blind passage 4 separate times for a total of 28 days in culture. The HCMV titer in positive cultures were determined by standard plaque assay after determination of HCMV presence (positive) in the cultures.

TABLE 11

Time course HCMV recovery from single- and combinational-agent therapy groups:
Average Titer of HCMV recovered from chorioretinal cultures

| Therapy Group | Days Post Inoculation 3 | 4 | 5 | 6 |
|---|---|---|---|---|
| Group #1 [50 mg/kg/day PALA] | 2/2*; $10^{4**}$ | 2/2; $10^{2.5}$ | 2/2; $10^{1.5}$ | 2/2; $10^1$ |
| Group #2 [50 mg/kg/day PALA plus 10 mg/kg/day DHPG] | 2/2; $10^{3.5}$ | 1/2; $10^1$ | 0/2 | 0/2 |
| Group #3 [25 mg/kg/day PALA plus 7.5 mg/kg/day DHPG] | 1/2; $10^4$ | 1/2; $10^2$ | 0/2 | 1/2; $10^1$ |
| Group #4 [10 mg/kg/day PALA plus 5 mg/kg/day DHPG] | 2/2; $10^3$ | 1/2; $10^3$ | 0/2 | 1/2; $10^1$ |
| Group #5 [10 mg/kg/day DHPG] | 2/2; $10^3$ | 1/2; $10^1$ | 0/2 | 1/2; $10^1$ |
| Group #6 [placebo] | 2/2; $10^{4.5}$ | 2/2; $10^3$ | 1/2; $10^2$ | 1/2; $10^2$ |

12. EXAMPLE 7

PALA ascending dose efficacy evaluation in the rabbit: clinical and HCMV recovery in a time course evaluation.

These experiments were undertaken to evaluate the efficacy of the PALA in an ascending dose intravenous therapy study after HCMV infection in the rabbit model by comparing clinical HCMV disease, HCMV recovery from cell sonicate cultures and histopathological HCMV induced disease severity. HCMV titers from chorioretinal sonicate cocultures were compared to DHPG and placebo treated animal HCMV recovery titers.

12.1 Methods

A total of 60 pigmented rabbits were used in this study. Animals were evaluated by slit lamp and indirect ophthalmoscopy to determine normal ocular morphology and lack of pre-existing pathology. Animals were handled as follows:

[1] On day 0, all animals were evaluated by indirect ophthalmoscopy to insure that all posterior segments were normal. Following the fundus examination, animals received topical eyedrops to dilate the pupils. The topical eye drop therapy continued daily through day 10 after inoculation.

[2] On day 0, all rabbits were inoculated by vitreal injection of $10^5$ PFU HCMV strain AD 169 in 100 μL.

[3] Animals were maintained in individual cages and developing chorioretinal HCMV disease was monitored daily. On day 2 PI, HCMV-inoculated animals were divided into groups of 10 HCMV-inoculated rabbits plus 1 sham-inoculated rabbit. The HCMV-infected and sham-inoculated rabbits received intravenous therapy as indicated below:

Single-agent PALA ascending dose intravenous therapy

Group #1: 10 HCMV-inoculated rabbits, intravenous injection of PALA (50 mg/kg) on days 2 through 10 PI. A total of 9 IV injections per rabbit.

Animals in this group were sacrificed in a time course study on day 3, 4, 5 and 6 PI to evaluate reductions in HCMV recovery and titer. Two animals (4 eyes) were removed and processed for cell-sonicate recovery of HCMV at each time point post inoculation. The remaining 2 animals were followed sequentially through the course of the 9 day therapy period.

Group #2: 10 HCMV-inoculated rabbits, intravenous injection of PALA (75 mg/kg) on days 2 through 10 PI. A total of 9 IV injections per rabbit.

Animals in this group were sacrificed in a time course study on day 3, 4, 5 and 6 PI to evaluate reductions in HCMV recovery and titer. Two animals (4 eyes) were removed and processed for cell-sonicate recovery of HCMV at each time point post inoculation. The remaining 2 animals were followed sequentially through the course of the 9 day therapy period.

Group #3: 10 HCMV-inoculated rabbits, intravenous injection of PALA (100 mg/kg) on days 2 through 10 PI. A total of 9 IV injections per rabbit.

Animals in this group were sacrificed in a time course study on day 3, 4, 5 and 6 PI to evaluate reductions in HCMV recovery and titer. Two animals (4 eyes) were removed and processed for cell-sonicate recovery of HCMV at each time point post inoculation. The remaining 2 animals will be followed sequentially through the course of the 9 day therapy period.

Combination-agent PALA plus dexamethasone subconjunctival therapy

Group #4: 10 rabbits received 4 mg subconjunctival depo dexamethasone 1 hour prior to HCMV inoculation. Rabbits received intravenous therapy with PALA (75 mg/kg/day from days 2 through 10 PI).

Animals in this group were sacrificed in a time course study on day 3, 4, 5 and 6 PI to evaluate reductions in HCMV recovery and titer. Two animals (4 eyes) were removed and processed for cell-sonicate recovery of HCMV at each time point post inoculation. The remaining 2 animals were followed sequentially through the course of the 9 day therapy period.

Positive and Negative Control therapy groups

Group #5: 10 HCMV-inoculated animals, intravenous injection of DHPG 10 mg/kg/day in 2 divided doses from day 2 through day 10 PI.

Animals in this group were sacrificed in a time course study on day 3, 4, 5 and 6 PI to evaluate reductions in HCMV recovery and titer. Two animals (4 eyes) were removed and processed for cell-sonicate recovery of HCMV at each time point post inoculation. The remaining 2 animals were followed sequentially through the course of the 9 day therapy period.

Group #6: 10 HCMV-inoculated animals, intravenous injection of sterile saline on days 2 through 10 PI.

Animals in this group were sacrificed in a time course study on day 3, 4, 5 and 6 PI to evaluate reductions in HCMV recovery and titer from the retina. Two animals (4 eyes) were removed and processed for cell-sonicate recovery of HCMV at each time point post inoculation. The remaining 2 animals were followed sequentially through the course of the 9 day therapy period.

[4] All animals received daily indirect ophthalmoscopic examinations or slit lamp examinations with a hand held +90 diopter lens to evaluate clinical HCMV disease progression (From days 2 through 10 PI). The fundus examinations were performed independently by two readers who were masked as to the therapy that the rabbits received.

[5] All animals were either sacrificed in the time course study to evaluate PALA single-agent reductions in HCMV titer on days 3, 4, 5, or 6 after inoculation, or on day 12 PI to confirm the clinical course PALA therapeutic efficacy by histology.

Clinical, virus recovery and histological efficacy results for all drug-treated intravenous therapy groups were correlated with each other and with the placebo therapy group.

Summary of individual rabbits throughout the course of this ascending dose efficacy evaluation.

Day 0 All animals were preevaluated by slit lamp biomicroscopy and fundus examination. Animals were numbered 1 through 60; and S1–S3. Immediately after preexamination, the animals were inoculated by intravitreal injection of HCMV. Rabbits were immediately randomized into groups of animals.

Day 1 Animals received intravenous therapy (from day 1 through day 10) as indicated below:

Group #1: Rabbits #1, 2, 3, 4, 5, 6, 7, 8, 9, 10 and sham-inoculated rabbit S1—50 mg/kg PALA.

Group #2: Rabbits # 11, 12, 13, 14, 15, 16, 17, 18, 19, 20 and 1 sham-inoculated animal #S2— received daily intravenous injections of 75 mg/kg PALA.

Group #3: Rabbits #21, 22, 23, 24, 25, 26, 27, 28, 29, 30 and 1 sham-inoculated animal #S3— received daily intravenous injections of 100 mg/kg PALA.

Group #4: Rabbits #31, 32, 33, 34, 35, 36, 37, 38, 39, and 40 received a single subconjunctival injection of 4 mg depomedrol (steroid) immediately before inoculation with HCMV. These animals then received daily intravenous therapy with 75 mg/kg PALA.

Group #5: Rabbits #41, 42, 43, 44, 45, 46, 47, 48, 49, and 50 received daily intravenous therapy with DHPG (10 mg/kg/day).

Group #6: Rabbit #51, 52, 53, 54, 55, 56, 57, 58, 59, and 60 received daily placebo intravenous therapy (sterile 0.19% saline plus 1M EDTA injections).

Sacrifice of HCMV inoculated single-agent treated animals:

Day 3 post inoculation: Sacrifice and chorioretinal cell sonicate culture for recovery of HCMV—

Group #1: Rabbit #1 and 2
Group #2: Rabbit #11 and 12
Group #3: Rabbit #21 and 22
Group #4: Rabbit #31 and 32
Group #5: Rabbit #41 and 42
Group #6: Rabbit #51 and 52

Day 4 Post inoculation: Sacrifice and chorioretinal cell sonicate culture for recovery of HCMV—

Group #1: Rabbit #3 and 4
Group #2: Rabbit #13 and 14
Group #3: Rabbit #23 and 24
Group #4: Rabbit #33 and 34
Group #5: Rabbit #43 and 44
Group #6: Rabbit #53 and 54

Day 5 Post inoculation: Sacrifice and chorioretinal cell sonicate culture for recovery of HCMV—

Group #1: Rabbit #5 and 6
Group #2: Rabbit #15 and 16
Group #3: Rabbit #25 and 26
Group #4: Rabbit #35 and 36
Group #5: Rabbit #45 and 46
Group #6: Rabbit #55 and 56

Day 6 Post inoculation: Sacrifice and chorioretinal cell sonicate for culture for recovery of HCMV—

Group #1: Rabbit #7 and 8
Group #2: Rabbit #17 and 18
Group #3: Rabbit #27 and 28
Group #4: Rabbit #37 and 38
Group #5: Rabbit #47 and 48
Group #6: Rabbit #57 and 58

Day 12 Post inoculation: Sacrifice and processing of tissues for histological evaluation or for HCMV recovery from chorioretinal cell sonicates by tissue culture. The animals sacrificed at the conclusion of the efficacy evaluation were observed daily by indirect ophthalmoscopy. The clinical impressions of the HCMV disease in these animals was used to construct the vitreo-retinal disease profiles demonstrated graphically in this report. Animals that were sacrificed at the conclusion of the evaluation included:

Clinical Disease Impressions: Vitreitis and Chorioretinal Disease Development

Figure 9:
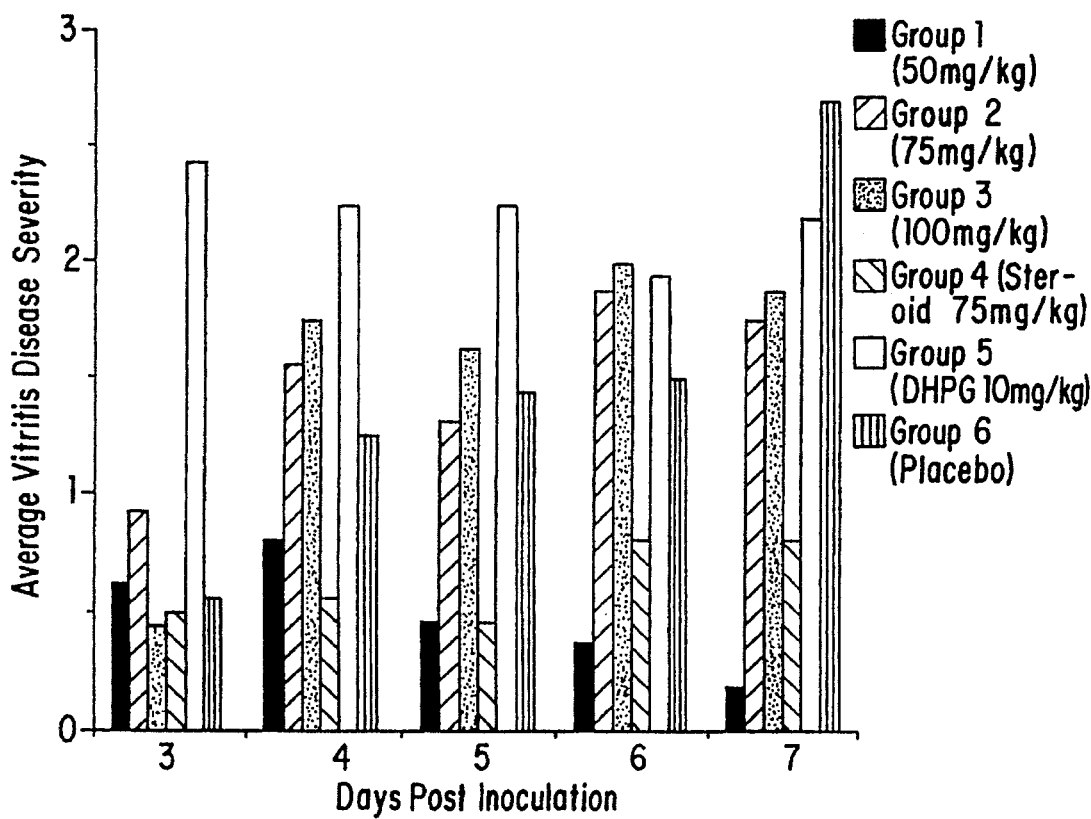
FIG. 9 is a bar graph of the average vitreitis disease severity found in the therapy groups of Example 7.
Figure 10:
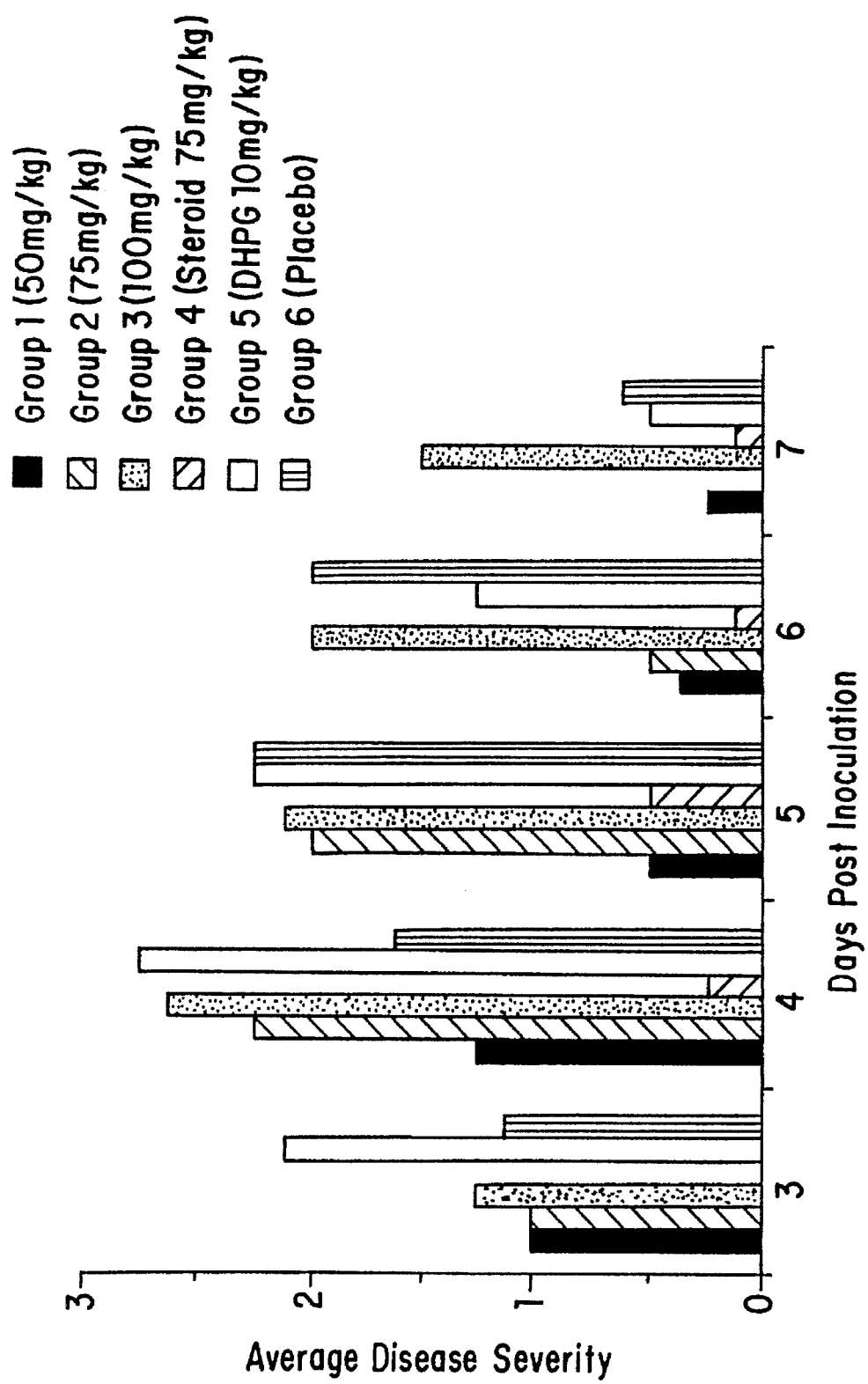
FIG. 10 is a bar graph of the average optic nerve disease severity in the therapy groups of Example 7.

FIGS. 9 and 10 summarize data on the development of vitrioretinal disease development in the intravenous single-agent therapy groups. Chorioretinal disease development was partially obscured by the development of vitreitis in 40% of the eyes by day 4–5 after inoculation. The bar graphs demonstrate trends in the vitrioretinal disease course in the ascending dose PALA treated and control treated animals.

Tables 12, 13, 14 and 15 summarize raw data on vitreitis and optic nerve head disease severity and HCMV recovery from 4 eyes/therapy group on days 3, 4, 5, and 6 PI.

12.2 Results

Single-agent PALA intravenous therapy

Group #1: PALA single-agent therapy 50 mg/kg/day

Rabbits #1 through 8 in this therapy group were sacrificed in the time course HCMV recovery study. Animals #9 and 10 in this 50 mg/kg/day single-agent therapy group were evaluated sequentially throughout the course of the intravenous therapy. Clinical disease demonstrated as vitreitis increased through day 6 post inoculation. On day 7 PI, the vitreitis (inflammatory response) had decreased to low levels. This observation is similar to the previous observations on vitreitis disease development in single-agent 50 mg/kg PALA therapy. The optic nerve head disease severity was also similar to previously reported 50 mg/kg/day therapy eyes. In this study, optic nerve head pathology peaked on day 4 after inoculation and decreased to low levels throughout the rest of the study.

HCMV recovery by cell sonicate assay in this single-agent therapy group demonstrated virus presence in the chioretina on days 3, 4, 5, and 6 PI. HCMV titer in the culture samples was highest on day 3 PI, when an average of $10^{3.5}$ pfu HCMV was recovered from the 4 chorioretinal cell sonicate samples. The frequency of recovery of HCMV from treated eyes decreased on days 4 and 5 post inoculation. A rebound in virus recovery (frequency of HCMV recovery) was noted on day 6 PI, when HCMV was recovered from 4/4 chorioretinal cell sonicate samples. HCMV titers decreased throughout the recovery course except on day 6 PI, when a slight rebound in HCMV titer to $10^2$ pfu/ml was noted. HCMV recovery in this single agent therapy group was better than recovery in placebo treated eyes, and comparable to DHPG treated eyes. (DHPG treated eyes had slightly lower titers of HCMV and fewer numbers of positive chorioretinal samples in the recovery study).

The sham-inoculated PALA 50 mg/kg/day treated animal, #S1, develop mild vitreitis during the course of the study. The level of vitreitis in the 50 mg/kg/day sham-inoculated animal was 0.5 to 0.75 on day 7 post inoculation.

Group #2: PALA single-agent therapy 75 mg/kg/day

Rabbits #11 through 18 in this therapy group were sacrificed in the time course HCMV recovery study. Animals #19 and 20 in this 75 mg/kg/day single-agent therapy group were evaluated sequentially throughout the course of the intravenous therapy. Clinical disease demonstrated as vitreitis increased through day 6 post inoculation. On day 7 PI, the vitreitis (inflammatory response) remained elevated. The optic nerve head disease severity was also similar to previously reported 50 mg/kg/day therapy eyes. Optic nerve head pathology peaked on day 4 after inoculation and decreased rapidly. By day 7 post inoculation, no optic nervehead alterations were evident by clinical evaluation. The sham-inoculated PALA 50 mg/kg/day treated animal, #S1, did not develop any vitreitis nor chorioretinal disease during the course of the study.

HCMV recovery by cell sonicate assay in this single-agent therapy group demonstrated virus presence in the chorioretina on days 3, 4, 5, and 6 PI. HCMV titer in the culture samples was highest on days 3 and 4 PI, when an average of $10^{4.5}$ pfu HCMV and $10^{3.75}$ pfu HCMV were recovered from the chorioretinal cell sonicate samples at each time point. The HCMV titer decreased to low levels on day 5 PI. The frequency of recovery of HCMV from treated eyes decrease on days 4 and 5 post inoculation. On day 6 PI, the titer remained low. However, the number of samples from which virus was recovered increased on day 6 PI demonstrating the rebound observed in the 50 mg/kg/day therapy group. On day 6 PI in this 75 mg/kg/day treated group, 3/4 samples were positive for HCMV by cell sonicate recovery. This increase in frequency of recovery of HCMV in the single-agent PALA treated groups was reproducible. HCMV recovery in this single agent therapy group was comparable to placebo therapy. This single-agent therapy group was not as effective as DHPG in reducing the titer of HCMV recovered from chorioretinal tissues and in reducing the frequency of HCMV recovery.

Group #3: PALA single-agent therapy 100 mg/kg/day

Rabbits #21 through 28 in this therapy group were sacrificed in the time course HCMV recovery study. Animals #29 and 30 in this 100 mg/kg/day single-agent therapy group were evaluated sequentially throughout the course of the intravenous therapy. Clinical disease demonstrated as vitreitis elevated throughout the study. On day 7 PI, the vitreitis (inflammatory response) remained elevated, and was comparable to the vitreitis observed in the 75 mg/kg/day group. The optic nerve head disease severity was also elevated above the disease in the 50 mg/kg/day treated eyes. Optic nerve head pathology peaked on day 4 after inoculation. By day 7 post inoculation, optic nervehead alterations were evident by clinical evaluation at moderate to high levels. Both the vitreitis and optic nerve head disease severity were increased compared to other single-agent PALA, DHPG and placebo therapies. The 100 mg/kg/day dose is most probably either at the toxicity threshold for the compound or slightly above the toxicity threshold. The fact that the HCMV disease in the 100 mg/kg/day treated animals failed to improve is significant. These results on the ascending dose tolerance demonstrate that this high concentration of PALA was not tolerated. In fact, the 100 mg/kg/day dose was toxic to the animals.

The sham-inoculated PALA/kg/day treated animal, #S3, developed moderate vitreitis and transient optic nerve head alterations on days 5–7 post inoculation. These results demonstrate that the 100 mg/kg/day therapy was in the toxic range.

HCMV recovery by culture of cell sonicate in this single-agent therapy group demonstrated viral presence in the chorioretina on days 3, 4, 5, and 6 PI. HCMV titer in the culture samples was highest on day 3 Pi, when an average of $10^4$ pfu HCMV was recovered from the chorioretinal cell sonicate samples. The HCMV titer decreased to low recovery levels on day 5 PI ($10^2$ pfu/ml). Most importantly, the frequency of recovery of HCMV from treated eyes decreased on days 4 and 5 post inoculation. On day 6 PI, however, the titer of HCMV recovered from chorioretinal cell sonicate cultures increased as did the number of positive cultures (e.g. the frequency of HCMV recovery form cell sonicate samples). On day 6 PI in this 100 mg/kg/day treated group, 3/4 samples were positive for HCMV by cell sonicate recovery. The titer of HCMV was increased to levels similar to HCMV recovery titers on day 3 PI. HCMV recovery in this single agent therapy group was significantly higher than HCMV recovery in placebo treated animals. This single-agent therapy group was not effective in reducing the clinical disease progression or HCMV recovery from cell sonicate cultures.

Group #4: PALA single-agent therapy 100 mg/kg/day plus 4 mg subconjunctival steroid injection Rabbits #31 through 38 in this therapy group were sacrificed in the time course HCMV recovery study. Animals #39 and 40 in this 75 mg/kg/day single-agent therapy plus 4 mg subconjunctival steroid therapy group were evaluated sequentially throughout the course of the intravenous therapy. Clinical disease demonstrated as vitreitis was mild throughout the course of the evaluation period. The optic nerve head disease severity was also reduced compared to all other therapy groups. These reductions in clinical disease severity were in direct response to the subconjunctival steroid injection which quieted the eye and reduced the host immune response to the HCMV inoculation.

HCMV recovery by cell sonicate assay in this single-agent therapy group demonstrated virus presence in the chorioretina on days 3, 4, 5, and 6 PI. HCMV titers in the culture samples remained elevated throughout the course of the study. The average titer of HCMV recovered was $10^3$ pfu on days 3–6 post inoculation. In addition to the higher HCMV titer recovered in the steroid treated group, the frequency of HCMV recovery (number of positive samples) was similar to the 50 mg/kg/day and 75 mg/kg/day treated groups (e.g. a gradual decrease in frequency of HCMV recovery followed by a rebound of HCMV recovery on day 6 PI). Although the development of vitreitis and optic nerve head alterations were decreased in this steroid treated group, the titer of virus was elevated suggesting that the steroids may have enhanced HCMV replication (or detection). This therapy with PALA at 75 mg/kg/day was not effective in suppressing disease development and HCMV replication and recovery from chorioretinal tissues.

Group #5: Single-agent DHPG (10 mg/kg/day).

Rabbits #41 through 48 in this therapy group were sacrificed in the time course HCMV recovery study. Animals #49 and 50 in this 10 mg/kg/day single-agent DHPG therapy plus group were evaluated sequentially throughout the course of the intravenous therapy. Animals in this single agent therapy group received DHPG therapy beginning day 2 post-inoculation and continuing through day 10 post-inoculation. The 10 mg/kg/day DHPG therapy in two divided doses. As demonstrated in previous studies, DHPG therapy did reduce the development of HCMV-induced optic nerve disease severity. The development of vitreitis was only marginally affected by the DHPG therapy.

HCMV recovery from cell sonicate cultures demonstrated a rapidly decreasing HCMV recovery rate and titer of HCMV recovered from the samples. On day 3 PI, the titer of HCMV was determined to be $10^3$ pfu. By day 4 PI, HCMV recovery had decreased to a titer of $10^{1.25}$. HCMV recovery frequency and titer continued to decrease through day 6 PI. No rebound in HCMV titer or in the number of positive HCMV tissues was demonstrated in the DHPG therapy group. The pattern of HCMV recovery and titer decreases is not different from that demonstrated previously in other single-agent DHPG therapy groups.

Group #6: Placebo therapy.

Rabbits #51 through 58 in this therapy group were sacrificed in the time course HCMV recovery study. Animals #59 and 60 in this placebo treated therapy group were evaluated sequentially throughout the course of the intravenous therapy. Placebo treated animals received daily single injections of sterile saline+EDTA beginning on day 2 PI and continuing through day 10 PI. Placebo treated eyes developed mild to moderate vitreitis. The vitreitis in the placebo treated group continued to progress throughout the course of the study. The vitreitis consisted of vitreous strands with peripheral cellular infiltrates, cellular clumping and cloudiness. The average level of optic neuritis and inflammation in the placebo treated eyes was comparable to the other therapy groups.

HCMV recovery from the placebo treatment group demonstrated HCMV recovery on days 3–6 PI in decreasing titers from $10^{4.5}$ to $10^2$ in the time course evaluation. The placebo treatment group demonstrated the highest titer recovery compared to the other therapy groups. There was no rebound in HCMV recovery or titer on day 6 as was demonstrated in the PALA single-agent treatment groups.

12.3 Conclusion

[1] Treatment of rabbits with ascending doses of PALA 50, 75 and 100 mg/kg/day did not result in an increase in efficacy. In fact, the 100 mg/kg/day group was toxic to the animals. The ocular disease remained at high levels. The 75 mg/kg/day dose was not improved when compared to the 50 mg/kg/day PALA dose or to the 10 mg/kg/day DHPG dose.

[2] HCMV was recovered in a time course analysis from all therapy groups. Differences in the frequency of recovery (e.g. the number of virus recovery samples that were positive HCMV) decreased with increasing time post therapy. It appears that the titer of the virus recovered from the chorioretinal sonicate samples also decreased with increasing time post inoculation. Of interest was the result that in all PALA single-agent therapy groups, there was a rebound in HCMV detection on day 6 PI and in HCMV titer on day 6 PI. This titer and frequency observation was more pronounced at higher concentrations of PALA therapy.

[3] The subconjunctival steroid injected group results demonstrated that the steroid therapy did suppress the vitreitis and optic nerve head pathology. The disease course was easier to evaluate in the steroid treated group. The 75 mg/kg/day therapy, as in the non-steroid treated 75 mg/kg/day treatments was not as effective as DHPG therapy. One potential problem with the steroid use was the result that HCMV titers remained elevated throughout days 3 through 6 PI. In addition to the titer elevation, the frequency of HCMV recovery was similar to that observed in the single-agent 75 mg/kg/day PALA treated eyes.

[4] Ranking of the efficacy of the single-agent therapy groups with regards to the reduction in HCMV recovery in this ascending dose therapy evaluation are:

DHPG therapy (Group #5)>PALA single-agent 50 mg/kg/day (Group #1)>>PALA single-agent 75 mg/kg/day (Group #2)>or equal to placebo therapy (Group #6)>>Single-agent PALA 100 mg/kg/day (Group #3)>Single-agent PALA 75 mg/kg/day plus 4 mg subconjunctival steroid injection (Group #4).

From the results in this study and in the previous studies, it appears that single-agent PALA therapy is not as effective as DHPG therapy in reducing the development of HCMV disease in the retina and in reducing HCMV virus recovery (both titer of HCMV recovered and the frequency of HCMV recovery from chorioretinal samples). Therefore, as demonstrated in Example 6 it is preferable to use PALA in combination therapy when treating CMV viral infection.

Although certain of the results against HCMV appear to be irreconcilable, both low dose PALA plus DHPG and high dose PALA plus DHPG were more effective than single dose PALA or single dose DHPG in preserving the optical nerve and reducing viral titers.

TABLE 12

Chorioretinal and vitreitis scores for animals treated with single-agent intravenous therapy.

| | | Vitreo-retinal scores | | | | |
|---|---|---|---|---|---|---|
| Group # | Animal | 1/11 3 | 1/12 4 | 1/13 5 | 1/14 6 | 1/15 7 |
| 1 | 9 | 1.0* | 0.75 | 0.65 | 0.75 | 0.4 |
| 1 | 10 | 1.5 | 2.5 | 1.25 | 0.6 | 0.4 |
| 2 | 19 | 2.25 | 2.75 | 1.75 | 2.0 | no |
| 2 | 20 | 1.5 | 3.5 | 3.5 | 5.5 | score 5.0 |
| 3 | 29 | 1.0 | 4.5 | 3.5 | 4.0 | 3.25 |
| 3 | 30 | 0.75 | 3.75 | 3.0 | 4.0 | 4.25 |
| 4 | 39 | 1.0 | 0.75 | 0.75 | 1.5 | 1.0 |
| 4 | 40 | 1.0 | 1.5 | 1.0 | 1.75 | 2.25 |
| 5 | 49 | 4.75 | 3.75 | 4.0 | 2.5 | 3.25 |

TABLE 12-continued

Chorioretinal and vitreitis scores for animals treated with single-agent intravenous therapy.

| | | Vitreo-retinal scores | | | | |
|---|---|---|---|---|---|---|
| Group # | Animal | 1/11 3 | 1/12 4 | 1/13 5 | 1/14 6 | 1/15 7 |
| 5 | so | 5.0 | 5.75 | 5.0 | 5.25 | 5.5 |
| 6 | 59 | 1.0 | 2.25 | 3.0 | 3.0 | 1.75** |
| 6 | 60 | 1.25 | 2.75 | 2.75 | 3.0*** | 3.0 |

*Scores represent sum of both eyes/rabbit.
**Only one could be evaluated
***White reflex only

TABLE 13

Optic neuritis scores for animals treated with single-agent intravenous therapy.

| | | Optic Neuritis scores | | | | |
|---|---|---|---|---|---|---|
| Group # | Animal | 1/11 3 ONH | 1/12 4 ONH | 1/13 5 ONH | 1/14 6 ONH | 1/15 7 ONH |
| 1 | 9 | 2.0 | 2.0 | 1.0 | 1.0 | 1.0 |
| 1 | 10 | 2.0 | 3.0 | 1.0 | 0.5 | 0 |
| 2 | 19 | 2.0 | 4.0 | 3.0 | 2.0 | 0 |
| 2 | 20 | 2.0 | 5.0 | 5.0 | NR | NR |
| 3 | 29 | 2.0 | 6.0 | 5.0 | 4.0 | 2.5 |
| 3 | 30 | 3.0 | 5.0 | 4.0 | 4.0 | 4.0 |
| 4 | 39 | 0 | 0 | 1.0 | 0 | 0 |
| 4 | 40 | 0 | 1.0 | 1.0 | 0.5 | 0.5 |
| 5 | 49 | 5.0 | 6.0 | 4.0 | 2.0 | 2.0 |
| 5 | 50 | 4.0 | 5.0 | 5.0 | 2.0 | ? |
| 6 | 50 | 3.0 | 3.0 | 5.0 | 4.0 | 5.0 |
| 6 | 60 | 2.0 | 4.0 | 2.0* | 4.0 | ? |

ONH - Optic Nerve Head;
NR - not read;
*Scores represent the sum of optic nerve head alterations (neuritis) for both eyes/rabbit.
? Fundus view obscured;
**Only one side could be evaluated.

TABLE 14

HCMV recovery from chorioretinal cell sonicate(s) by tissue culture on days 3 to 6 post inoculation.

| | | | HCMV Recovered | | HCMV Titer | |
|---|---|---|---|---|---|---|
| Group # | Day of Sacrifice | Animal Number | OD | OS | OD | OS |
| 1 | 3 | 1 | + | + | $10^3$ | $10^4$ |
| 1 | 3 | 2 | + | + | $10^4$ | $10^3$ |
| 1 | 4 | 3 | − | − | — | — |
| 1 | 4 | 4 | + | − | $10^4$ | — |
| 1 | 5 | 5 | − | + | — | $10^2$ |
| 1 | 5 | 6 | + | − | $10^2$ | — |
| 1 | 6 | 7 | + | + | $10^2$ | $10^3$ |
| 1 | 6 | 8 | + | + | $10^2$ | $10^2$ |
| 1 | 12 | 9 | − | − | — | — |
| 1 | 12 | 10 | − | − | — | — |
| 2 | 3 | 11 | + | + | $10^5$ | $10^4$ |
| 2 | 3 | 12 | + | + | $10^4$ | $10^4$ |
| 2 | 4 | 13 | + | + | $10^4$ | $10^3$ |
| 2 | 4 | 14 | + | − | $10^4$ | — |
| 2 | 5 | 15 | − | − | — | — |
| 2 | 5 | 16 | − | + | — | $10^2$ |
| 2 | 6 | 17 | + | + | $10^3$ | $10^4$ |
| 2 | 6 | 18 | − | − | — | — |
| 2 | 12 | 19 | − | − | — | — |
| 2 | 12 | 20 | − | − | — | — |
| 3 | 3 | 21 | No data/animal died prior to culture | | | |
| 3 | 3 | 22 | + | + | $10^4$ | $10^3$ |
| 3 | 4 | 23 | + | + | $10^5$ | $10^3$ |
| 3 | 4 | 24 | + | + | $10^3$ | $10^4$ |
| 3 | 5 | 25 | − | + | — | $10^2$ |
| 3 | 5 | 26 | − | − | — | — |
| 3 | 6 | 27 | + | − | $10^2$ | — |
| 3 | 6 | 28 | + | + | $10^2$ | $10^3$ |
| 3 | 12 | 29 | − | − | — | — |
| 3 | 12 | 30 | − | − | — | — |
| 4 | 3 | 31 | + | − | $10^4$ | — |
| 4 | 3 | 32 | − | + | — | $10^4$ |
| 4 | 4 | 33 | + | + | $10^3$ | $10^4$ |
| 4 | 4 | 34 | − | − | — | — |
| 4 | 5 | 35 | − | − | — | — |
| 4 | 5 | 36 | − | + | — | $10^3$ |
| 4 | 6 | 37 | + | + | $10^4$ | $10^4$ |
| 4 | 6 | 38 | + | − | $10^3$ | — |
| 4 | 12 | 39 | − | − | — | — |
| 4 | 12 | 40 | − | − | — | — |
| 5 | 3 | 41 | + | − | $10^4$ | — |
| 5 | 3 | 42 | + | + | $10^4$ | $10^3$ |
| 5 | 4 | 43 | + | − | $10^2$ | — |
| 5 | 4 | 44 | + | − | $10^3$ | — |
| 5 | 5 | 45 | − | + | — | $10^2$ |
| 5 | 5 | 46 | + | − | $10^2$ | — |
| 5 | 6 | 47 | − | − | — | — |
| 5 | 6 | 48 | − | + | $10^2$ | — |
| 5 | 12 | 49 | − | − | — | — |
| 5 | 12 | 50 | − | − | — | — |
| 6 | 3 | 51 | + | + | $10^4$ | $10^5$ |
| 6 | 3 | 52 | + | + | $10^4$ | $10^4$ |
| 6 | 4 | 53 | + | + | $10^2$ | $10^4$ |
| 6 | 4 | 54 | + | + | $10^4$ | $10^3$ |
| 6 | 5 | 55 | + | − | $10^2$ | — |
| 6 | 5 | 56 | + | − | $10^2$ | $10^2$ |
| 6 | 6 | 57 | + | + | $10^3$ | $10^2$ |
| 6 | 6 | 58 | − | + | — | $10^1$ |
| 6 | 12 | 59 | − | − | — | — |
| 6 | 12 | 60 | − | − | — | — |

Cultures results are HCMV cell sonicate cultures during intravenous therapy. Cultures were plated onto 12 wells in a costar cluster. All negative cultures were blind passaged 3 separate times for a total of 28 days in culture. The HCMV titer in positive cultures were determined by standard plaque assay after determination of HCMV presence (positive) in the cultures.

TABLE 15

Time course HCMV recovery from single- and combinational-agent therapy groups: Average Titer of HCMV recovered from chorioretinal sonicates.

| | Days Post Inoculation | | | |
|---|---|---|---|---|
| Therapy Group | 3 | 4 | 5 | 6 |
| Group #1 [50 mg/kg/day PALA] | 2/4*; $10^{3.5}$** | 1/4; $10^{1.5}$ | 2/4; $10^1$ | 4/4; $10^2$ |
| Group #2 [75 mg/kg/day PALA] | 4/4; $10^{4.5}$ | 3/4; $10^{3.75}$ | 1/4; $10^2$ | 2/4; $10^{1.75}$ |
| Group #3 [100 mg/kg/day PALA] | 4/4; $10^4$ | 3/4; $10^3$ | 1/4; $10^2$ | 3/4; $10^{2.5}$ |
| Group #4 [75 mg/kg/day PALA plus 4 | 2/4; $10^3$ | 3/4; $10^{3.5}$ | 1/4; $10^3$ | 3/4; $10^{3.5}$ |

TABLE 15-continued

Time course HCMV recovery from single- and
combinational-agent therapy groups:
Average Titer of HCMV recovered from chorioretinal sonicates.

| Therapy Group | Days Post Inoculation | | | |
|---|---|---|---|---|
| | 3 | 4 | 5 | 6 |
| mg subconjuctival steroid] | | | | |
| Group #5 [10 mg/kg/day DHPG] | 3/4; $10^3$ | 2/4; $10^{1.25}$ | 2/4; $10^2$ | 1/4; $10^1$ |
| Group #6 [placebo] | 4/4; $10^{4.5}$ | 4/4; $10^{3.5}$ | 3/4; $10^{1.25}$ | 3/4; $10^2$ |

13. EXAMPLE 8

Evaluation of PALA and Rifampicin for Inhibition of Vaccinia Virus Replication in the Skin of African Green Monkeys.

Figure 12:
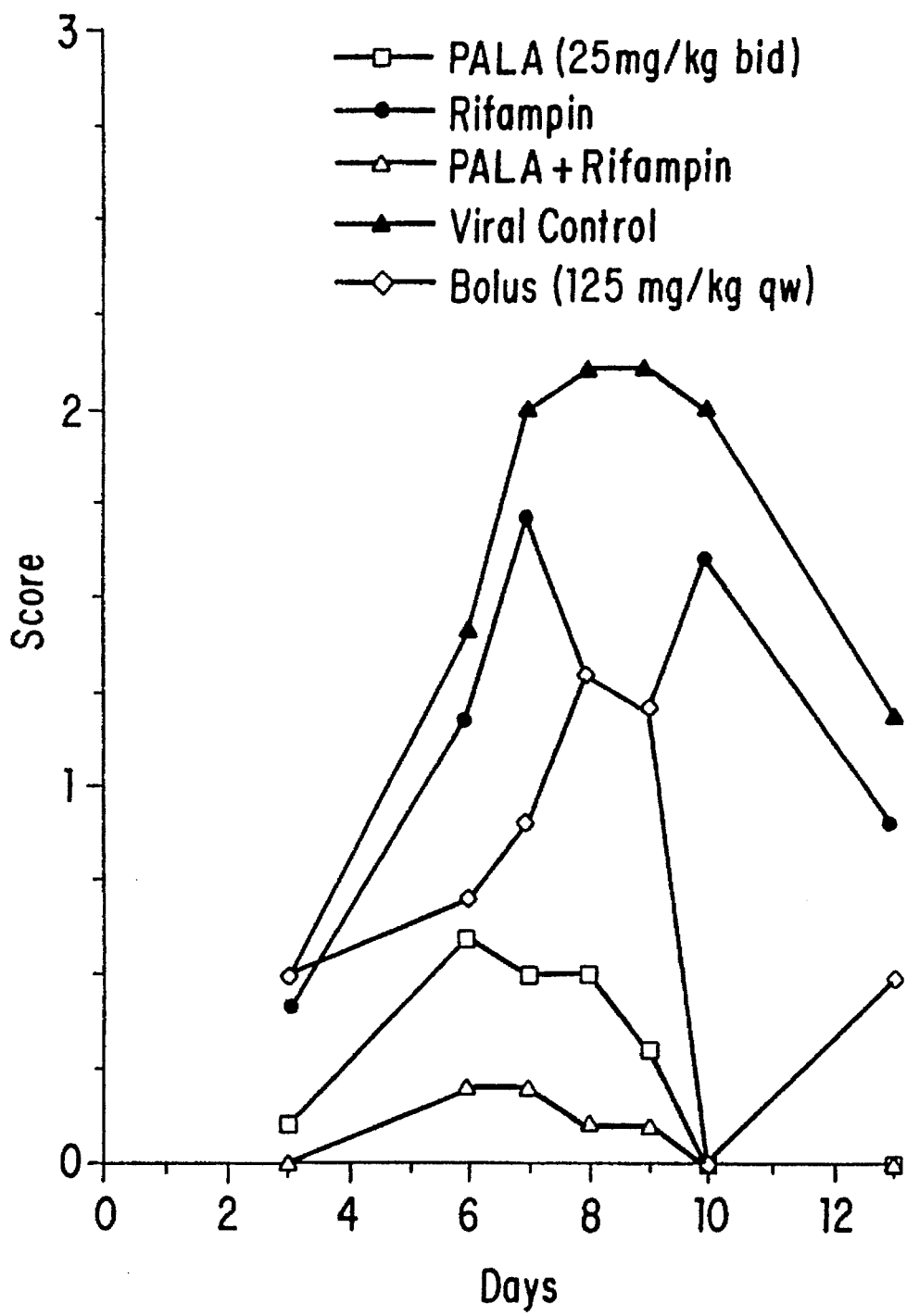
FIG. 12 is a plot of the vaccinia lesion score for the therapy groups of PALA, rifampicin and PALA+rifampicin.
Figure 13:
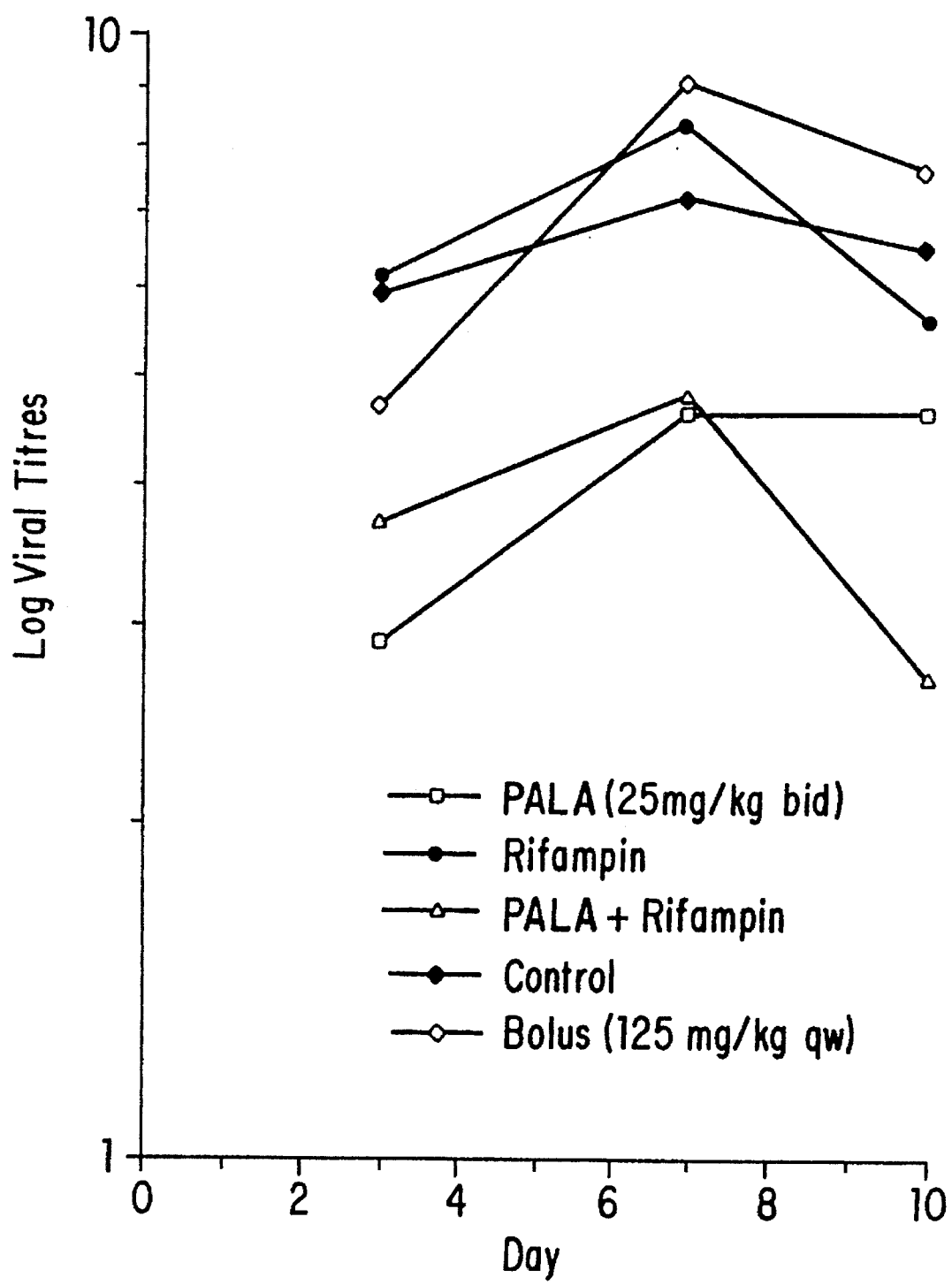
FIG. 13 is a plot of the log of the vaccinia viral titers for the therapy groups PALA, rifampicin and PALA+rifampicin.

The subsections below describe experiments in which African green monkeys were infected with vaccinia virus and treated with PALA, rifampicin and a combination thereof. The results demonstrate that PALA in combination with rifampicin decreased lesion better than any other therapy (FIG. 12). In addition, lower titers of virus were found both in the monkeys receiving PALA alone at 50 mg/kg/day and in those receiving PALA and rifampicin combinational therapy (FIG. 13).

13.1 Materials and Methods

Fifteen adult African green monkeys were used in an experiment to evaluate a compound designated PALA alone and in combination with rifampicin for the ability to inhibit infection by vaccinia virus. Prior to beginning the study sera from each of the 15 monkeys was tested at a 1:10 dilution for seronegativity to vaccinia virus. The test employed was a serum neutralization assay employing 100 TCID$_{50}$ of virus.

Infection with vaccinia virus was a dermal infection produced by injection of 0.1 ml of a 1:100 dilution of stock virus intradermally into each of eight sites on the shaved back of each monkey. Titration of the viral inoculum showed that each injection site received $10^6$ TCID$_{50}$ of virus.

Following virus injection the monkeys were grouped to five groups of three monkeys each with the resulting assignment presented in Table 1. Prior to virus inoculation, each monkey was weighed and 5 ml of blood was drawn for baseline plasma and lymphocyte samples.

Treatment with PALA and/or rifampicin was started 24 hours after virus inoculation. Both drugs were prepared fresh daily prior to treatment. PALA was provided in vials containing 5 ml of a solution at 1 00 mg/ml. A 1:4 dilution was prepared in pH 7.2 PBS resulting in a drug concentration of 25 mg/ml. Monkeys in group 1 and 3 received PALA at 50 mg/kg/day which was given by intravenous injection in divided doses at 8 a.m. and 8 p.m. daily. The PALA solution of 25 mg/ml was given into the saphenous vein as 1 ml per kg of body weight.

Rifampicin was weighed out in 300 mg aliquots which was dissolved in 10 ml DMSO and brought to a 60 ml volume. This dilution resulted in a concentration of 5 mg/ml. Groups 2 and 3 received intravenous injections of 1 ml per kg of body weight or 5 mg/kg. Twice daily treatment, at 8 a.m. and 8 p.m., resulted in a daily dose of 10 mg/kg.

Monkeys in group 5 received PALA at 125 mg/kg given as single intravenous injections on Day 1 and Day 7 post-infection. Group 4 was an infection control group which was administered PBS by intravenous injection at 8 a.m. and 8 p.m. daily. All treatments continued for 10 days.

Infection was evaluated by daily examination of the lesion sites and scoring them on a scale of ± to 4+ in relation to increased severity. The total score for each monkey was determined by adding the individual lesion scores and a mean value determined by dividing the score by the number of injection sites. This provided a daily mean lesion score for each monkey.

In addition, on days 3, 7, and 10 post-infection, one lesion site from each monkey was biopsied using an 8 mm dermal punch. The biopsy site was closed by suturing. Each piece of biopsied skin was transferred to a glass tissue grinder and the tissue homogenized in 2 mi of tissue culture medium (minimum essential medium with 2 percent fetal bovine serum and antibiotics). The tissue homogenates were titrated for vaccinia virus by preparation of serial ten fold dilutions which were cultured in duplicate in 24 well culture plates containing Vero cells. After 4 days incubation, the cultures were fixed in methanol, stained with methylene blue-basic fuchsin and the number of plaques counted.

On days 0, 3, 6, 8 and 10 post-infection, 5 ml of blood was collected in heparin and the plasma and cells separated. The plasma was frozen at −200C. and the cells diluted 1:1 with PBS and layered on a ficoll-hypaque gradient. Following centrifugation at 1400 rpm for 30 minutes, the lymphocyte band was collected, washed twice in RPMI-1640 medium with 15 percent fetal bovine serum. Following the second washing the culture medium was removed and the sedimented cells suspended in a solution of 1 mM dithiothreitol, 1 mM EDTA and 10 mM magnesium acetate and frozen at −70° C.

The monkeys were weighed at 10, 14 and 21 days and bled at 14 and 21 days for determination of antibody titers to vaccinia virus. Antibody titers were determined by a serum neutralization assay.

13.2 Results

Mean lesion scores for each monkey are shown in Table 16. Lesions were scored on days 3, 6, 7, 8, 9, 10 and 13 from all of the sites on the back of each monkey and the means were calculated. The mean scores for each group of monkeys was determined for each day and is seen in bold type. The data indicate that PALA at 50 mg/kg/day and PALA at 50 mg/kg/day in combination with rifampicin at 10 mg/kg/day were effective in reducing lesion development and size. Two of the infection control monkeys had appreciable lesions while one control monkey had moderate lesions. The monkeys treated with rifampicin were also seen to have appreciable skin lesions, again with two monkeys showing more severe infection than a third monkey. In the group receiving PALA at 125 mg/kg administered (as a bolus) on day 1 and day 7 post-infection one monkey died four hours following dosing. The gross pathology findings consisted of dark red discoloration of the liver suggesting the possibility of acute shock or toxicity. Histopathology findings will be reported later. With respect to lesion appearance, one monkey at the high dose of PALA showed fairly severe lesions while the other had more moderate lesions. The severity of the lesions in monkeys treated with the high dose of PALA on days 1 and 7 postinfection were greater than what was seen in monkeys treated daily with PALA at a lower dose.

Titration of virus in skin biopsies from each of the monkeys showed variation from monkey to monkey within each treatment group as well as in the controls (Table 3). Higher titers of vaccinia virus were seen in the infection control group, the rifampicin group and in the high dose PALA group. Lower titers of virus were present in the monkeys receiving PALA at 50 mg/kg/day and in the group receiving both PALA and rifampicin.

No appreciable signs of toxicity were seen in any of the monkeys treated with PALA or with rifampicin with the exception of the single monkey dying following the administration of PALA at 125 mg/kg (bolus). The two surviving monkeys receiving this dose, received a second injection at 125 mg/kg on the seventh day post-infection without any adverse signs.

TABLE 16

Vaccinia Lesion Scores From Inoculation Sites on Backs of African Green Monkeys Infected With Vaccinia Virus

| Treatment Group | Monkey Number | Vaccinia Lesion Score* on Days Post-infection | | | | | | |
|---|---|---|---|---|---|---|---|---|
| | | 36** | 7** | 8*** | 9*** | 10**** | 13**** | |
| PALA: 50 mg/kg/d, b.i.d., i.v. | M634 | 0.4 | 0.4 | 0.5 | 0.2 | 0.2 | 0 | 0 |
| | M638 | 0 | 1.0 | 0.9 | 1.2 | 0.8 | 0 | 0 |
| | M643 | 0 | 0.3 | 0 | 0 | 0 | 0 | 0 |
| | x | 0.1 | 0.6 | 0.5 | 0.5 | 0.3 | 0 | 0 |
| Rifampicin: 10 mg/kg/d, b.i.d., i.v. | M647 | 0.9 | 1.6 | 2.6 | 2.8 | 2.4 | 2.7 | 2.2 |
| | M637 | 0 | 0.7 | 0.5 | 0.1 | 0.1 | 0 | 0 |
| | M640 | 0.4 | 1.4 | 2.0 | 1.1 | 1.2 | 0.5 | 0.5 |
| | x | 0.4 | 1.2 | 1.7 | 1.3 | 1.2 | 1.6 | 0.9 |
| PALA + Rifampicin b.i.d., i.v. | M645 | 0 | 0.3 | 0.2 | 0.1 | 0.1 | 0.1 | 0.1 |
| | M641 | 0.1 | 0.2 | 0.1 | 0 | 0 | 0 | 0 |
| | M642 | 0 | 0.2 | 0.2 | 0.1 | 0.2 | 0 | 0 |
| | x | 0 | 0.2 | 0.2 | 0.1 | 0.1 | 0 | 0 |
| Control: PBS, b.i.d., i.v. | M636 | 0.9 | 1.9 | 2.9 | 3.7 | 3.8 | 3.7 | 2.8 |
| | M636 | 0.1 | 0.6 | 0.7 | 0.5 | 0.3 | 0 | 0 |
| | M639 | 0.4 | 1.6 | 2.4 | 2.2 | 2.2 | 2.2 | 0.9 |
| | x | 0.5 | 1.4 | 2.0 | 2.1 | 2.1 | 2.0 | 1.2 |
| PALA: 125 mg/kg, Day 1 & Day 7 | M407 | Dead | | | | | | |
| | M431 | 0 | 0.3 | 0.4 | 0.7 | 0.3 | 0 | 0.3 |
| | M410 | 1.0 | 1.0 | 1.4 | 1.8 | 2.0 | 0 | 0.7 |
| | x | 0.5 | 0.7 | 0.9 | 1.3 | 1.2 | 0 | 0.5 |

*Scored on a scale of + to 4+ in relation to increasing severity. Each score represents mean of 7 (), 6 (*) or 5 (****) sites from each monkey.

TABLE 17

Titers of Vaccinia Virus* in Homogenates of Skin Lesion Biopsies From African Green Monkeys

| Treatment Group | Monkey Number | PFU/ml on Days Post-infection | | |
|---|---|---|---|---|
| | | 3 | 7 | 6 |
| PALA: 50 mg/kg/day b.i.d., i.v. | M637 | $8.5 \times 10^3$ | $7.5 \times 10^6$ | $1.5 \times 10^5$ |
| | M640 | $3.5 \times 10^3$ | $9 \times 10^4$ | $1.6 \times 10^5$ |
| | M645 | $4.5 \times 10^1$ | $1.1 \times 10^2$ | $5 \times 10^2$ |
| Rifampicin: 10 mg/kg/day, | M641 | $5.5 \times 10^6$ | $8.5 \times 10^8$ | $1.5 \times 10^7$ |
| | M634 | $2.5 \times 10^3$ | $1.0 \times 10^6$ | $1.2 \times 10^5$ |
| | M638 | $9 \times 10^5$ | $>50 \times 10^9$ | $1.1 \times 10^5$ |

TABLE 17-continued

Titers of Vaccinia Virus* in Homogenates of Skin Lesion Biopsies From African Green Monkeys

| Treatment Group | Monkey Number | PFU/ml on Days Post-infection | | |
|---|---|---|---|---|
| | | 3 | 7 | 6 |
| b.i.d., i.v. PALA + Rifampicin | M643 | $2.5 \times 10^3$ | $5 \times 10^3$ | $7 \times 10^4$ |
| | M647 | $3 \times 10^4$ | $1.2 \times 10^6$ | $1.7 \times 10^2$ |
| | M642 | $8.5 \times 10^3$ | $1.4 \times 10^5$ | $5.5 \times 10^1$ |
| Control PBS, b.i.d., i.v. | M636 | $9 \times 10^6$ | $8 \times 10^8$ | $9 \times 10^7$ |
| | M635 | $6 \times 10^4$ | $1.4 \times 10^5$ | $2 \times 10^6$ |
| | M639 | $5.5 \times 10^3$ | $1.2 \times 10^8$ | $3.5 \times 10^5$ |
| PALA: 125 mg/kg, Day 1 & Day 7 | M407 | Dead | | |
| | M431 | $3 \times 10^5$ | $1.2 \times 10^7$ | $1.3 \times 10^5$ |
| | M410 | $3 \times 10^4$ | $>100 \times 10^9$ | $1.8 \times 10^{10}$ |

*8 mm biopsies were homogenized in 2.0 ml of tissue culture medium and titrated in duplicate wells of 24 well plates seeded with Vero cells.

TABLE 18

Neutralizing Antibody Titers to Vaccinia Virus in Monkeys Infected With Vaccinia Virus and Treated With PALA and/or Rifampicin

| Treatment Group | Monkey Number | Neutralizing Antibody to Vaccinia Virus | |
|---|---|---|---|
| | | 14 days p.i. | 21 days p.i. |
| PALA: 50 mg/kg/day b.i.d., i.v | M637 | 1:10 | 1:80 |
| | M640 | <1:10 | 1:160 |
| | M645 | <1:10 | 1:40 |
| Rifampicin: 10 mg/kg/day, b.i.d., i.v. | M641 | 1:10 | 1:160 |
| | M634 | <1:10 | 1:160 |
| | M638 | <1:10 | 1:80 |
| PALA + Rifampicin | M643 | <1:10 | 1:80 |
| | M647 | <1:10 | 1:80 |
| | M642 | <1:10 | 1:40 |
| Control: PBS, b.i.d., i.v. | M636 | <1:10 | 1:160 |
| | M635 | <1:10 | 1:160 |
| | M639 | <1:10 | 1:160 |
| PALA: 125 mg/kg, Day 1 & Day 7 | M407 | Dead | Dead |
| | M431 | 1:40 | 1:320 |
| | M410 | <1:10 | 1:80 |

TABLE 19

Weights of African Green Monkeys Infected With Vaccinia Virus and Treated With PALA and/or Rifampicin

| Treatment Group | Monkey Number | Weights (kg) on Days Post Infection | | | |
|---|---|---|---|---|---|
| | | 0 | 10 | 14 | 21 |
| PALA: 50 mg/kg/day b.i.d., i.v. | M634 | 2.4 | 2.2 | 2.0 | 2.0 |
| | M638 | 3.4 | 3.2 | 3.2 | 3.4 |
| | M643 | 2.6 | 2.4 | 2.4 | 2.6 |
| Rifampicin: 10 mg/kg/day, b.i.d., i.v. | M647 | 5.2 | 4.6 | 4.6 | 4.8 |
| | M637 | 2.6 | 2.4 | 2.4 | 2.6 |
| | M640 | 4.2 | 3.8 | 3.8 | 4.0 |
| PALA + Rifampicin | M645 | 2.8 | 2.8 | 2.8 | 2.8 |
| | M641 | 3.8 | 3.8 | 4.0 | 4.2 |
| | M642 | 2.4 | 2.2 | 2.0 | 2.2 |
| Control: PBS, b.i.d., i.v. | M636 | 3.4 | 3.4 | 3.2 | 3.6 |
| | M635 | 2.6 | 2.4 | 2.6 | 2.6 |
| | M639 | 3.6 | 3.4 | 3.6 | 3.6 |
| PALA: 125 mg/kg, Day 1 & Day 7 | M407 | 3.2 | Dead | | |
| | M431 | 3.4 | 3.2 | 3.2 | 3.4 |
| | M410 | 4.4 | 4.4 | 4.4 | 4.2 |

14. EXAMPLE 9

Study of PALA against respiratory syncytial virus (RSV) by the cotton rat.

Figure 11:
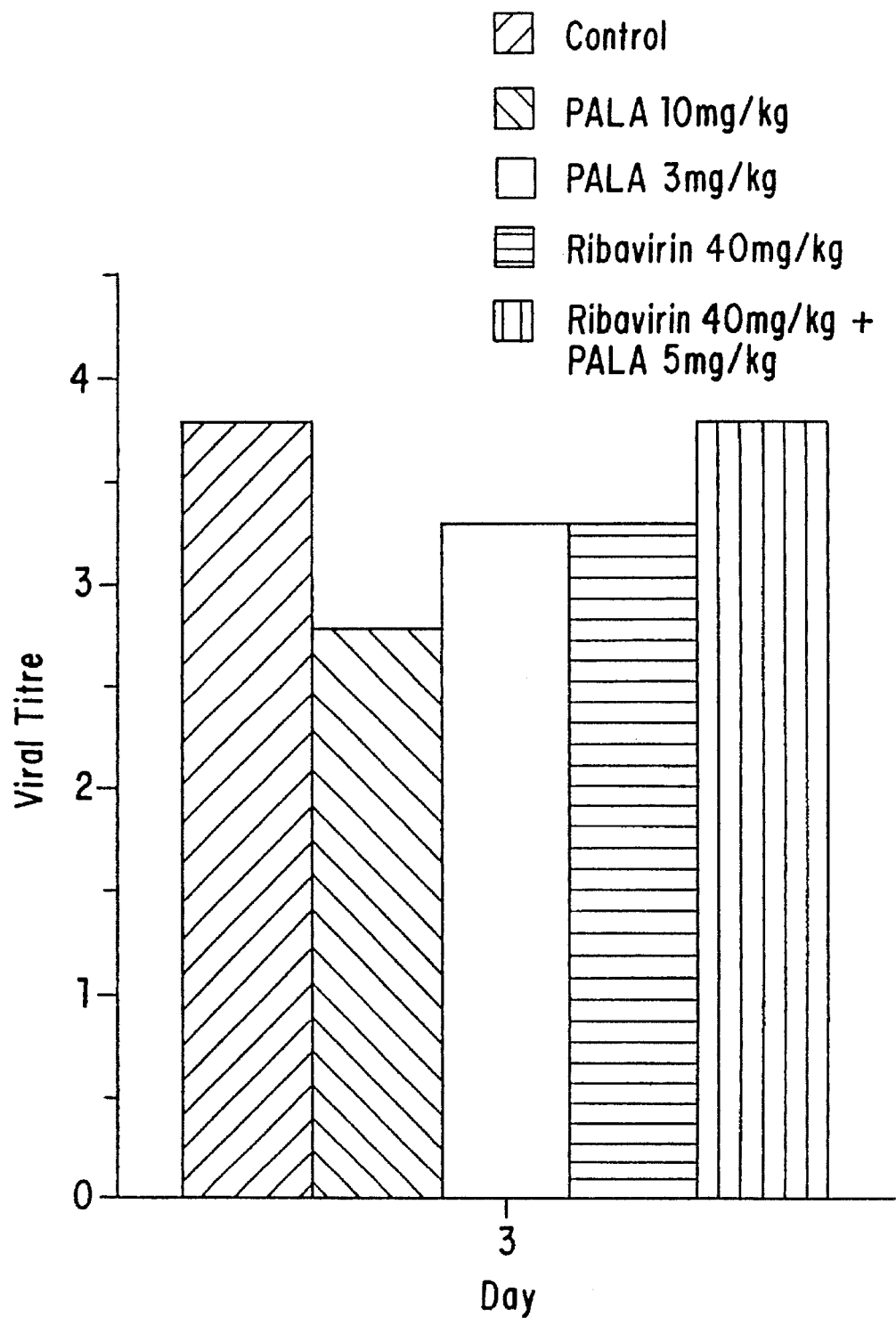
FIG. 11 is a bar graph of the viral titre for the therapy groups of PALA, PALA+ribavirin and control.

The subsections below describe experiments in which cotton rats were preinfected with respiratory syncytial virus and treated for four days with PALA, ribavirin, or a combination thereof. The results (FIG. 11) demonstrate that PALA at 10 mg/kg/day was more effective than ribavirin or combinational therapy (as confirmed by a reduction in histopathology and viral titres—decreased by one 1 $\log_{10}$ over control).

14.1 Materials and Methods

Cotton rats (outbred Sigmoden hispidus), either sex, 50 to 100 g were challenged with RSV (strain A1), using approximately 100 cotton rat median infectious doses (CRID50; 100 µl given i.n.). Therapy consisted of PALA (30 mg/kg/day), ribavirin (30 mg/kg/day), or combinational therapy. All test compounds were given intra-peritoneally (i.p.) for four days. Animals sacrificed on day (+)4, lungs homogenized and titered for RSV. Total number of animals used was 24. Experimental Protocol: respiratory syncytial virus (RSV) in cotton rats preliminary in vivo screens (16 animals were used).

| GROUP | TEST COMPOUND (mg/kg) (day) | DAYS DRUG IS GIVEN | DOSE (mg/kg) (day) | END-POINT |
|---|---|---|---|---|
| 1 | None (H₂O) | −1 through +3 | 0* | Lung virus titre on day +4 |
| 2 | RIBAVIRIN | +1 through +3 | 30 | |
| 3 | PALA | −1 through +3 | 30 | |
| 4 | PALA RIBAVIRIN | −1 through +3 +1 through +3 | 30 90 | |

*(Day 0 = day of virus inoculation; dose of each drug and schedule used subject to change dependent on the results of experiment 1.)

| | | | | |
|---|---|---|---|---|
| RESPIRATORY SYNCYTIAL VIRUS LUNG TITRES ($\text{LOG}_{10}$) PALA VS RIBAVIRIN EXPERIMENT AGAIN RSV | | | | |
| REC # | PLACEBO | RIBAVIRIN (40 mg/kg) | PALA (10 mg/kg) | PALA (3 mg/kg) | RIBAVIRIN (40 mg) + PALA (3 mg/kg) |
| 1 | 4.5 | 3.4 | 2.4 | 3.9 | 4.0 |
| 2 | 3.5 | 2.9 | 2.9 | 3.5 | 3.9 |
| 3 | 3.5 | 3.5 | 2.5 | 2.9 | 4.0 |
| 4 | 3.5 | 3.5 | 3.5 | 3.0 | 3.5 |

Statistical Evaluation Difference Between Two Means: T Test With One Way Anova Variable For T Test: PLACEBO vs PALA 10 mg/kg/d (t = 3.1650; df = 15; Two-tailed p = 0.0064).

14.2 Summary of Results of an Experiment Testing PALA for Antiviral Activity Against RSV in Cotton Rats

14.2.1 Procedure 1. 50 to 100 g cotton rats of either sex inoculated i.n. with RS A2 (pool 8-28-92) on day 0.

2. On day +1 animals were given placebo or PALA as follows:

| | | |
|---|---|---|
| Group 1: | Placebo (H₂O) i.p. | Day +1–Day +3 |
| Group 2: | PALA 3 mg/kg/d i.p. | Day +1–Day +3 |
| Group 3: | PALA 10 mg/kg/d i.p. | Day +1–Day +3 |
| Group 4: | Ribavirin 40 mg/kg/d i.p. | Day +1–Day +3 |
| Group 5: | Ribavirin 40 mg/kg/d + PALA 3 mg/kg/d i.p. | Day +1–Day +3 |

3. All animals killed on day +4 and their lungs tested for RSV levels.

| | | 14.2.2 RESULTS | | |
|---|---|---|---|---|
| GROUP | TREATMENT | (mg/kg/day) | $\text{LOG}_{10}/\text{G}$ Lung (SD) | TITRES |
| 1 | PLACEBO | — | 3.8 (0.5) | 4.5, 3.5, 3.5, 3.5 |
| 2 | PALA | 3 | 3.3 (0.3) | 3.9, 3.5, 2.9, 3.0 |
| 3 | PALA | 10 | <u>2.8 (0.5)</u> | 2.4, 2.9, 3.5, 2.5 |
| 4 | RIBAVIRIN | 40 | <u>3.3 (0.3)</u> | 3.4, 2.9, 3.5, 3.5 |
| 5 | RIBAVIRIN + PALA | (40 + 3) | 3.9 (0.2) | 4.0, 3.9, 4.0, 3.5 |

Underlined means significantly different form mean of placebo animals p < 0.05 using the Kruskal-Wallis nonparametric ANOVA test and the Newman-Keuls test for multiple comparisons. Using the t-Test with a 1-way ANOVA is even more significant.

| STATISTICAL EVALUATION* OF PALA VS RIBAVIRIN | | | |
|---|---|---|---|
| NUMBER | THERAPY USED** | MEAN RANK | C.I. OVERLAPS |
| 1 | PALA (10 mg) | 4.6250 | 2, 3 |
| 2 | RIBAVIRIN (90 mg) | 8.5000 | 1, 3, 4, 5 |
| 3 | PALA (3 mg) | 9.5000 | 1, 2, 4, 5 |
| 4 | PLACEBO | 13.6250 | 2, 3, 5 |
| 5 | RIBAVIRIN (40 mg) + PALA (5 mg) | 16.2500 | 2, 3, 4 |

*Newman-Keuls Multiple Comparisons Procedure.
**Therapy used in mg/kg/day (interperitoneal).

14.3 Conclusion

The results show statistically significant efficacy of PALA as a single drug against respiratory syncytial virus. PALA was statistically better than ribavirin. There appears to be no additive and/or synergistic effect between PALA and ribavirin.

It may apparent to those skilled in the art that modifications and variations of the present invention are possible in light of the above disclosure. It is understood that such modifications are within the spirit and scope of the invention, which is defined by the appended claims.

What is claimed is:

1. A method of treating viral infection caused by an RNA virus selected from the group consisting of flaviviruses, bunyaviruses, Hantaan and filoviruses which comprises administering to a mammal in need of antiviral therapy an effective amount of N-(phosphonoacetyl)-L-aspartic acid or a pharmaceutically acceptable analog thereof.

2. A method of treating viral infection caused by an RNA virus selected from the group consisting of yellow fever, sandfly fever, Rift Valley fever, Dengue virus 1–4, Coxsackie, measles, respiratory syncytial, parainfluenza and influenza A ($H_2N_2$ and $H_3N_2$) viruses which comprises administering to a mammal in need of antiviral therapy an effective amount of N-(phosphonoacetyl)-L-aspartic acid or a pharmaceutically acceptable analog thereof.

3. A method of treating viral infection caused by a DNA herpes virus which comprises administering to a mammal in need of antiviral therapy an effective amount of N-(phosphonoacetyl)-L-aspartic acid or a pharmaceutically acceptable analog thereof.

4. A method of treating disease caused by hepatitis C virus which comprises administering to a mammal in need of such therapy, an effective antiviral amount of N-(phosphonoacetyl)-L-aspartic acid or a pharmaceutically acceptable analog thereof.

5. A method of treating disease caused by hepatitis B virus which comprises administering to a mammal in need of such therapy an effective antiviral amount of N-(phosphonoacetyl)-L-aspartic acid or a pharmaceutically acceptable analog thereof.

6. A method of in which treating vital infection caused by an opportunistic viral infection, secondary to HIV-1 or HIV-2, chemotherapy or other causes of immunosuppression which comprises administering to a mammal in need of antiviral therapy an effective amount of N-(phosphonoacetyl)-L-aspartic acid or a pharmaceutically acceptable analog thereof.

7. The method of claims 1, 2, 3 or 6 in which said administration is made parenterally or orally.

8. The method of claims 1, 2, 3 or 6 in which said administration is made topically, vaginally or rectally.

9. The method of claims 1, 2, 3 or 6 in which about 1 mg/kg/day to about 100 mg/kg/day of N-(phosphonoacetyl)-L-aspartic acid or a pharmaceutically acceptable analog thereof is administered to said mammal.

10. The method of claim 9 in which about 25 mg/kg/day to about 50 mg/kg/day of N-(phosphonoacetyl)-L-aspartic acid or a pharmaceutically acceptable analog is administered to said mammal.

11. The method of claim 9 in which about 5 to about 60 mg/kg/day of N-(phosphonoacetyl)-L-aspartic acid or a pharmaceutically acceptable analog is administered to said mammal.

12. The method of claim 3 wherein said herpes virus is selected from the group consisting of varicella, cytomegalovirus and human herpesvirus-6.

13. The method of claim 6 wherein said opportunistic viral infection is selected from the group consisting of molluscum contagiosum virus, cytomegalovirus and varicella-zoster viruses.

* * * * *